United States Patent
Ameer et al.

(10) Patent No.: US 12,036,234 B2
(45) Date of Patent: Jul. 16, 2024

(54) HEPARIN CONJUGATED TO COLLAGEN-BINDING PEPTIDES FOR TARGETING TO BIOLOGICAL AND SYNTHETIC TISSUES

(71) Applicant: Northwestern University, Evanston, IL (US)

(72) Inventors: Guillermo A. Ameer, Chicago, IL (US); Jason A. Wertheim, Chicago, IL (US); Bin Jiang, Evanston, IL (US); Kyle Koss, Evanston, IL (US)

(73) Assignee: Northwestern University, Evanston, IL (US)

( * ) Notice: Subject to any disclaimer, the term of this patent is extended or adjusted under 35 U.S.C. 154(b) by 331 days.

(21) Appl. No.: 16/755,494

(22) PCT Filed: Oct. 11, 2018

(86) PCT No.: PCT/US2018/055434
§ 371 (c)(1),
(2) Date: Apr. 10, 2020

(87) PCT Pub. No.: WO2019/075213
PCT Pub. Date: Apr. 18, 2019

(65) Prior Publication Data
US 2021/0299158 A1    Sep. 30, 2021

Related U.S. Application Data

(60) Provisional application No. 62/570,904, filed on Oct. 11, 2017.

(51) Int. Cl.
| | | |
|---|---|---|
| *A61K 31/727* | (2006.01) | |
| *A61K 38/08* | (2019.01) | |
| *A61K 47/54* | (2017.01) | |
| *A61K 47/64* | (2017.01) | |

(52) U.S. Cl.
CPC ............ *A61K 31/727* (2013.01); *A61K 38/08* (2013.01); *A61K 47/547* (2017.08); *A61K 47/6425* (2017.08)

(58) Field of Classification Search
CPC ...... A61K 31/00; A61K 31/727; A61K 31/70; A61K 38/00; A61K 38/08; A61K 47/00; A61K 47/547; A61K 47/6425; A61K 47/64; A61P 7/02; A61P 9/00
USPC ...... 424/1.11, 1.65, 1.81, 1.85, 9.1, 9.2, 9.3, 424/9.4, 9.5, 9.6
See application file for complete search history.

(56) References Cited

U.S. PATENT DOCUMENTS

| | | | |
|---|---|---|---|
| 7,396,664 B2 | 7/2008 | Daly | |
| 8,758,796 B2 | 6/2014 | Ameer | |
| 8,772,437 B2 | 7/2014 | Ameer | |
| 8,992,967 B2 | 3/2015 | Ameer | |
| 9,200,039 B2 | 12/2015 | Panitch | |
| 9,707,281 B2 | 7/2017 | Kibbe | |
| 9,750,845 B2 | 9/2017 | Ameer | |
| 9,981,066 B2 | 5/2018 | Dimitrievska | |
| 10,406,385 B2 | 9/2019 | Ameer | |
| 10,463,745 B2 | 11/2019 | Zhu | |
| 10,463,769 B2 | 11/2019 | Ameer | |
| 10,561,761 B2 | 2/2020 | Xiao | |
| 2012/0100106 A1 | 4/2012 | Panitch | |
| 2013/0190246 A1 | 7/2013 | Paderi | |
| 2014/0058049 A1 | 2/2014 | Ameer | |
| 2014/0066587 A1 | 3/2014 | Ameer | |
| 2014/0155516 A1 | 6/2014 | Ameer | |
| 2014/0322190 A1 | 10/2014 | Kibbe | |
| 2015/0099853 A1 | 4/2015 | Ameer | |
| 2015/0297802 A1 | 10/2015 | Ameer | |
| 2016/0045606 A1 | 2/2016 | Baler | |
| 2016/0331841 A1* | 11/2016 | Prestwich | ............... A61P 27/06 |
| 2017/0360992 A1 | 12/2017 | Ameer | |
| 2017/0368192 A1 | 12/2017 | Paderi | |
| 2017/0368377 A1 | 12/2017 | Ameer | |
| 2018/0085492 A1 | 3/2018 | Ameer | |
| 2018/0117219 A1 | 5/2018 | Yang | |
| 2018/0125990 A1 | 5/2018 | Zhu | |
| 2018/0154009 A1 | 6/2018 | Yang | |
| 2018/0236122 A1 | 8/2018 | Xiao | |
| 2018/0303941 A1 | 10/2018 | Ameer | |

(Continued)

FOREIGN PATENT DOCUMENTS

| | | |
|---|---|---|
| WO | 1997036619 A2 | 10/1997 |
| WO | 2006044512 A1 | 4/2006 |

(Continued)

OTHER PUBLICATIONS

Morris et al, Protein Expression and Purification, vol. 126, pp. 93-103 (Year: 2016).*
Jian et al, Biomacromolecules (Nov. 2, 2016), vol. 17, pp. 3940-3948. (Year: 2016).*
Abd-Elgaliel et al. (2013), Exploring the Structural Requirement of Collagen-Binding Peptides. Biopoplymers April 100(2): 167-173.
Beyer, J. et al. Evaluation of a Heparin-Calibrated Antifactor Xa Assay for Measuring the Anticoagulant Effect of Oral Direct Xa Inhibitors. Clin. Appl. Thromb. Hemost. 22, 423-428 (2016).

(Continued)

*Primary Examiner* — D. L. Jones
(74) *Attorney, Agent, or Firm* — Quarles & Brady LLP

(57) ABSTRACT

Disclosed are heparin conjugates comprising heparin conjugated to a peptide that binds to a protein of the extracellular matrix (ECM) of cellular tissue, such as a collagen-binding peptide that binds to collagen of the ECM. The disclosed heparin conjugates may be utilized in methods that include treating ECM material to incorporate the heparin conjugates and impart anticoagulant activity to the ECM. The disclosed heparin conjugates also may be formulated as pharmaceutical compositions for treating and/or preventing vascular injuries and conditions.

16 Claims, 22 Drawing Sheets

Specification includes a Sequence Listing.

(56) References Cited

U.S. PATENT DOCUMENTS

| | | |
|---|---|---|
| 2019/0282735 A1 | 9/2019 | Ameer |
| 2019/0336648 A1 | 11/2019 | Ameer |
| 2019/0345262 A1 | 11/2019 | Ameer |
| 2020/0179574 A1 | 6/2020 | Yang |
| 2020/0383917 A1 | 12/2020 | Scott |
| 2020/0384113 A1 | 12/2020 | Ameer |
| 2020/0390938 A1 | 12/2020 | Ameer |
| 2021/0008246 A1 | 1/2021 | Ameer |
| 2021/0106697 A1 | 4/2021 | Scott |
| 2021/0299158 A1 | 9/2021 | Ameer |
| 2021/0307731 A1 | 10/2021 | Grayson |
| 2021/0346576 A1 | 11/2021 | Yang |

FOREIGN PATENT DOCUMENTS

| | | |
|---|---|---|
| WO | 2010129547 A1 | 11/2010 |
| WO | 2014059530 A1 | 4/2014 |
| WO | 2014144969 A1 | 9/2014 |
| WO | 2014189835 A2 | 11/2014 |
| WO | 2016100846 A1 | 6/2016 |

OTHER PUBLICATIONS

Bjornsson TD, et al. Pharmacokinetics of heparin. II. Studies of time dependence in rats. J Pharmacol Exp Ther. 1979;210(2):243-6.

Bruinsma BG, et al. Layer-by-layer heparinization of decellularized liver matrices to reduce thrombogenicity of tissue engineered grafts. Journal of clinical and translational research. 2015;1(1):04.

Bultel L, et al. UV-MALDI-TOF mass spectrometry analysis of heparin oligosaccharides obtained by nitrous acid controlled degradation and high performance anion exchange chromatography. J Am Soc Mass Spectrom. 2010;21(1):178-90.

Castellot JJ, Jr., et al. Structural determinants of the capacity of heparin to inhibit the proliferation of vascular smooth muscle cells. II. Evidence for a pentasaccharide sequence that contains a 3-O-sulfate group. J Cell Biol. 1986;102(5):1979-84.

Colas-Linhart N, et al. Technetium 99m labelled heparin: pharmacokinetics and tissue distribution in rats after vascular surgery. Biomed Pharmacother. 1987;41(4):189-91.

Depraetere et al. (1998) Identification of peptides, selected by phage display technology, that inhibit von Willebrand factor binding to collagen. Blood. 92, 4207-4211.

Dufresne M, et al. Explants of porcine coronary artery in culture: A paradigm for studying the influence of heparin on vascular wall cell proliferation. Cytotechnology. 2001;37(1):13-22.

Ferrara, N.; et al. Pituitary follicular cells secrete a novel heparin-binding growth factor specific for vascular endothelial cells. Biochem. Biophys. Res. Commun. 1989, 161 (2), 851-8.

Helander HF, et al. Surface area of the digestive tract—revisited. Scand J Gastroenterol. 2014;49(6):681-9.

Helms et al. (2009) High-Affinity Peptide-Based Collagen Targeting Using Synthetic Phage Mimics: From Phage Display to Dendrimer Display. J. Am. Chem. Soc. 131(33), 11683-11685.

Higashiyama, S.; et al. A Heparin-Binding Growth-Factor Secreted by Macrophage-Like Cells That Is Related to Egf. Science 1991, 251 (4996), 936-939.

Hoshi, R. A.; et al. The blood and vascular cell compatibility of heparin modified ePTFE vascular grafts. Biomaterials 2013, 34 (1), 30-41.

International Searching Authority. International Search Report and written opinion for application PCT/US2018/055434, dated Oct. 11, 2018. 7 pages.

Jiang, B., et al. "Targeting heparin to collagen within extracellular matrix significantly reduces thrombogenicity and improves endothelialization of decellularized tissues." Biomacromolecules 17.12 (2016): 3940-3948.

Keire DA, et al. Analysis of crude heparin by (1)H NMR, capillary electrophoresis, and strong-anion-exchange-HPLC for contamination by over sulfated chondroitin sulfate. J Pharm Biomed Anal. 2010;51(4):921-6.

Kim JY, et al. Preclinical safety evaluation of low molecular weight heparin-deoxycholate conjugates as an oral anticoagulant. Journal of applied toxicology : JAT. 2016;36(1):76-93.

Laforest MD, et al. Pharmacokinetics and biodistribution of technetium 99m labelled standard heparin and a low molecular weight heparin (enoxaparin) after intravenous injection in normal volunteers. Br J Haematol. 1991;77(2):201-8.

Lee et al. (2007) Assembly of collagen-binding peptide with collagen as a bioactive scaffold for osteogenesis in vitro and in vivo. Biomaterials. Oct;28(29):4257-67.

Lin PH, et al. Heparin-coated balloon-expandable stent reduces intimal hyperplasia in the iliac artery in baboons. J Vasc Interv Radiol. 2003;14(5):603-11.

Lin, P.H., et al., Carotid stenting using heparin-coated balloon-expandable stent reduces intimal hyperplasia in a baboon model. J Surg Res, 2003. 112(1): p. 84-90.

Liu, H., et al. Lessons learned from the contamination of heparin. Nat Prod Rep, 2009. 26(3): p. 313-21.

Meyers MW, et al. Systemically administered collagen-targeted gold nanoparticles bind to arterial injury following vascular interventions. Physiol Rep. 2017;5(4).

Murugesan, S., et al. Immobilization of Heparin: Approaches and Applications. Curr Top Med Chem 8, 80-100 (2008).

Muzzard et al. (2009) Non-invasive molecular imaging of fibrosis using a collagen-targeted peptidomimetic of the platelet collagen receptor glycoprotein VI. PLoS one. 4 (e5585) 1-10.

Ndinguri MW, et al. Application of Collagen-Model Triple-Helical Peptide-Amphiphiles for CD44-Targeted Drug Delivery Systems. J Drug Deliv. 2012;2012:592602.

Ofosu, F.A., A review of the two major regulatory pathways for non-proprietary low-molecular-weight heparins. Thromb Haemost, 2012. 107(2): p. 201-14.

Paderi, J. E.; et al. Collagen-binding peptidoglycans: a biomimetic approach to modulate collagen fibrillogenesis for tissue engineering applications. Tissue Eng., Part A 2009, 15 (10), 2991-9.

Paderi, J. E.; et al. Design of a synthetic collagen-binding peptidoglycan that modulates collagen fibrillogenesis. Biomacromolecules 2008, 9 (9), 2562-6.

Paderi, J. E.; et al. The inhibition of platelet adhesion and activation on collagen during balloon angioplasty by collagen-binding peptidoglycans. Biomaterials 2011, 32 (10), 2516-23.

Portilla-De-Buen, E., et al., Activated clotting time and heparin administration in Sprague-Dawley rats and Syrian golden hamsters. Contemp Top Lab Anim Sci, 2004. 43(2): p. 21-4.

Pukac LA, et al. Antiproliferative effects of novel, nonanticoagulant heparin derivatives on vascular smooth muscle cells in vitro and in vivo. Am J Pathol. 1991;139(6):1501-9.

Quader, M.A., et al. Low molecular weight heparins: current use and indications. J Am Coll Surg, 1998. 187(6): p. 641-58.

Ruoslahti, E., et al., Isolation of a tryptic fragment containing the collagen-binding site of plasma fibronectin. Journal of Biological Chemistry, 1979. 254(13): p. 6054-6059.

Sakiyama-Elbert, S. E. "Incorporation of heparin into biomaterials." Acta biomaterialia 10.4 (2014): 1581-1587.

Sakiyama-Elbert, S. E. et al. Development of fibrin derivatives for controlled release of heparin-binding growth factors. J. Controlled Release 2000, 65 (3), 389-402.

Sistiabudi, R.; et al. Collagen-binding peptide interaction with retinal tissue surfaces. Langmuir 2008, 24 (5), 1591-4.

Sistiabudi, R.; et al. Dip-Pen Nanolithography of Bioactive Peptides on Collagen-Terminated Retinal Membrane. Adv. Mater. 2008, 20 (19), 3678-3681.

Sistiabudi, R.; et al. Modification of native collagen with cell-adhesive peptide to promote RPE cell attachment on Bruch's membrane. Biotechnol. Bioeng. 2009, 102 (6), 1723-9.

Snow AD, et al. Heparin modulates the composition of the extracellular matrix domain surrounding arterial smooth muscle cells. Am J Pathol. 1990;137(2):313-30.

Stuart, K.; et al. Collagen-binding peptidoglycans inhibit MMP mediated collagen degradation and reduce dermal scarring. PLoS One 2011, 6 (7), e22139.

(56) References Cited

OTHER PUBLICATIONS

Szajek, A.Y., et al., The US regulatory and pharmacopeia response to the global heparin contamination crisis. Nat Biotechnol, 2016. 34(6): p. 625-30.

Wissink, M. J. et al. Immobilization of heparin to EDC/NHS-crosslinked collagen. Characterization and in vitro evaluation. Biomaterials 22, 151-163 (2001).

Yang HS, et al. Heparin-conjugated fibrin as an injectable system for sustained delivery of bone morphogenetic protein-2. Tissue Engineering Part A. 2010;16(4):1225-33.

\* cited by examiner

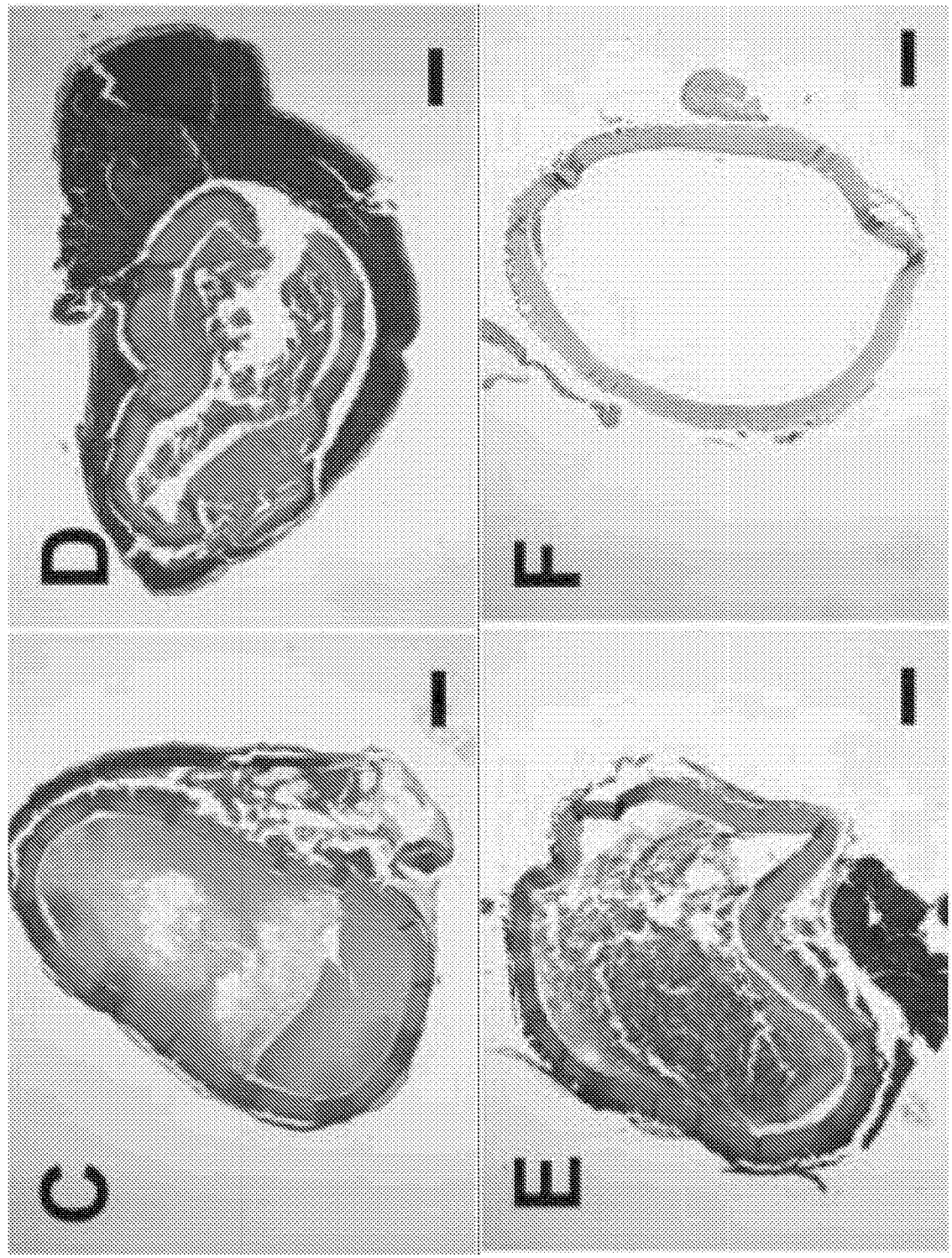
Figure 5C, Figure 5D, Figure 5E, and Figure 5F

SEQUENCE LISTING

```
<160> NUMBER OF SEQ ID NOS: 13

<210> SEQ ID NO 1
<211> LENGTH: 10
<212> TYPE: PRT
<213> ORGANISM: Homo sapiens

<400> SEQUENCE: 1

Cys Gln Asp Ser Glu Thr Arg Thr Phe Tyr
1               5                   10

<210> SEQ ID NO 2
<211> LENGTH: 10
<212> TYPE: PRT
<213> ORGANISM: Artificial
<220> FEATURE:
<223> OTHER INFORMATION: A collagen/gelatinbinding decapeptide derived
      from bovine propolypeptide of von Willebrand factor

<400> SEQUENCE: 2

Trp Arg Glu Pro Ser Phe Cys Ala Leu Ser
1               5                   10

<210> SEQ ID NO 3
<211> LENGTH: 8
<212> TYPE: PRT
<213> ORGANISM: Artificial
<220> FEATURE:
<223> OTHER INFORMATION: Peptide selected by phage display technology,
      that inhibit von Willebrand factor binding to collagen

<400> SEQUENCE: 3

Cys Val Trp Leu Trp Glu Gln Cys
1               5

<210> SEQ ID NO 4
<211> LENGTH: 8
```

```
<212> TYPE: PRT
<213> ORGANISM: Artificial
<220> FEATURE:
<223> OTHER INFORMATION: Peptide selected by phage display technology,
      that inhibit von Willebrand factor binding to collagen

<400> SEQUENCE: 4

Cys Val Trp Leu Trp Glu Asn Cys
1               5

<210> SEQ ID NO 5
<211> LENGTH: 8
<212> TYPE: PRT
<213> ORGANISM: Artificial
<220> FEATURE:
<223> OTHER INFORMATION: A consensus tetra-peptide selected by phage
      display adapts the conformation of a dominant discontinuous
      epitope of a monoclonal anti-VWF antibody that inhibits the in
      vivo VWF-collagen interaction

<400> SEQUENCE: 5

Cys Met Thr Ser Pro Trp Arg Cys
1               5

<210> SEQ ID NO 6
<211> LENGTH: 8
<212> TYPE: PRT
<213> ORGANISM: Artificial
<220> FEATURE:
<223> OTHER INFORMATION: A consensus tetra-peptide selected by phage
      display adapts the conformation of a dominant discontinuous
      epitope of a monoclonal anti-VWF antibody that inhibits the in
      vivo VWF-collagen interaction

<400> SEQUENCE: 6

Cys Arg Thr Ser Pro Trp Arg Cys
1               5

<210> SEQ ID NO 7
<211> LENGTH: 8
<212> TYPE: PRT
<213> ORGANISM: Artificial
<220> FEATURE:
<223> OTHER INFORMATION: A consensus tetra-peptide selected by phage
      display adapts the conformation of a dominant discontinuous
      epitope of a monoclonal anti-VWF antibody that inhibits the in
      vivo VWF-collagen interaction

<400> SEQUENCE: 7

Cys Tyr Arg Ser Pro Trp Arg Cys
1               5

<210> SEQ ID NO 8
<211> LENGTH: 16
<212> TYPE: PRT
<213> ORGANISM: Artificial
<220> FEATURE:
<223> OTHER INFORMATION: Collagen-Targeted MRI Contrast Agent for
      Molecular Imaging of Fibrosis

<400> SEQUENCE: 8

Gly Lys Trp His Cys Thr Thr Lys Phe Pro His His Tyr Cys Leu Tyr
1               5                   10                  15

<210> SEQ ID NO 9
<211> LENGTH: 5
<212> TYPE: PRT
<213> ORGANISM: Artificial
<220> FEATURE:
```

```
<223> OTHER INFORMATION: Cartilage targeting peptide

<400> SEQUENCE: 9

Tyr Arg Gly Arg Leu
1               5

<210> SEQ ID NO 10
<211> LENGTH: 7
<212> TYPE: PRT
<213> ORGANISM: Artificial
<220> FEATURE:
<223> OTHER INFORMATION: High-affinity peptide-based collagen targeting
      peptide isolated from phage display

<400> SEQUENCE: 10

His Val Trp Met Gln Ala Pro
1               5

<210> SEQ ID NO 11
<211> LENGTH: 18
<212> TYPE: PRT
<213> ORGANISM: Artificial
<220> FEATURE:
<223> OTHER INFORMATION: Collagen-targeted peptide

<400> SEQUENCE: 11

Cys Pro Gly Arg Val Met His Gly Leu His Leu Gly Asp Asp Glu Gly
1               5                   10                  15

Pro Cys

<210> SEQ ID NO 12
<211> LENGTH: 7
<212> TYPE: PRT
<213> ORGANISM: Artificial
<220> FEATURE:
<223> OTHER INFORMATION: Vascular targeting peptide

<400> SEQUENCE: 12

Lys Leu Trp Leu Leu Pro Lys
1               5

<210> SEQ ID NO 13
<211> LENGTH: 28
<212> TYPE: PRT
<213> ORGANISM: Artificial
<220> FEATURE:
<223> OTHER INFORMATION: Collagen-binding peptide

<400> SEQUENCE: 13

Gly Leu Arg Ser Lys Ser Lys Lys Phe Arg Arg Pro Asp Ile Gln Tyr
1               5                   10                  15

Pro Asp Ala Thr Asp Glu Asp Ile Thr Ser His Met
                20                  25
```

HEPARIN CONJUGATED TO COLLAGEN-BINDING PEPTIDES FOR TARGETING TO BIOLOGICAL AND SYNTHETIC TISSUES

CROSS-REFERENCE TO RELATED PATENT APPLICATIONS

The present application represents the U.S. National Stage Entry of International Application PCT/US2018/055434, filed Oct. 11, 2018, which claims the benefit of priority under 35 U.S.C. § 119(e) to U.S. Provisional Application 62/570,904, filed on Oct. 11, 2017, the contents of which are incorporated herein by reference in their entireties.

STATEMENT REGARDING FEDERALLY SPONSORED RESEARCH OR DEVELOPMENT

This invention was made with government support under grant numbers R01 EB017129, and K08 DK101757 awarded by the National Institutes of Health. The government has certain rights in the invention.

SEQUENCE LISTING

This application is being filed electronically via EFS-Web and includes an electronically submitted Sequence Listing in .txt format. The .txt file contains a sequence listing entitled "2018-10-08_5369-00524_SEQListing_ST25.txt" created on Oct. 8, 2018 and is 4 Kb in size. The Sequence Listing contained in this .txt file is part of the Specification and is hereby incorporated by reference herein in its entirety.

BACKGROUND

The field of the invention relates to targeted anticoagulants. In particular, the field of the invention relates to heparin conjugates comprising heparin conjugated to a peptide that binds to one or more components of the extracellular cellular matrix (ECM), which ECM-binding peptides may include a collagen-binding peptides (CBPs). The heparin conjugates may be targeted to biological materials and synthetic materials for use as tissue/organ engineering scaffolds, including the ECM of vascular tissue or containing vascular tissue. The heparin conjugates also may be formulated as therapeutics for treating and/or preventing vascular injury in a subject in need thereof.

Heparin is a commonly utilized anticoagulant agent for preventing thrombosis. For example, small vessel thrombosis is one of the major hurdles when using biological materials and synthetic materials as tissue/organ engineering scaffolds. When using decellularized ECM as a tissue/organ engineering scaffold, heparin is often immobilized onto the ECM to provide anticoagulant activity. However, strategies to immobilize heparin onto ECM involve direct chemical crosslinking of heparin to the components of the ECM, which increases the mechanical stiffness and alters the ultrastructure of the ECM. It also is important for biological materials and synthetic materials to maintain their native mechanical properties and structure for their proper function. Extracellular matrix-binding synthetic peptidoglycans also are known in the art. (See, e.g., U.S. Pat. No. 9,200,039; the content of which is incorporated herein by reference in its entirety). In addition, anti-thrombogenic vascular grafts comprising decellularized tissue coated with an anti-thrombogenic coating are known in the art. (See, e.g., U.S. Pat. No. 9,981,066; the content of which is incorporated herein by reference in its entirety). In addition, luminal vessel coatings for arteriovenous fistulas also are known in the art. (See, e.g., U.S. Publication No. 2017/0368192, the content of which is incorporated by reference herein in its entirety). Heparin also has been shown to exhibit anticoagulant activity in the context of synthetic scaffolds. (See, e.g. Place et al., "Synthetic polymer scaffolds for tissue engineering," Chemical Society Reviews, 2009, 38, 1139-1151, 1139-1151; Wang et al., "Functionalization of electrospun poly (ε-caprolactone) scaffold with heparin and vascular endothelial growth factors for potential application as vascular grafts," J. Bioactive and Compatible Polymers, Vol. 28, Issue 2, 2013; and Sakiyama-Elbert, "Incorporation of Heparin into Biomaterials," Acta Biomater. 2014 April; 10(4): 1581-1587; the contents of which are incorporated herein by reference in their entireties). However, better composition and methods for incorporating heparin into biological materials and synthetic materials are desirable.

Heparin also is administered as an anticoagulant agent in treating and preventing vascular injury after vascular surgeries such as percutaneous coronary interventions (PCI). More than 2 million PCIs (with angioplasty with or without stent), are performed annually in the US and Europe. PCIs, in addition to balloon angioplasties of other vessels (e.g. renal, femoral and lower extremity arteries), typically require daily doses of a systemic anticoagulant such as heparin to prevent thrombosis. However, administering daily doses of a systemic anticoagulant increase a subject's risk for life-threatening bleeding. Collagen-binding synthetic peptidoglycans for wound healing are known in the art. (See, e.g., U.S. Publication No. 2012/0100106; the content of which is incorporated by reference in its entirety). However, better anticoagulant therapeutics that are targeted to the site of vessel injury are desirable.

Here, we have prepared heparin conjugates that include heparin conjugated to collagen-binding peptide. Our heparin conjugates can be targeted to collagen-containing biological materials such as the ECM of cellular tissue or ECM within synthetic tissue, in order to reduce thrombosis and/or promote graft assimilation. Our heparin conjugates also may be formulated as therapeutic agents for treating and/or preventing vascular injury.

SUMMARY

Disclosed are compositions and methods that comprise or utilize heparin conjugates. The heparin conjugates include heparin conjugated to a peptide that binds to a component of biological materials and synthetic materials, which may be utilized as tissue/organ engineering scaffolds. Biological materials may include decellularized biological materials such as decellularized ECM, including the ECM comprising or containing vascular tissue.

The disclosed heparin conjugates also bind to biological tissue in situ and may be formulated as therapeutic agents for treating and/or preventing vascular injury. Suitable peptides for preparing the disclosed heparin conjugates may include collagen-binding peptides (CBP), where collagen is a protein of biological origin. Collagen may be found in situ, within a tissue, or as part of explanted material or synthetic material.

The disclosed heparin conjugates may comprise heparin conjugated to a peptide that binds to one or more components of the extracellular matrix (ECM), where the heparin conjugate binds to one or more components of the ECM. In particular, the ECM-binding peptide may be a collagen-binding peptide (CBP), where the ECM-binding peptide is conjugated directly or indirectly to heparin via an amide bond formed between a carboxyl group of heparin and an N-terminal amino group of the ECM-binding peptide or via an amide bond formed between a carboxyl group of heparin and an N-terminal amino group of a linking peptide that links the ECM-binding peptide to heparin.

The disclosed heparin conjugates may include heparin conjugated, for example, via an amide linkage formed between a carboxyl group of heparin and an amino group of one or more CBPs (e.g., an N-terminal amino group) or an amino group of one or more "linking peptides" (e.g., an N-terminal amino group), which link the CBPs to the heparin. The disclosed heparin conjugates may be prepared by methods that include activating one or more carboxyl groups of heparin and reacting the one or more activated carboxyl groups with an amino group (e.g., an N-terminal amino group) of one or more CPBs or one or more linking peptides, which link the CBPs to the heparin.

Also disclosed are methods of preparing biological materials and synthetic materials that comprise or utilize the disclosed heparin conjugates, including decellularized ECMs from vascular tissue that comprise or utilize the disclosed heparin conjugates. In the disclosed methods, biological materials and synthetic materials may be prepared by treating the biological materials and synthetic materials with the disclosed heparin conjugates, where the disclosed heparin conjugates bind to a protein of the biological materials and synthetic materials such as collagen present in the biological materials and synthetic materials and may impart anticoagulant properties to the biological materials and synthetic materials.

The biological materials and synthetic materials thus treated may be utilized as a graft for tissue repair, replacement and/or engineering. Optionally, cells such as but not limited to endothelial cells and smooth muscle cells may be grown on decellularized biological materials and synthetic materials to prepare a graft prior to implanting the graft into a subject. A graft may be a vascular tissue, may contain vascular tissue, or require ingrowth of vascular tissue for survival within a subject.

Also disclosed are methods of treating vascular injury in a subject in need thereof. A subject in need thereof may include a subject having or at risk for developing a vascular injury or condition, including a subject undergoing or having undergone vascular surgery such as an angioplasty or a vascular anastomosis.

DETAILED DESCRIPTION

Figure 1A:
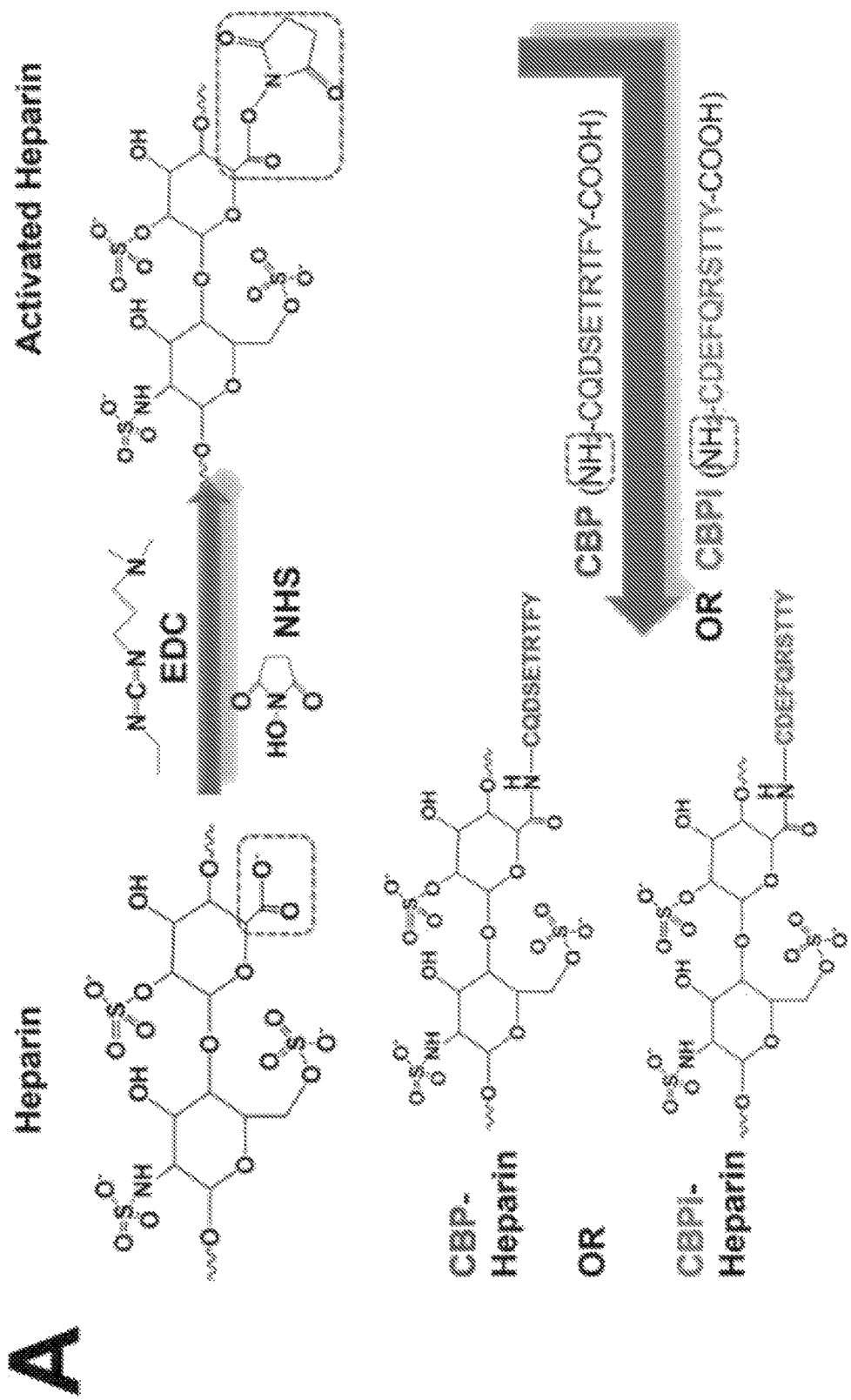
FIG. 1. Schematic representation of (A) heparin conjugated with the collagen binding (CBP) or nonbinding (CBPi) peptide, and (B) ECM-modified by CBP-heparin, but not CBPi-heparin or unfractionated heparin alone.

The present invention is described herein using several definitions, as set forth below and throughout the application.

Unless defined otherwise, all technical and scientific terms used herein have the same meaning as commonly understood by one of skill in the art to which the invention pertains. All definitions, as defined and used herein, should be understood to control over dictionary definitions, definitions in documents incorporated by reference, and/or ordinary meanings of the defined terms.

Unless otherwise specified or indicated by context, the terms "a", "an", and "the" should be interpreted to mean "one or more." For example, "heparin" should be interpreted to mean "one or more heparin molecules" and "a collagen-binding peptide (CBP)" should be interpreted to mean "one or more collagen-binding peptides (CBPs)."

As used herein, "about," "approximately," "substantially," and "significantly" will be understood by persons of ordinary skill in the art and will vary to some extent on the context in which they are used. If there are uses of these terms which are not clear to persons of ordinary skill in the art given the context in which they are used, "about" and "approximately" should be interpreted to mean plus or minus ≤10% of the particular term and "substantially" and "significantly" should be interpreted to mean plus or minus >10% of the particular term.

As used herein, the terms "include" and "including" should be interpreted to have the same meaning as the terms "comprise" and "comprising" in that these latter terms are "open" transitional terms that do not limit claims only to the recited elements succeeding these transitional terms. The term "consisting of," while encompassed by the term "comprising," should be interpreted as a "closed" transitional term that limits claims only to the recited elements succeeding this transitional term. The term "consisting essentially of," while encompassed by the term "comprising," should be interpreted as a "partially closed" transitional term which permits additional elements succeeding this transitional term, but only if those additional elements do not materially affect the basic and novel characteristics of the claim.

A range includes each individual member. Thus, for example, a group having 1-3 members refers to groups having 1, 2, or 3 members.

It should also be understood that, unless clearly indicated to the contrary, in any methods claimed herein that include more than one step or act, the order of the steps or acts of the method is not necessarily limited to the order in which the steps or acts of the method are recited.

The modal verb "may" refers to the preferred use or selection of one or more options or choices among the several described embodiments or features contained within the same. Where no options or choices are disclosed regarding a particular embodiment or feature contained in the same, the modal verb "may" refers to an affirmative act regarding how to make or use an aspect of a described embodiment or feature contained in the same, or a definitive decision to use a specific skill regarding a described embodiment or feature contained in the same. In this latter context, the modal verb "may" has the same meaning and connotation as the auxiliary verb "can."

As used herein, a "subject" may be interchangeable with "patient" or "individual" and means an animal, which may be a human or non-human animal, in need of treatment.

A "subject in need" may include a subject having a disease, disorder, or condition that can be treated by administering a graft to the subject, for example, a graft comprising a biological material or synthetic material or a graft prepared from biological material or synthetic material.

A "subject in need" may include a subject having a disease, disorder, or injury that can be treated and/or prevented by administering to the subject an anticoagulant agent. A subject in need may include a subject having or at risk for developing a vascular disease, disorder, or injury. A subject in need may include a subject undergoing or having undergone vascular surgery. Vascular surgery may include angioplasty with or without insertion of a stent. Vascular surgery may also include performing an anastomosis, which may comprise joining two vessels together or joining together a vessel and a vascular graft. A subject in need may include a subject undergoing or having undergone a percutaneous coronary intervention. A subject in need may include a subject undergoing or having undergone angioplasties of other vessels (e.g. renal, femoral and lower extremity arteries). A subject in need may include a subject having a disease, disorder, or injure that requires daily doses of a systemic anticoagulant such as heparin to prevent thrombosis. A subject in need may include a subject having or at risk for developing renal failure, for example, subjects who have poorly functional or non-functional dialysis access fistulas who must undergo interventional, vascular procedures that cause further iatrogenic injury to the fistula by angioplasty with or without stent placement. A subject in need may include a subject exhibiting hypertension or at risk for developing hypertension.

As used herein, "biological material" may include ECM. A "graft" may include biological material or synthetic material made from or containing ECM. Biological material may include decellularized biological materials (e.g., decellularized ECM). "Synthetic material" may include material that is not of biological origin and/or is not naturally occurring. "Synthetic material" may include material of biological origin which has been modified so as not to be naturally occurring, such as coating or impregnating the synthetic material with biological material. "Synthetic material" may include polymeric scaffolds suitable for use in tissue engineering applications. (See Dhandayuthapani, et al., "Polymeric Scaffolds in Tissue Engineering Application: A Review," International Journal of Polymer Science, Volume 2011, Article ID 290602, 19 pages; the content of which is incorporated herein by reference in its entirety).

Heparin and Heparin Conjugates

The disclosed compositions and methods related to heparin conjugates. Heparin refers to an anticoagulant produced by basophils and mast cells. Native heparin is a polymer of heparin disaccharide monomers and has a molecular weight ranging from 3-30 kDa. The average molecular weight of most commercial heparin preparations is 12-15 kDa. A so-called "low molecular weight" heparin is a heparin derivative having an average molecular weight of less than about 8 kDa and/or a heparin derivative in which all chains of the heparin have a molecular weight less than 8 kDa.

Heparin is a polymer of disaccharide "monomer" units largely formed from GlcA=β-D-glucuronic acid; IdoA=α-L-iduronic acid; IdoA(2S)=2-O-sulfo-α-L-iduronic acid; GlcNAc=2-deoxy-2-acetamido-α-D-glucopyranosyl; GlcNS=2-deoxy-2-sulfamido-α-D-glucopyranosyl; GlcNS (6S)=2-deoxy-2-sulfamido-α-D-glucopyranosyl-6-0-sulfate; GlcNS (3 S, 6S)=3-O-sulfated glucosamine; and GlcNH3+=glucosamine with a free amine group. The most common disaccharide unit comprises 2-O-sulfated iduronic acid and 6-O-sulfated, N-sulfated glucosamine (IdoA(2S)-GlcNS(6S)), which makes up ~85% of heparins from beef lung and ~75% of those from porcine intestinal mucosa. The IdoA(2S)-GlcNS(6S) disaccharide of heparin may be represented as follows:

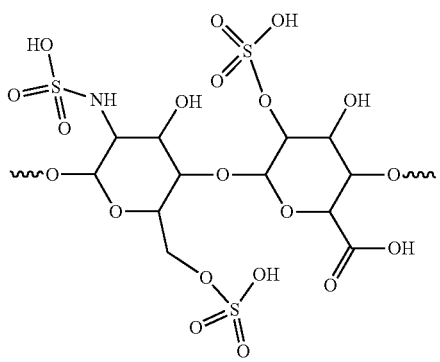

The IdoA(2S) unit of the IdoA(2S)-GlcNS(6S) disaccharide has a free carboxyl comprising its 6-carbon, which may be utilized for conjugated heparin to collagen-binding peptide as contemplated herein, for example as follows:

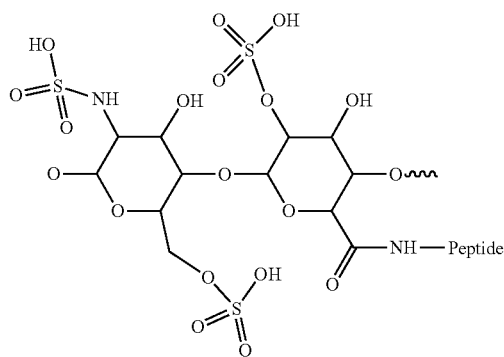

As utilized herein, the term "heparin" should be broadly interpreted to include heparin polymers and heparin disaccharide unit monomers, unless context indicates otherwise.

Heparin exhibits anticoagulant activity by binding to antithrombin and causing a conformational change in antithrombin that results in its activation. The activated antithrombin then inactivates thrombin, factor Xa and other proteases, whose activities are required for clotting. The anticoagulant activity of heparin (i.e., a "unit" heparin) and/or the anticoagulant activity of the heparin conjugates disclosed herein may be measured using assays known in the art and disclosed herein. One Howell unit of heparin is an amount approximately equivalent to 0.002 mg of pure heparin, which is the quantity required to keep 1 ml of cat's blood fluid for 24 hours at 0° C. The anti-Factor Xa activity of heparin also may be measured using assays known in the art and disclosed herein.

The heparin conjugates disclosed herein may be utilized for incorporating heparin into biomaterials and synthetic materials. Methods for incorporating heparin into biomaterials and synthetic materials are know in the art. (See, e.g., Sakiyama-Elbert, "Incorporation of Heparin into Biomaterials," Acta Biomater. 2014 April; 10(4): 1581-1587; the content of which is incorporated herein by reference in its entirety).

Peptide, Polypeptides, and Proteins

Reference also is made herein to peptides, polypeptides, proteins and compositions comprising peptides, polypeptides, and proteins. As used herein, a polypeptide and/or protein is defined as a polymer of amino acids, typically of length ≥100 amino acids (Garrett & Grisham, Biochemistry, $2^{nd}$ edition, 1999, Brooks/Cole, 110). A peptide is defined as a short polymer of amino acids, of a length typically of 20 or less amino acids, and more typically of a length of 12 or less amino acids (Garrett & Grisham, Biochemistry, $2^{nd}$ edition, 1999, Brooks/Cole, 110).

As disclosed herein, exemplary peptides, polypeptides, proteins may comprise, consist essentially of, or consist of any reference amino acid sequence disclosed herein, or variants of the peptides, polypeptides, and proteins may comprise, consist essentially of, or consist of an amino acid sequence having at least about 80%, 90%, 95%, 96%, 97%, 98%, or 99% sequence identity to any amino acid sequence disclosed herein. Variant peptides, polypeptides, and proteins may include peptides, polypeptides, and proteins having one or more amino acid substitutions, deletions, additions and/or amino acid insertions relative to a reference peptide, polypeptide, or protein. Also disclosed are nucleic acid molecules that encode the disclosed peptides, polypeptides, and proteins (e.g., polynucleotides that encode any of the peptides, polypeptides, and proteins disclosed herein and variants thereof).

The term "amino acid," includes but is not limited to amino acids contained in the group consisting of alanine (Ala or A), cysteine (Cys or C), aspartic acid (Asp or D), glutamic acid (Glu or E), phenylalanine (Phe or F), glycine (Gly or G), histidine (His or H), isoleucine (Ile or I), lysine (Lys or K), leucine (Leu or L), methionine (Met or M), asparagine (Asn or N), proline (Pro or P), glutamine (Gln or Q), arginine (Arg or R), serine (Ser or S), threonine (Thr or T), valine (Val or V), tryptophan (Trp or W), and tyrosine (Tyr or Y) residues. The term "amino acid residue" also may include amino acid residues contained in the group consisting of homocysteine, 2-Aminoadipic acid, N-Ethylasparagine, 3-Aminoadipic acid, Hydroxylysine, β-alanine, β-Amino-propionic acid, allo-Hydroxylysine acid, 2-Aminobutyric acid, 3-Hydroxyproline, 4-Aminobutyric acid, 4-Hydroxyproline, piperidinic acid, 6-Aminocaproic acid, Isodemosine, 2-Aminoheptanoic acid, allo-Isoleucine, 2-Aminoisobutyric acid, N-Methylglycine, sarcosine, 3-Aminoisobutyric acid, N-Methylisoleucine, 2-Aminopimelic acid, 6-N-Methyllysine, 2,4-Diaminobutyric acid, N-Methylvaline, Desmosine, Norvaline, 2,2'-Diaminopimelic acid, Norleucine, 2,3-Diaminopropionic acid, Ornithine, and N-Ethylglycine. Typically, the amide linkages of the peptides are formed from an amino group of the backbone of one amino acid and a carboxyl group of the backbone of another amino acid.

The amino acid sequences contemplated herein may include conservative amino acid substitutions relative to a reference amino acid sequence. For example, a variant peptides, polypeptides, and proteins as contemplated herein may include conservative amino acid substitutions relative to an amino acid sequence of a reference peptide, polypeptide, or protein.

"Conservative amino acid substitutions" are those substitutions that are predicted to interfere least with the properties of the reference peptide, polypeptide, or protein. In other words, conservative amino acid substitutions substantially conserve the structure and the function of the reference peptide, polypeptide, or protein. The following table provides a list of exemplary conservative amino acid substitutions.

| Table of Conservative Amino Acid Substitutions | |
|---|---|
| Original Residue | Conservative Substitutions |
| Ala | Gly, Ser |
| Arg | His, Lys |
| Asn | Asp, Gln, His |
| Asp | Asn, Glu |
| Cys | Ala, Ser |
| Gln | Asn, Glu, His |
| Glu | Asp, Gln, His |
| Gly | Ala |
| His | Asn, Arg, Gln, Glu |
| Ile | Leu, Val |
| Leu | Ile, Val |
| Lys | Arg, Gln, Glu |
| Met | Leu, Ile |
| Phe | His, Met, Leu, Trp, Tyr |
| Ser | Cys, Thr |
| Thr | Ser, Val |
| Trp | Phe, Tyr |
| Tyr | His, Phe, Trp |
| Val | Ile, Leu, Thr |

"Non-conservative amino acid substitutions" are those substitutions that are predicted to interfere most with the properties of the reference peptide, polypeptide, or protein. For example, a non-conservative amino acid substitution might replace a basic amino acid at physiological pH such as Arg, His, or Lys, with a non-basic or acidic amino acid at physiological pH such as Asp or Glu. A non-conservative amino acid substitution might replace a non-polar amino acid at physiological pH such as Ala, Gly, Ile, Leu, Phe, or Val, with a polar amino acid at physiological pH such as Arg, Asp, Glu, His, or Lys.

The peptides, polypeptides, and proteins disclosed herein may be modified to include non-amino acid moieties. Modifications may include but are not limited to carboxylation (e.g., N-terminal carboxylation via addition of a di-carboxylic acid having 4-7 straight-chain or branched carbon atoms, such as glutaric acid, succinic acid, adipic acid, and 4,4-dimethylglutaric acid), amidation (e.g., C-terminal amidation via addition of an amide or substituted amide such as alkylamide or dialkylamide), PEGylation (e.g., N-terminal or C-terminal PEGylation via additional of polyethylene glycol), acylation (e.g., O-acylation (esters), N-acylation (amides), S-acylation (thioesters)), acetylation (e.g., the addition of an acetyl group, either at the N-terminus of the protein or at lysine residues), formylation lipoylation (e.g., attachment of a lipoate, a C8 functional group), myristoylation (e.g., attachment of myristate, a C14 saturated acid), palmitoylation (e.g., attachment of palmitate, a C16 saturated acid), alkylation (e.g., the addition of an alkyl group, such as an methyl at a lysine or arginine residue), isoprenylation or prenylation (e.g., the addition of an isoprenoid group such as farnesol or geranylgeraniol), amidation at C-terminus, glycosylation (e.g., the addition of a glycosyl group to either asparagine, hydroxylysine, serine, or threonine, resulting in a glycoprotein). Distinct from glycation, which is regarded as a nonenzymatic attachment of sugars, polysialylation (e.g., the addition of polysialic acid), glypiation (e.g., glycosylphosphatidylinositol (GPI) anchor formation, hydroxylation, iodination (e.g., of thyroid hormones), and phosphorylation (e.g., the addition of a phosphate group, usually to serine, tyrosine, threonine or histidine).

A "variant" of a reference polypeptide sequence may include a deletion relative to the reference polypeptide sequence. A "deletion" refers to a change in a reference amino acid sequence (e.g., any of SEQ ID NOs:1-14) that results in the absence of one or more amino acid residues. A deletion removes at least 1, 2, 3, 4, 5, 10, 11, 12, 13, 14, 15, 16, 17, 18, 19, 20, 50, 100, or 200 amino acids residues or a range of amino acid residues bounded by any of these values (e.g., a deletion of 5-10 amino acids). A deletion may include an internal deletion or a terminal deletion (e.g., an N-terminal truncation or a C-terminal truncation of a reference polypeptide).

A "variant" of a reference polypeptide sequence may include an insertion or addition relative to the reference polypeptide sequence. The words "insertion" and "addition" refer to changes in an amino acid sequence resulting in the addition of one or more amino acid residues. An insertion or addition may refer to 1, 2, 3, 4, 5, 6, 7, 8, 9, 10, 11, 12, 13, 14, 15, 16, 17, 18, 19, 20, 30, 40, 50, 60, 70, 80, 90, 100, 150, or 200 amino acid residues or a range of amino acid residues bounded by any of these values (e.g., an insertion or addition of 5-10 amino acids).

A "variant" of a reference polypeptide sequence may include a fusion polypeptide comprising the reference polypeptide. A "fusion polypeptide" refers to a polypeptide comprising at the N-terminus, the C-terminus, or at both termini of its amino acid sequence a heterologous amino acid sequence, for example, a heterologous amino acid sequence that extends the half-life of the fusion polypeptide in serum.

A "variant" of a reference polypeptide sequence may include a fragment of the reference polypeptide sequence. A "fragment" is a portion of an amino acid sequence which is identical in sequence to but shorter in length than a reference sequence (e.g., any of SEQ ID NOs:1-14). A fragment may comprise up to the entire length of the reference sequence, minus at least one amino acid residue. For example, a fragment may comprise from 5 to 1000 contiguous amino acid residues of a reference polypeptide. In some embodiments, a fragment may comprise at least 5, 6, 7, 8, 9 10, 11, 12, 13, 14, 15, 16, 17, 18, 19, 20, 25, 30, 40, 50, 60, 70, 80, 90, 100, 150, 250, or 500 contiguous amino acid residues of a reference polypeptide; or a fragment may comprise no more than 5, 6, 7, 8, 9 10, 11, 12, 13, 14, 15, 16, 17, 18, 19, 20, 25, 30, 40, 50, 60, 70, 80, 90, 100, 150, 250, or 500 contiguous amino acid residues of a reference polypeptide; or a fragment may comprise a range of contiguous amino acid residues of a reference polypeptide bounded by any of these values (e.g., 40-80 contiguous amino acid residues). Fragments may be preferentially selected from certain regions of a molecule. The term "at least a fragment" encompasses the full length polypeptide. "Homology" refers to sequence similarity or, interchangeably, sequence identity, between two or more polypeptide sequences. Homology, sequence similarity, and percentage sequence identity may be determined using methods in the art and described herein.

The phrases "percent identity" and "% identity," as applied to polypeptide sequences, refer to the percentage of residue matches between at least two polypeptide sequences aligned using a standardized algorithm. Methods of polypeptide sequence alignment are well-known. Some alignment methods take into account conservative amino acid substitutions. Such conservative substitutions, explained in more detail above, generally preserve the charge and hydrophobicity at the site of substitution, thus preserving the structure (and therefore function) of the polypeptide. Percent identity for amino acid sequences may be determined as understood in the art. (See, e.g., U.S. Pat. No. 7,396,664, which is incorporated herein by reference in its entirety). A suite of commonly used and freely available sequence comparison algorithms is provided by the National Center for Biotechnology Information (NCBI) Basic Local Alignment Search Tool (BLAST) (Altschul, S. F. et al. (1990) J. Mol. Biol. 215:403 410), which is available from several sources, including the NCBI, Bethesda, Md., at its website. The BLAST software suite includes various sequence analysis programs including "blastp," that is used to align a known amino acid sequence with other amino acids sequences from a variety of databases.

Percent identity may be measured over the length of an entire defined polypeptide sequence, for example, as defined by a particular SEQ ID number, or may be measured over a shorter length, for example, over the length of a fragment taken from a larger, defined polypeptide sequence, for instance, a fragment of at least 5, of at least 10, at least 15, at least 20, at least 25, at least 30, at least 40, at least 50, at least 100, at least 150, at least 200, at least 250, at least 300, at least 350, at least 400, at least 450, at least 500, at least 550, at least 600, at least 650, or at least 700 contiguous amino acid residues; or a fragment of no more than 5, 10, 15, 20, 25 30, 40, 50, 100, 150, 200, 250, 300, 350, 400, 450, 500, 550, 600, 650, or 700 amino acid residues; or over a range bounded by any of these values (e.g., a range of 5-20 amino acid residues) Such lengths are exemplary only, and it is understood that any fragment length supported by the sequences shown herein, in the tables, figures or Sequence Listing, may be used to describe a length over which percentage identity may be measured.

In some embodiments, a "variant" of a particular polypeptide sequence may be defined as a polypeptide sequence having at least 20% sequence identity to the particular polypeptide sequence over a certain length of one of the polypeptide sequences using blastp with the "BLAST 2 Sequences" tool available at the National Center for Biotechnology Information's website. (See Tatiana A. Tatusova, Thomas L. Madden (1999), "Blast 2 sequences—a new tool for comparing protein and nucleotide sequences", FEMS Microbiol Lett. 174:247-250). Such a pair of polypeptides may show, for example, at least 20%, at least 30%, at least 40%, at least 50%, at least 60%, at least 70%, at least 80%, at least 90%, at least 91%, at least 92%, at least 93%, at least 94%, at least 95%, at least 96%, at least 97%, at least 98%, or at least 99% or greater sequence identity over a certain defined length of one of the polypeptides, or range of percentage identity bounded by any of these values (e.g., range of percentage identity of 80-99%).

A variant polypeptide may have substantially the same functional activity as a reference polypeptide. For example, a variant polypeptide of a reference polypeptide that binds to collagen may exhibit or more biological activities associated with the reference polypeptide, for example, collagen-binding activity.

Collagen-Binding Peptides

The disclosed heparin conjugates typically include heparin conjugated to a peptide that targets the heparin conjugate to the extracellular matrix. Such conjugating peptides include, but are not limited to, collagen-binding peptides (CBPs). CBPs have been disclosed in the art. (See, e.g., Yamada, et al. Dualistic Nature of Adhesive Protein Function—Fibronectin and Its Biologically-Active Peptide-Fragments Can Autoinhibit Fibronectin Function. J. Cell Biol. 1984, 99 (1), 29-36 (disclosing the peptide CQDSETRTFY (SEQ ID NO:1)); Boucaut, J. C et al. Biologically-Active Synthetic Peptides as Probes of Embryonic-Development—a Competitive Peptide Inhibitor of Fibronectin Function Inhibits Gastrulation in Amphibian Embryos and Neural Crest Cell-Migration in Avian Embryos. J. Cell Biol. 1984, 99 (5), 1822-1830 (disclosing the peptide CQDSETRTFY (SEQ ID NO:1)); Takagi et al. (1992) A collagen/gelatin binding decapeptide derived from bovine propolypeptide of von Willebrand factor. *Biochemistry.* 31(36), 8530-8534 (disclosing the peptide WREPSFCALS (SEQ ID NO: 2)); Depraetere et al. (1998) Identification of peptides, selected by phage display technology, that inhibit von Willebrand factor binding to collagen. Blood. 92, 4207-4211 (disclosing the peptide CVWLWEQC (SEQ ID NO: 3) and the peptide CVWLWENC (SEQ ID NO: 4)); Vanhoorelbeke et al. (2003) A consensus tetra-peptide selected by phage display adapts the conformation of a dominant discontinuous epitope of a monoclonal anti-VWF antibody that inhibits the in vivo VWF-collagen interaction. *J Biol Chem.* 278, 37815-37821 (disclosing the peptide CMTSPWRC (SEQ ID NO: 5), the peptide CRTSPWRC (SEQ ID NO: 6); and the peptide CYRSPWRC (SEQ ID N: 7)); Caravan et al. (2007) Collagen-Targeted MRI Contrast Agent for Molecular Imaging of Fibrosis. Angew. Chem. 46(43), 8171-8173 (disclosing the peptide GKWHCTTKFPHHYCLY (SEQ ID NO:8)); Rothenfluh et al. (2008) Biofunctional polymer nanoparticles for intraarticular targeting and retention in cartilage. *Nature Materials.* 7, 248-254 (disclosing the peptide YRGRL (SEQ ID NO: 9)); Helms et al. (2009) High-Affinity Peptide-Based Collagen Targeting Using Synthetic Phage Mimics: From Phage Display to Dendrimer Display. J. Am. Chem. Soc. 131(33), 11683-11685 (disclosing the peptide HVWMQAP (SEQ ID NO:10)); Muzzard et al. (2009) Non-invasive molecular imaging of fibrosis using a collagen-targeted peptidomimetic of the platelet collagen receptor glycoprotein VI. *PLoS one.* 4 (e5585) 1-10 (disclosing the peptide CPGRVMEIGLIILGDDEGPC (SEQ ID NO: 10); Chan et al. (2010) Spatiotemporal controlled delivery of nanoparticles to injured vasculature. *Proc Natl Acad Sci U.S.A.* 107, 2213-2218 2010 (disclosing the peptide KLWLLPK (SEQ ID NO 12)); Lee et al. (2007) Assembly of collagen-binding peptide with collagen as a bioactive scaffold for osteogenesis in vitro and in vivo. Biomaterials. October; 28(29):4257-67 (disclosing the peptide GLRSK-SKKFRRPDIQYPDATDEDITSHM (SEQ ID NO:13)); the contents of which are incorporated herein by reference in their entireties).

In addition, structural requirement for CBPs also have been studied and reported in the art. (See, e.g., Abd-Elgaliel et al. (2013), Exploring the Structural Requirement of Collagen-Binding Peptides. Biopoplymers April 100(2): 167-173; Svensson et al., (2001) Collagen Binding Proteins. Osteoarthritis and Cartilage 9, Supplement A, S23-S28; and U.S. Published Application No. 20161016210; the contents of which are incorporated herein by reference in their entireties).

Extracellular Matrix

The disclosed heparin-conjugates may be used to modify the extracellular matrix (ECM), for example, in order to impart anticoagulant properties to the ECM or influence how cells grow on ECM. Heparin-modified ECM is disclosed in the art. (See, e.g., International Publication No. WO 2006/044512, the content of which is incorporated herein by reference in its entirety).

As used herein, the term "extracellular matrix," abbreviated "ECM," refers to the complex structural material secreted by cells in mammalian tissues (e.g., particularly cells of connective tissue, for instance such cells as fibroblasts, osteoblasts, chondrocytes, epithelial cells, smooth muscle cells, adipocytes, mesenchymal cells, etc.) which surrounds and supports the cells in vivo. Typically, the ECM is composed of fibers embedded in what is commonly referred to as 'ground substance.' ECM include proteins in the fibers as structural proteins ("ECM fibers" or "ECM fiber proteins"), such as collagen and/or elastin. Particularly suitable collagens are fibril-forming collagens, such as type I collagen, type II collagen, type III collagen, type IV collagen or type X collagen. ECM also includes proteins in the 'ground substance' of ECM ("ECM ground" or "ECM ground proteins"). Additional ECM proteins may include, for example, glycoproteins, such as laminin, entactin, tenascin, fibrillin, or fibronectin, for improving structural integrity of the network and for the attachment of cells to the ECM; osteocalcin (Gla protein), as a protein that binds calcium during mineralization; osteonectin, which serves a bridging function between collagen and mineral component; and sialoproteins, such as bone sialoprotein (BSP), osteopontin (OPN), dentin matrix protein-1 (DMP1), dentin sialophosphoprotein (DSPP) and matrix extracellular phosphoglycoprotein (MEPE). ECM refers both to the material in vivo, as well as to the material in isolated form, separated from the cells that produced it ("decellularized ECM" ("dECM"))).

ECMs for clinical applications are derived from organs such as the small intestine, urinary bladder or skin (Reing J., et al. 2009, Tissue Engineering, Vol. 15: 605-614.; Badylak S F. 2004. Transplant Immunology 12: 367-377; herein incorporated by reference in their entireties), from allogeneic (human cadavers) or xenogeneic sources (porcine, bovine or equine small intestine submucosa, dermis and pericardium). Both cellular and acellular forms of ECM scaffolds have been used for tissue engineering applications.

In some embodiments, in order to be amendable for tissue regeneration or repair applications, the ECM is devoid of cellular components. In some embodiments, the ECM is devoid of cellular components in certain regions as to provide access to the disclosed heparin-conjugates. In some embodiments, the disclosed methods comprise decellularizing the extracellular matrix. As used herein the phrase "decellularizing the ECM" or "decellularized ECM" refers to removal of cells, which may be either completely or partially, from the ECM or a portion of ECM. According to some embodiments, the isolated ECM is decellularized, either completely or partly. Decellularized ECM may refer to ECM that is either partially or completely devoid of any cellular components. The phrase "devoid of any cellular components" as used herein refers to being more than about 80%, e.g., more than 81%, 82%, 83%, 84%, 85%, 86%, 87%, 88%, 89%, 90%, 91%, 92%, 93%, 93%, 94%, 95%, 96%, 97%, 98%, 99%, e.g., 100% devoid of the cellular components present in the cell culture which comprises the ECM prior to the decellularization process. The phrase "partially" represents a region or subsection of ECM that may be devoid of cellular components such as to enable access (e.g. binding) of disclosed heparin-binding conjugates to the ECM. As used herein, the phrase "cellular components" refers to cell membrane components or intracellular components which make up the cell. Examples of cell components include cell structures (e.g., organelles) or molecules comprised in same. Examples of such include, but are not limited to, cell nuclei, nucleic acids, residual nucleic acids (e.g., fragmented nucleic acid sequences), cell membranes and/or residual cell membranes (e.g., fragmented membranes) which are present in cells of the tissue.

In some embodiments, it may be advantageous to remove cellular components of a tissue (e.g. "decellularize") due to disease, or as a result of treatment for a medical condition. As an example, tissues may be decellularized to create a tissue graft to treat a medical condition. As a further example, cells covering an ECM may be lost (e.g. "decellularized") when vessels are joined together (e.g. an anastomosis) or when tissues suffer an abrasion or injury as a result of angioplasty with or without stent placement.

In some embodiments, by whatever method the ECM is decellularized, the decellularization process is performed such that the cellular components are removed while the ECM is substantially unharmed (e.g. in its native form), and exhibits the same structural and mechanical properties as the ECM prior to the decellularization process. In some embodiments, the ECM may be coated, impregnated or incorporated into synthetic tissue. Decellularization of the ECM may be performed by various methods known in the art. For example, decellularization can be performed by physical treatment or a combination thereof, such as but not limited to lyophilization, freeze and thaw cycling and DNase treatment, essentially as described in Ngangan A V and McDevitt T C (2009, Biomaterials 30: 1143-1149 which is fully incorporated herein by reference in its entirety); decellularization may be performed by physical or mechanical abrasion of cellularized tissue that results in loss of cells, such as but not limited to, angioplasty with or without stent placement or creation of a vascular anastomosis; decellularization may be performed by Peracetic acid, Sodium dodecyl sulfate, Triton-X100 and DNase essentially as described in Nair R. et al. (2008, J. Biomater. Sci. Polymer Edn. 19: 801-819, which is fully incorporated herein by reference in its entirety); decellularization may be performed by treatment with distilled water (e.g., Aqua dest) for 24 hours, 1% SDS for 24 hours, distilled water for 24 hours and 70% Ethanol for 24 hours, followed by washes with PBS, essentially as described in Tischer T. et al. (2007, Arch Orthop Trauma Surg. 127:735-741, which is fully incorporated herein by reference in its entirety); decellularization may be performed by washes in hypertonic 1.1% NaCl-0.02% ethylenediaminetetraacetic acid (EDTA; Sigma, St. Louis, Mo.) for 2 hours and then in hypotonic 0.7% NaCl-0.02% EDTA for 2 hours, followed by two 24 hours cycles of enzymatic digestion using 0.05% trypsin (Sigma)-0.02% EDTA in PBS at pH 7.4 and at 37° C., supplemented with Pen-Strep and Fungizone, followed by wash(es) in detergent solution of 1% Triton-X-100 (polyethylene octylphenyl ether) and 0.1% ammonium hydroxide in PBS for four consecutive 48 hours cycles, and extensive washes in sterile saline, immersion in 70% ethanol overnight, and washes in sterile water, and lyophilization, essentially as described in Eitan Y. et al. (2010, Tissue engineering part C Methods. 16(4):671-83; which is fully incorporated herein by reference in its entirety); decellularization can be performed by combination of physical and chemical treatments as~sonication, agitation, freezing and thawing, and then several detergent washes, essentially as described in Badylak S F et al. 2009 (ActaBiomaterialia, 5: 1-13, which is fully incorporated herein by reference in its entirety).

Descriptive Embodiments

The following embodiments are descriptive and should not be interpreted to limit the scope of the claimed subject matter.

In some embodiments, the disclosed subject matter relates to a heparin conjugate comprising heparin conjugated to a peptide that binds to a protein of the extracellular matrix of cellular tissue such as a collagen-binding peptide (CBP). Optionally, the heparin of the heparin conjugate may be a low molecular weight heparin (e.g., heparin having an average molecule weight of less than about 8 kDa).

In the disclosed heparin conjugates, the binding peptide that binds to one or more components of the extracellular matrix (i.e., "ECM-binding peptide") may be directly conjugated to heparin (e.g., via an amide bond formed between a carboxyl group of heparin and an amino group of the binding peptide), or the binding peptide may be indirectly conjugated to heparin via a "linking peptide" (e.g., where the linking peptide is directly conjugated to heparin, for example, via an amide bond formed between a carboxyl group of heparin and an amino group of the linking peptide and the linking peptide links the binding peptide to heparin). In some embodiments, the heparin conjugate may comprise multiple copies of the binding peptide (e.g., multiple copies of the binding peptide linked in tandem via linking peptides) conjugated directly or indirectly to heparin via multiple copies of the linking peptide (e.g., multiple copies of the binding peptide linked in a branched structure via the linking peptide).

Preferably, the disclosed heparin conjugates bind to the extracellular matrix (ECM). In some embodiments, the disclosed heparin conjugates bind to one or more components of the ECM.

Preferably, the disclosed heparin conjugates bind to one or more collagen types. Preferably, the heparin conjugates bind to collagen I and/or collagen IV.

Preferably, the disclosed heparin conjugates bind to antithrombin and/or thrombin.

Preferably, the disclosed heparin conjugates bind to a heparin-binding growth factor such as vascular endothelial factor.

Preferably, the disclosed heparin conjugates display anticoagulant activity, such as anti-Factor Xa activity. Preferably, the disclosed heparin conjugates have an anti-Factor Xa activity greater than about 0.5, 1, 5, 10, 20, 30, 40, 50, 100, 150, or 200 U/mg or the heparin conjugates completely abrogate Factor Xa activity.

The disclosed heparin conjugates comprise heparin conjugated to a peptide, such as a collagen-binding peptide. The heparin and the peptide may be conjugated directly or via a linking peptide. In some embodiments, the heparin and the peptide are conjugated via an amide linkage formed between a carboxyl group of the heparin and the N-terminal amino group of the peptide.

The disclosed heparin conjugates comprise a peptide such as a collagen-binding peptide. In some embodiments, the peptide is relatively short and comprises no more than about 25, 20, 19, 18, 17, 16, 15, 14, 13, 12, 11, 10, 9, 8, 7, 6, or 5 amino acids.

Suitable collagen-binding peptides may comprise a contiguous amino acid sequence of a protein that binds collagen in the extracellular matrix, such as fibronectin. In some embodiments, the collagen-binding peptide may comprise a contiguous amino acid sequence of a small interstitial leucine-rich repeat proteoglycan (e.g., selected from the group consisting of decorin, fibromodulin, lumican, and biglycan). In further embodiments, the collagen-binding peptide may be derived from a collagen protein itself (e.g., where the collagen protein is known to self-aggregate) and the peptide may comprise a contiguous amino acid sequence of a collagen protein (e.g., collagen IV). Suitable peptide for the disclosed heparin conjugates may include peptides comprising the amino acid sequence CQDSETRTFY (SEQ ID NO:1).

The disclosed heparin conjugates may comprise multiple copies of the CBP relative to heparin. For example, the disclosed heparin conjugates may comprise at least 2, 3, 4, 5, 6, 7, 8, 9, 10, 15, 20, 25, 30, 35, 40, 45, 50, 55, 60 or more moles of a CBP monomer per mole heparin monomer or heparin polymer (i.e. wherein the molar ratio of the CBP monomer to heparin monomer or heparin polymer in the heparin conjugate is at least 2, 3, 4, 5, 6, 7, 8, 9, 10, 15, 20, 25, 30, 35, 40, 45, 50, 55, 60, 65, 70, 75, 80, 85, 90, 95, 100 or greater).

Figure 11:
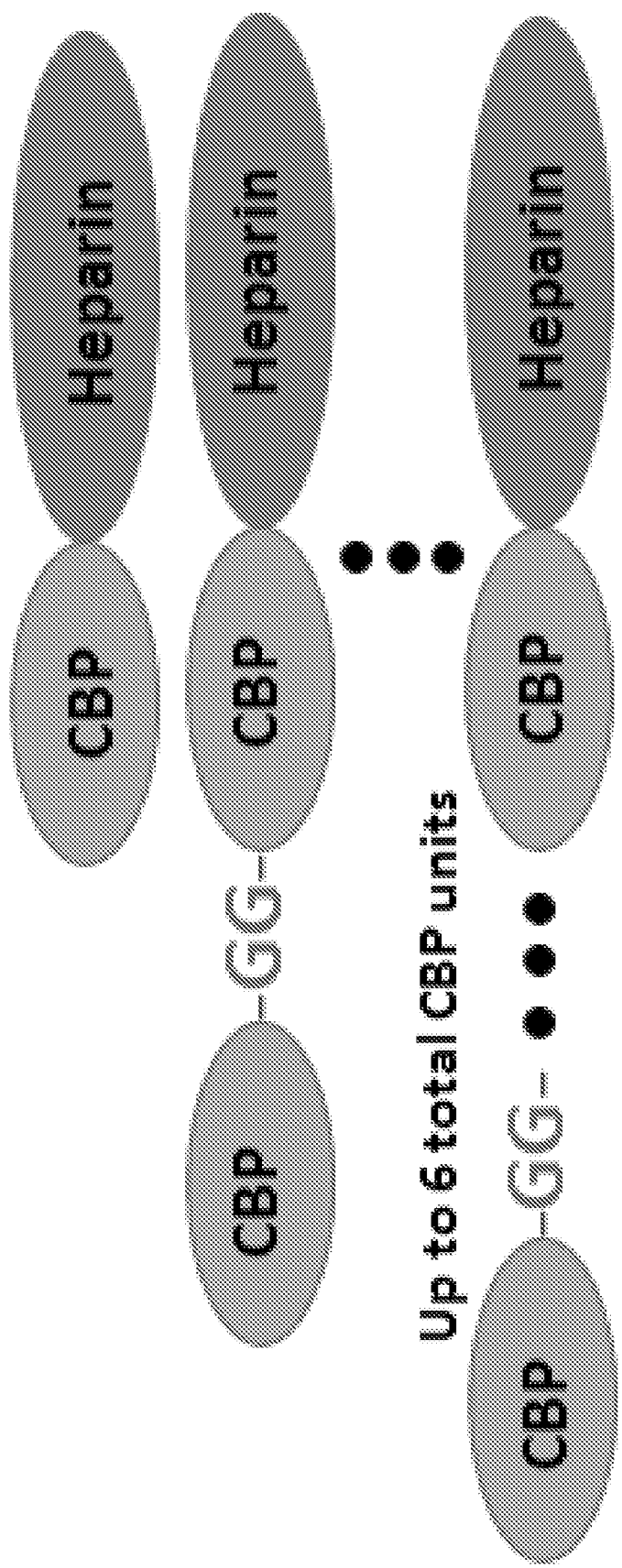
FIG. 11. Panel of linear CBP oligopeptides bound to heparin. The base example is a singular CBP linked to a heparin monomer (top). Illustrated is an embodiment of CBP:Heparin variants with variable (up to 6) CBP units linked in a linear configuration via a glycine (G) linker. Dots depict variable amounts of CBP to make up the panel of variants.

In some embodiments in which the heparin conjugates comprise multiple copies of the CBP relative to heparin, the multiple copies of the CBP may be fused by an amino acid sequence (e.g., -CBP-AA-CBP- wherein AA is an amino acid sequence that fuses a CBP to another CBP). For example, the multiple copies of the CBP may be fused by an amino acid linking sequence comprising 2, 3, 4, 5, 6, 7, 8, 9, or 10 amino acids, optionally where the amino acids are selected from the group consisting of glycine (G) and serine (S). In particular, the multiple copies of the CBP may be fused by an amino acid linking sequence comprising 2, 3, 4, 5, 6, 7, 8, 9, or 10 glycine residues such as a di-glycine linker (CBP-GG-CBP). In some embodiments in which the heparin conjugates comprise multiple copies of the CBP relative to heparin, the heparin conjugate may have a formula characterized as: $(CBP-LS)_n$-CBP-Heparin, wherein LS is a linking amino acid sequence comprising 2, 3, 4, 5, 6, 7, 8, 9, or 10 amino acids selected from the group consisting of glycine (G) and serine (S) (e.g., GG) and n is at least 1, 2, 3, 4, 5, 6, 7, 8, 9, 10, 15, 20, 25, 30, 35, 40, 50, 55, 60, 65, 70, 75, 80, 85, 90, 95, 100 or higher (or within a range bounded by any of these values). One embodiment of heparin conjugates comprising multiple copies of the CBP relative to heparin is illustrated in FIG. 11.

In some embodiments of the heparin conjugates, the CBP may be conjugated to heparin via a linking peptide that provides an amino acid backbone sequence, for example, where the CBP is conjugated as a branch from the amino acid backbone sequence of the linking peptide. In some embodiments of the heparin conjugates, the heparin conjugate comprises heparin conjugated to a linking peptide that provides a backbone amino acid sequence, the backbone amino acid sequence of the linking peptide comprising one or more lysine residues, and the CBP of the heparin conjugate is conjugated to the free amino group of the one or more lysine residues (e.g., via an amide linkage formed between a carboxyl group of the CBP and the free amino group of the lysine residue). For example, a suitable amino acid backbone sequence may comprise the sequence KGG. The disclosed heparin conjugates in particular may comprise a heparin conjugate a formula:

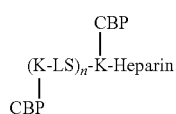

where
- n is at least 1, 2, 3, 4, 5, 6, 7, 8, 9, 10, 15, 20, 25, 30, 35, 40, 50, 55, 60, 65, 70, 75, 80, 85, 90, 95, 100 or higher (or within a range bounded by any of these values),
- the linking peptide has a sequence $(K-LS)_n-K$, where K is a lysine residue and LS is a linking sequence comprising 2, 3, 4, 5, 6, 7, 8, 9, or 10 amino acids selected from the group consisting of glycine (G) and serine (S) (e.g., GG), and
- the CBP molecules of the conjugate are conjugate via the linking peptide $(K-LS)_n-K-$ to heparin as branches.

In this embodiment, the linking peptide, for example, a linking peptide having a formula $(K-LS)_n-K-$, may be directly conjugated to heparin via an amide bond formed between an amino group of the linking peptide (e.g., an N-terminal amino group of the linking peptide) and a carboxyl group of heparin. In this embodiment, heparin may be conjugated to one or more linking peptides, which in turn, may be conjugated to one or more CBP molecules.

Figure 12:
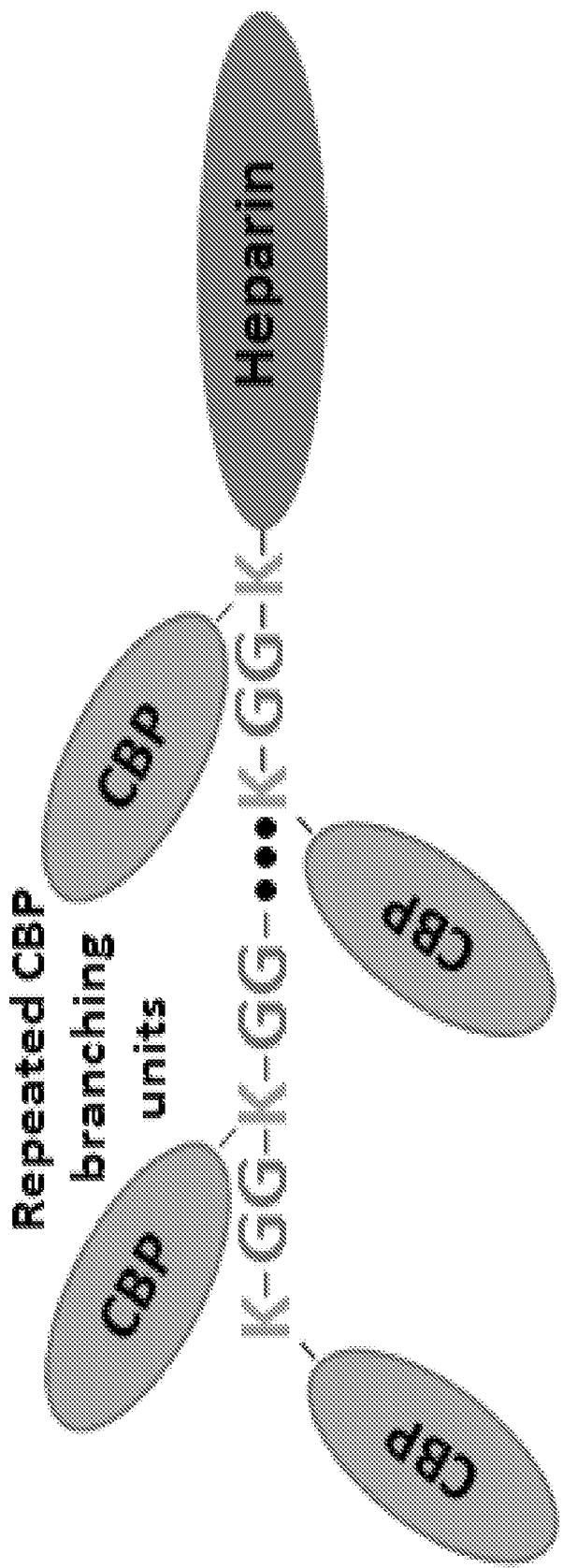
FIG. 12. Schematic diagram of branched CBP oligopeptides bound to heparin. Illustrated is an embodiment of CBP:Heparin variants with variable branched CBP units linked via lysine (K) with branched amino groups. Glycine (G) is a spacer. Dots depict variable amounts of branched CBP to make up the panel of variants.

One embodiment of heparin conjugates having CBP conjugated to heparin via an amino acid backbone sequence of a linking peptide, for example, where the CBP is conjugated as a branch from the amino acid backbone sequence of the linking peptide, is illustrated in FIG. 12. In FIG. 12, four CBP branches are conjugated to heparin via lysine residues (K) in the backbone amino acid sequence of the linking peptide comprising KGG repeats.

The disclosed heparin-conjugates may comprise heparin conjugated to a peptide (such as a collagen-binding peptide (CBP), which binds to a protein of the extracellular matrix of cellular tissue. Optionally, the disclosed heparin conjugates may comprise a conjugated fluorophore. Suitable fluorophores may include, but are not limited to: 1,5 IAEDANS; 1,8-ANS; 4-Methylumbelliferone; 5-carboxy-2,7-dichlorofluorescein; 5-Carboxyfluorescein (5-FAM); 5-Carboxytetramethylrhodamine (5-TAMRA); 5-FAM (5-Carboxyfluorescein); 5-HAT (Hydroxy Tryptamine); 5-Hydroxy Tryptamine (HAT); 5-ROX (carboxy-X-rhodamine); 5-TAMRA (5-Carboxytetramethylrhodamine); 6-Carboxyrhodamine 6G; 6-CR 6G; 6-JOE; 7-Amino-4-methylcoumarin; 7-Aminoactinomycin D (7-AAD); 7-Hydroxy-4-methylcoumarin; 9-Amino-6-chloro-2-methoxyacridine; AB Q; Acid Fuchsin; ACMA (9-Amino-6-chloro-2-methoxyacridine); Acridine Orange; Acridine Red; Acridine Yellow; Acriflavin; Acriflavin Feulgen SITSA; Alexa Fluor 350™; Alexa Fluor 430™; Alexa Fluor 488™; Alexa Fluor 532™; Alexa Fluor 546™; Alexa Fluor 568™; Alexa Fluor 594™; Alexa Fluor 633™; Alexa Fluor 647™; Alexa Fluor 660™; Alexa Fluor 680™; Alizarin Complexon; Alizarin Red; Allophycocyanin (APC); AMC; AMCA-S; AMCA (Aminomethylcoumarin); AMCA-X; Amino actinomycin D; Aminocoumarin; Aminomethylcoumarin (AMCA); Anilin Blue; Anthrocyl stearate; APC (Allophycocyanin); APC-Cy7; APTS; Astrazon Brilliant Red 4G; Astrazon Orange R; Astrazon Red 6B; Astrazon Yellow 7 GLL; Atabrine; ATTO-TAG™ CBQCA; ATTO-TAG™ FQ; Auramine; Aurophosphine G; Aurophosphine; BAO 9 (Bisaminophenyloxadiazole); Berberine Sulphate; Beta Lactamase; BFP blue shifted GFP (Y66H); Blue Fluorescent Protein; BFP/GFP FRET; Bimane; Bisbenzamide; Bisbenzimide (Hoechst); Blancophor FFG; Blancophor SV; BOBO™-1; BOBO™-3; Bodipy 492/515; Bodipy 493/503; Bodipy 500/510; Bodipy 505/515; Bodipy 530/550; Bodipy 542/563; Bodipy 558/568; Bodipy 564/570; Bodipy 576/589; Bodipy 581/591; Bodipy 630/650-X; Bodipy 650/665-X; Bodipy 665/676; Bodipy FL; Bodipy FL ATP; Bodipy F1-Ceramide; Bodipy R6G SE; Bodipy TMR; Bodipy TMR-X conjugate; Bodipy TMR-X, SE; Bodipy TR; Bodipy TR ATP; Bodipy TR-X SE; BO-PRO™-1; BO-PRO™-3; Brilliant Sulphoflavin FF; Calcein; Calcein Blue; Calcium Crimson™; Calcium Green; Calcium Orange; Calcofluor White; Carboxy-X-rhodamine (5-ROX); Cascade Blue™; Cascade Yellow; Catecholamine; CCF2 (GeneBlazer); CFDA; CFP Cyan Fluorescent Protein; CFP/YFP FRET; Chlorophyll; Chromomycin A; CL-NERF (Ratio Dye, pH); CMFDA; Coelenterazine f; Coelenterazine fcp; Coelenterazine h; Coelenterazine hcp; Coelenterazine ip; Coelenterazine n; Coelenterazine O; Coumarin Phalloidin; C-phycocyanine; CPM Methylcoumarin; CTC; CTC Formazan; Cy2™; Cy3.1 8; Cy3.5™; Cy3™; Cy5.1 8; Cy5.5™; Cy5™; Cy7™; Cyan GFP; cyclic AMP Fluorosensor (FiCRhR); Dabcyl; Dansyl; Dansyl Amine; Dansyl Cadaverine; Dansyl Chloride; Dansyl DHPE; Dansyl fluoride; DAPI; Dapoxyl; Dapoxyl 2; Dapoxyl 3; DCFDA; DCFH (Dichlorodihydrofluorescein Diacetate); DDAO; DHR (Dihydorhodamine 123); Di-4-ANEPPS; Di-8-ANEPPS (non-ratio); DiA (4-Di-16-ASP); Dichlorodihydrofluorescein Diacetate (DCFH); DiD—Lipophilic Tracer; DiD (DiIC18(5)); DIDS; Dihydorhodamine 123 (DHR); DiI (DiIC18(3)); Dinitrophenol; DiO (DiOC18(3)); DiR; DiR (DiIC18(7)); DNP; Dopamine; DsRed; DTAF; DY-630-NHS; DY-635-NHS; EBFP; ECFP; EGFP; ELF 97; Eosin; Erythrosin; Erythrosin ITC; Ethidium Bromide; Ethidium homodimer-1 (EthD-1); Euchrysin; EukoLight; Europium (III) chloride; EYFP; Fast Blue; FDA; Feulgen (Pararosaniline); FITC; Flazo Orange; Fluo-3; Fluo-4; Fluorescein (FITC); Fluorescein Diacetate; Fluoro-Emerald; Fluoro-Gold (Hydroxystilbamidine); Fluor-Ruby; FluorX; FM 1-43™; FM 4-46; Fura Red™; Fura Red™/Fluo-3; Fura-2; Fura-2/BCECF; Genacryl Brilliant Red B; Genacryl Brilliant Yellow 10GF; Genacryl Pink 3G; Genacryl Yellow SGF; GeneBlazer (CCF2); GFP (S65T); GFP red shifted (rsGFP); GFP wild type, non-UV excitation (wtGFP); GFP wild type, UV excitation (wtGFP); GFPuv; Gloxalic Acid; Granular Blue; Haematoporphyrin; Hoechst 33258; Hoechst 33342; Hoechst 34580; HPTS; Hydroxycoumarin; Hydroxystilbamidine (FluoroGold); Hydroxytryptamine; Indo-1; Indodicarbocyanine (DiD); Indotricarbocyanine (DiR); Intrawhite Cf; JC-1; JO-JO-1; JO-PRO-1; Laurodan; LDS 751 (DNA); LDS 751 (RNA); Leucophor PAF; Leucophor SF; Leucophor WS; Lissamine Rhodamine; Lissamine Rhodamine B; Calcein/Ethidium homodimer; LOLO-1; LO-PRO-1; Lucifer Yellow; Lyso Tracker Blue; Lyso Tracker Blue-White; Lyso Tracker Green; Lyso Tracker Red; Lyso Tracker Yellow; LysoSensor Blue; LysoSensor Green; LysoSensor Yellow/Blue; Mag Green; Magdala Red (Phloxin B); Mag-Fura Red; Mag-Fura-2; Mag-Fura-5; Mag-Indo-1; Magnesium Green; Magnesium Orange; Malachite Green; Marina Blue; Maxilon Brilliant Flavin 10 GFF; Maxilon Brilliant Flavin 8 G1-1-; Merocyanin; Methoxycoumarin; Mitotracker Green FM; Mitotracker Orange; Mitotracker Red; Mitramycin; Monobromobimane; Monobromobimane (mBBr-GSH); Monochlorobimane; MPS (Methyl Green Pyronine Stilbene); NBD; NBD Amine; Nile Red; Nitrobenzoxadidole; Noradrenaline; Nuclear Fast Red; Nuclear Yellow; Nylosan Brilliant Iavin EBG; Oregon Green; Oregon Green 488-X; Oregon Green™; Oregon Green™ 488;

Oregon Green™ 500; Oregon Green™ 514; Pacific Blue; Pararosaniline (Feulgen); PBFI; PE-Cy5; PE-Cy7; PerCP; PerCP-Cy5.5; PE-TexasRed [Red 613]; Phloxin B (Magdala Red); Phorwite AR; Phorwite BKL; Phorwite Rev; Phorwite RPA; Phosphine 3R; Phycoerythrin B [PE]; Phycoerythrin R [PE]; PKH26 (Sigma); PKH67; PMIA; Pontochrome Blue Black; POPO-1; POPO-3; PO-PRO-1; PO-PRO-3; Primuline; Procion Yellow; Propidium Iodid (PI); PyMPO; Pyrene; Pyronine; Pyronine B; Pyrozal Brilliant Flavin 7GF; QSY 7; Quinacrine Mustard; Red 613 [PE-TexasRed]; Resorufin; RH 414; Rhod-2; Rhodamine; Rhodamine 110; Rhodamine 123; Rhodamine 5 GLD; Rhodamine 6G; Rhodamine B; Rhodamine B 200; Rhodamine B extra; Rhodamine BB; Rhodamine BG; Rhodamine Green; Rhodamine Phallicidine; Rhodamine Phalloidine; Rhodamine Red; Rhodamine WT; Rose Bengal; R-phycocyanine; R-phycoerythrin (PE); RsGFP; S65A; S65C; S65L; S65T; Sapphire GFP; SBFI; Serotonin; Sevron Brilliant Red 2B; Sevron Brilliant Red 4G; Sevron Brilliant Red B; Sevron Orange; Sevron Yellow L; sgBFP™; sgBFP™ (super glow BFP); sgGFP™; sgGFP™ (super glow GFP); SITS; SITS (Primuline); SITS (Stilbene Isothiosulphonic Acid); SNAFL calcein; SNAFL-1; SNAFL-2; SNARF calcein; SNARF1; Sodium Green; SpectrumAqua; SpectrumGreen; SpectrumOrange; Spectrum Red; SPQ (6-methoxy-N-(3-sulfopropyl)quinolinium); Stilbene; Sulphorhodamine B can C; Sulphorhodamine G Extra; SYTO 11; SYTO 12; SYTO 13; SYTO 14; SYTO 15; SYTO 16; SYTO 17; SYTO 18; SYTO 20; SYTO 21; SYTO 22; SYTO 23; SYTO 24; SYTO 25; SYTO 40; SYTO 41; SYTO 42; SYTO 43; SYTO 44; SYTO 45; SYTO 59; SYTO 60; SYTO 61; SYTO 62; SYTO 63; SYTO 64; SYTO 80; SYTO 81; SYTO 82; SYTO 83; SYTO 84; SYTO 85; SYTOX Blue; SYTOX Green; SYTOX Orange; Tetracycline; Tetramethylrhodamine (TRITC); Texas Red™; Texas Red-X™ conjugate; Thiadicarbocyanine (DiSC3); Thiazine Red R; Thiazole Orange; Thioflavin 5; Thioflavin S; Thioflavin TCN; Thiolyte; Thiozole Orange; Tinopol CBS (Calcofluor White); TMR; TO-PRO-1; TO-PRO-3; TO-PRO-5; TOTO-1; TOTO-3; TriColor (PE-Cy5); TRITC TetramethylRodamineIsoThioCyanate; True Blue; TruRed; Ultralite; Uranine B; Uvitex SFC; wt GFP; WW 781; X-Rhodamine; XRITC; Xylene Orange; Y66F; Y66H; Y66W; Yellow GFP; YFP; YO-PRO-1; YO-PRO-3; YOYO-1; and YOYO-3. As used herein, a "fluorophore" may include a salt of the fluorophore.

In some embodiments where the disclosed heparin conjugates comprise a conjugated fluorophore, the heparin conjugates may have a formula represented as CBP-Heparin-fluorophore, CBP-fluorophore-Heparin, Heparin-CBP-fluorophore, Heparin-fluorophore-CBP, fluorophore-CBP-Heparin, or fluorophore-Heparin-CBP. In other embodiments, the disclosed heparin conjugates may have a formula represented as Cys:Heparin-fluorophore, where Cys is a single cysteine residue which optionally may be utilized to optimize chemistry of the heparin conjugates.

The disclosed heparin-conjugates comprise heparin conjugated to a peptide (such as a collagen-binding peptide (CBP), which binds to a protein of the extracellular matrix of cellular tissue. Optionally, the disclosed heparin conjugates may comprise a conjugated tracer (e.g., a radiological tracer that may be detected by magnetic resonance imaging (MRI) or computed tomography (CT) such as labeled 1,4,7,10-tetraazacyclododecane-1,4,7,10-tetraacetic acid (DOTA) or labelled dihydroxyphenylalanine (DOPA)). Radiological tracers are known in the art. (See Agdeppa et al., "A Review of Imaging Agent Development," AAPS J. 2009; 11(2):286-299; the content of which is incorporated herein by reference in its entirety.)

Also disclosed are pharmaceutical compositions that include the disclosed heparin conjugates and optionally include a suitable carrier, excipient, or diluent. The pharmaceutical compositions may be formulated for delivery by any suitable route (e.g., via systemic delivery, including but not limited to intravenous delivery).

Also disclosed are methods of treatment in which the disclosed heparin conjugates or pharmaceutical compositions comprising the disclosed heparin conjugates are administered to a subject in need thereof. A subject in need thereof may include a subject about to undergo surgery (e.g., vascular surgery) and/or a subject that has undergone surgery (e.g., vascular surgery). The methods may be practiced in order to treat and/or prevent a vascular injury or condition in a subject in need thereof.

In some embodiments of the disclosed treatment and prevention methods, the subject in need thereof is about to undergo angioplasty with or without stent insertion and/or the subject has undergone angioplasty with or without stent insertion. In the disclosed treatment and prevention methods, the disclosed heparin conjugates or pharmaceutical compositions comprising the disclosed heparin conjugates may be administered before, during, or after administering angioplasty to the subject.

In some embodiments of the disclosed treatment and prevention methods, the subject in need thereof is a subject having or an arteriovenous fistula (AVF) or arteriovenous graft (AVG). A subject in need thereof may include a subject experiencing renal failure and/or undergoing or about to undergo dialysis (e.g., a subject having diabetes).

The disclosed heparin conjugates may be further conjugated to a fluorophore as disclosed herein to provide fluorescent derivatives of the heparin conjugates. The fluorescent derivatives of the heparin conjugates may be administered to a subject and fluorescence may be detected from the fluorophore in order to track the fluorescent derivatives of the heparin conjugates (e.g., in vivo).

Also disclosed are biological materials and synthetic materials that may comprise the disclosed heparin conjugates and/or that may have been treated with the disclosed heparin conjugates. Particularly disclosed are extracellular matrices (ECMs) that may comprise the disclosed heparin conjugates and/or that may have been treated with the disclosed heparin conjugates. Suitable ECMs may include ECMs derived from vascular tissue. The disclosed ECMs may include decellularized ECMs and/or ECMs including cells.

The disclosed biological materials and synthetic materials that may comprise the disclosed heparin conjugates and/or that may have been treated with the disclosed heparin conjugates may be utilized in applications that include grafts. In particular, the disclosed extracellular matrices (ECMs) that may comprise the disclosed heparin conjugates and/or that may have been treated with the disclosed heparin conjugates may be utilized in applications that include grafts. As disclosed herein, a graft may be prepared by treating biological material, such as decellularized extracellular matrix (ECM) of cellular tissue (e.g., vascular tissue), with the heparin conjugate of any of the foregoing claims. The disclosed methods for preparing a graft further may include growing cells on the treated biological material, such as endothelial cells.

Also disclosed are methods for making the heparin conjugates. The disclosed methods may include activating a carboxyl group of heparin and covalently attaching the peptide to the activated carboxyl group via the N-terminal amino group of the peptide. In some embodiments, the heparin may be activated via reacting the heparin with 1-ethyl-3-(3-dimethylaminopropyl) carbodiimide (EDC) and N-hydroxysuccinimide (NHS).

Pharmaceutical Compositions

The heparin conjugates disclosed herein may be formulated as pharmaceutical compositions comprising the heparin conjugates and formulated for administration to a subject in need thereof. Such compositions can be formulated and/or administered in dosages and by techniques well known to those skilled in the medical arts taking into consideration such factors as the age, sex, weight, and condition of the particular patient, and the route of administration. In some embodiments, the pharmaceutical compositions may be formulated for delivery systemically, for example, intravenously. In some embodiments, the pharmaceutical compositions may be formulated for delivery via a catheter or device for administering angioplasty (e.g., before, during or after administering angioplasty).

The compositions may include pharmaceutical solutions comprising carriers, diluents, excipients, and surfactants, as known in the art. Further, the compositions may include preservatives (e.g., anti-microbial or anti-bacterial agents such as benzalkonium chloride). The compositions also may include buffering agents (e.g., in order to maintain the pH of the composition between 6.5 and 7.5).

The pharmaceutical compositions may be administered therapeutically or prophylactically. In therapeutic applications, the compositions are administered to a patient in an amount sufficient to elicit a therapeutic effect (e.g., a response which cures or at least partially arrests or slows symptoms and/or complications of from surgery, a disorder, or a disease (i.e., a "therapeutically effective dose")). In prophylactic applications, the compositions are administered to a patient in an amount sufficient to elicit a prophylactic effect (e.g., a response which prevent symptoms and/or complications from surgery, a disorder, or a disease (i.e., a "prophylactically effective dose")).

Illustrative Embodiments

The following embodiments are illustrative and should not be interpreted to limit the scope of the claimed subject matter.

Embodiment 1. A heparin conjugate comprising heparin conjugated to a peptide that binds to one or more components of the extracellular matrix (ECM), optionally wherein the ECM-binding peptide is a collagen-binding peptide (CBP) and optionally wherein the ECM-binding peptide is conjugated to heparin directly or indirectly via an amide bond formed between a carboxyl group of heparin and an N-terminal amino group of the ECM-binding peptide or an N-terminal amino group of a linking peptide that links the ECM-binding peptide indirectly to heparin.

Embodiment 2. The heparin conjugate of embodiment 1, wherein the heparin is low molecular weight heparin.

Embodiment 3. The heparin conjugate of embodiment 1 or 2, wherein the heparin conjugate binds to one or more collagen types, preferably wherein the heparin conjugate binds to collagen I and/or collagen IV.

Embodiment 4. The heparin conjugate of any of the foregoing embodiments, wherein the heparin conjugate binds to collagen IV.

Embodiment 5. The heparin conjugate of any of the foregoing embodiments, wherein the heparin conjugate binds to antithrombin.

Embodiment 6. The heparin conjugate of any of the foregoing embodiments, wherein the heparin conjugate has an anti-Factor Xa activity greater than about 0.5, 1, 5, 10, 20, 30, 40, 50, 100, 150, or 200 U/mg, or the heparin conjugate completely abrogates Factor Xa activity.

Embodiment 7. The heparin conjugate of any of the foregoing embodiments, comprising heparin conjugated directly to the collagen-binding peptide via an amide linkage between a carboxyl group of the heparin and the N-terminal amino group of the peptide.

Embodiment 8. The heparin conjugate of any of the foregoing embodiments, wherein the collagen-binding peptide has an amino acid sequence of no more than about 25, 20, 19, 18, 17, 16, 15, 14, 13, 12, 11, 10, 9, 8, 7, 6, or 5 amino acids.

Embodiment 9. The heparin conjugate of any of the foregoing embodiments, wherein the CBP comprises a contiguous amino acid sequence of a protein of a biological material, such as the extracellular matrix (ECM).

Embodiment 10. The heparin conjugate of embodiment 9, wherein the CBP comprises a contiguous amino acid sequence of a protein of a biological material, such as the extracellular matrix (ECM) of vascular tissue.

Embodiment 11. The heparin conjugate of embodiment of 9 or 10, wherein the protein of the ECM of vascular tissue is fibronectin.

Embodiment 12. The heparin conjugate of any of embodiments 9-11, wherein the protein of the ECM of vascular tissue is a member of the small interstitial leucine-rich repeat proteoglycans.

Embodiment 13. The heparin conjugate of any of embodiments 9-12, wherein the protein of the ECM of vascular tissue is selected from the group consisting of decorin, fibromodulin, lumican, and biglycan.

Embodiment 14. The heparin conjugate of any of embodiments 9-13, wherein the protein of the ECM of vascular tissue is a collagen protein.

Embodiment 15. The heparin conjugate of embodiment 14, wherein the collagen protein is collagen IV.

Embodiment 16. The heparin conjugate of any of the foregoing embodiments, wherein the CBP comprises the amino acid sequence CQDSETRTFY (SEQ ID NO:1).

Embodiment 17. The heparin conjugate of any of the foregoing embodiments, wherein the heparin conjugate comprises multiple copies of the CBP monomer relative to a heparin monomer or heparin polymer, for example wherein the heparin conjugate comprises at least 2, 3, 4, 5, 6, 7, 8, 9, 10, 15, 20, 25, 30, 35, 40, 45, 50, 55, 60, 65, 70, 75, 80, 85, 90, 95, 100 or more moles of the CBP monomer per mole heparin monomer or heparin polymer.

Embodiment 18. The heparin conjugate of embodiment 17, wherein the multiple copies of the CBP are fused by a linking sequence comprising at least 2, 3, 4, 5, 6, 7, 8, 9, or 10 amino acids selected from the group consisting of glycine (G) and serine (S) (e.g., GG).

Embodiment 19. The heparin conjugate of embodiment 17 or 18 having a formula: (CBP-LS)$_n$-CBP-Heparin, wherein LS is a linking sequence comprising at least 2, 3, 4, 5, 6, 7, 8, 9, or 10 amino acids selected from the group consisting of glycine (G) and serine (S) (e.g., GG) and n is at least 1, 2, 3, 4, 5, 6, 7, 8, 9, 10, 15, 20, 25, 30, 35, 40, 50, 55, 60, 65, 70, 75, 80, 85, 90, 95, 100 or more (or within a range bounded by any of these values).

Embodiment 20. The heparin conjugate of any of embodiments 1-16, wherein the heparin conjugate comprises heparin conjugated to a linking peptide that provides a backbone amino acid sequence for linking CBP indirectly to heparin, the backbone amino acid sequence comprising one or more lysine residues, and the CBP of the heparin conjugate is conjugated to the amino group of the one or more lysine residues.

Embodiment 21. The heparin conjugate of embodiment 20, wherein the backbone amino acid sequence comprises the sequence KGG.

Embodiment 22. The heparin conjugate of embodiment 20 or 21, wherein the heparin conjugate comprises a formula:

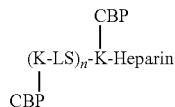

wherein:
n is at least 1, 2, 3, 4, 5, 6, 7, 8, 9, 10, 15, 20, 25, 30, 35, 40, 50, 55, 60, 65, 70, 75, 80, 85, 90, 95, 100 or more (or within a range bounded by any of these values),
the linking peptide has a formula $(K-LS)_n-K$, wherein K is a lysine residue and LS is a linking sequence comprising at least 2, 3, 4, 5, 6, 7, 8, 9, or 10 amino acids selected from the group consisting of glycine (G) and serine (S) (e.g., GG),
and the CBP molecules are conjugated to heparin as branch units.

Embodiment 23. The heparin conjugate of any of the foregoing embodiments, further comprising a conjugated fluorophore or a radiological tracer.

Embodiment 24. A pharmaceutical composition comprising the heparin conjugate of embodiment 1 and a suitable carrier.

Embodiment 25. A method of treating and/or preventing a vascular injury or condition in a subject in need thereof, the method comprising administering the pharmaceutical composition of embodiment 24 to the subject.

Embodiment 26. The method of embodiment 25, wherein the pharmaceutical composition is administered before, during, or after administering angioplasty to the subject.

Embodiment 27. The method of embodiment 25 or 26, wherein the vascular injury or condition is an arteriovenous fistula (AVF) or arteriovenous graft (AVG).

Embodiment 28. A method comprising administering the heparin conjugate conjugated to a fluorophore of embodiment 23 to a subject and detecting fluorescence from the fluorophore (optionally detecting fluorescence from the fluorophore in vivo).

Embodiment 29. A biological material or synthetic material comprising the heparin conjugate of any of the foregoing embodiments, optionally wherein the biological material is decellularized biological material such as decellularized ECM of cellular tissue.

Embodiment 30. The decellularized ECM of embodiment 29, wherein the decellularized ECM is decellularized ECM of vascular tissue or ECM of an organ (such as a liver, kidney, heart, lung, pancreas, spleen, bone, skin) that contain vascular tissue.

Embodiment 31. A vascular graft comprising the ECM of embodiment 29 or 30.

Embodiment 32. A method for making the heparin conjugate of any of the foregoing embodiments, the method comprising activating a carboxyl group of heparin and covalently attaching the peptide to the activated carboxyl group via the N-terminal amino group of the peptide.

Embodiment 33. The method of embodiment 32, wherein the carboxyl group of heparin is activated via reacting the heparin with 1-ethyl-3-(3-dimethylaminopropyl) carbodiimide (EDC) and N-hydroxysuccinimide (NHS).

Embodiment 34. A method for preparing a graft, the method comprising treating biological material (optionally decellularized biological material) or synthetic material with the heparin conjugate of any of the foregoing embodiments, optionally where the decellularized biological material is decellularized extracellular matrix (ECM) of cellular tissue.

Embodiment 35. The method of embodiment 34, wherein the graft is a vascular graft and the decellularized biological material is decellularized ECM of vascular tissue, or the graft is an ECM of an organ that contains vascular tissue selected from liver, kidney, heart, lung, pancreas, spleen, bone, skin.

Embodiment 36. The method of embodiment 34 or 35, further comprising growing cells on the graft of vascular tissue or containing vascular tissue.

Embodiment 37. The method of embodiment 36, wherein the cells are endothelial cells or smooth muscle cells.

EXAMPLES

The following Examples are illustrative and are not intended to limit the scope of the claimed subject matter.

Example 1—Targeting Heparin to Collagen within Extracellular Matrix Significantly Reduces Thrombogenicity and Improves Endothelialization of Decellularized Tissues Reference is made to Jiang et al., "Targeting Heparin to Collagen within Extracellular Matrix Significantly Reduces Thrombogenicity and Improves Endothelialization of Decellularized Tissues," Biomacromolecules, 2016, 17 (12), pp 3940-3948, the content of which is incorporated herein by reference in its entirety.

Thrombosis within small-diameter vascular grafts limits the development of bioartificial, engineered vascular conduits, especially those derived from extracellular matrix (ECM). Here we describe an easy-to-implement strategy to chemically modify vascular ECM by covalently linking a collagen binding peptide (CBP) to heparin to form a heparin derivative (CBP-heparin) that selectively binds a subset of collagens. Modification of ECM with CBP-heparin leads to increased deposition of functional heparin (by ~7.2-fold measured by glycosaminoglycan composition) and a corresponding reduction in platelet binding (>70%) and whole blood clotting (>80%) onto the ECM. Furthermore, addition of CBP-heparin to the ECM stabilizes long-term endothelial cell attachment to the lumen of ECM-derived vascular conduits, potentially through recruitment of heparin-binding growth factors that ultimately improve the durability of endothelialization in vitro. Overall, our findings provide a simple yet effective method to increase deposition of functional heparin on the surface of ECM-based vascular grafts and thereby minimize thrombogenicity of decellularized tissue, overcoming a significant challenge in tissue engineering of bioartificial vessels and vascularized organs.

Introduction

Vascular thrombosis continues to be a major problem and contributor to patient morbidly in clinical vascular surgery and limits progress toward development of small caliber synthetic and biosynthetic blood vessels. Thrombosis, precipitating vessel occlusion, is the result of platelet activation when the subendothelial basement membrane containing collagens and other extracellular matrix (ECM) proteins are exposed to circulating blood at the site of anastomosis during vascular surgery.[1] Thrombosis is also a major obstacle in organ and tissue engineering, where exposed ECM may be a nidus for clot formation. Despite reconstitution of decellularized tissues and organs with endothelial cells, naturally occurring three-dimensional biologic scaffolds derived from heart,[2] liver,[3] kidney,[4] and lung[5] often times require systemic anticoagulation and lead to low patency of limited duration (hours to days) after implantation into recipient animal models. Systemic administration of prophylactic, anticoagulant (e.g., heparin), or antiplatelet agents (e.g., aspirin, clopidogrel) to prevent thrombosis increases the risk of undesired bleeding, which may result in debilitating or life-threatening hemorrhage.[6]

Strategies to locally deliver and immobilize heparin to sites of injury at the subendothelial matrix often involves chemical cross-linking[7] that changes the ultrastructure and mechanical properties of native ECM, resulting in macrophage activation, inflammation, and vascular calcification.[8] To deliver heparin without altering the compliance of biosynthetic vascular grafts to ultimately reduce thrombogenicity, we synthesized a bifunctional macromolecule linking the anticoagulant heparin with a ten-amino-acid peptide sequence that specifically recognizes and binds to a subset of the collagen family of ECM macromolecules. Collagen-binding peptide, or CBP (amino acid sequence CQDSETRTFY (SEQ ID NO:1), or Cys-Gln-Asp-Ser-Glu-Thr-Arg-Thr-Phe-Tyr), is a fragment encoding a collagen-binding domain found in fibronectin that was originally identified in 1984.[9,10] We used this fragment as a targeting sequence to selectively confer the properties of heparin to decellularized tissue (ECM), where collagens and other structural macromolecules are ubiquitously present. In this study, we determine the binding specificity of CBP within ECM to demonstrate that it binds selectively to collagen, and specifically discriminates between its subtypes, to reduce the thrombogenicity of ECM compared to unmodified heparin. Moreover, we demonstrate that targeted modification of the ECM with CBP-heparin recruits heparin-binding growth factors to the matrix and improves longevity of endothelial cells grown on heparin-modified ECM used to reconstitute vascular grafts, which may provide an added benefit to improve the long-term thromboresistance of the vascular graft by maintaining an endothelial lining that protects the subendothelial matrix from circulating blood.

Experimental Section

Materials. CBP (CQDSETRTFY (SEQ ID NO:1)) and its inactive, nonbinding form CBPi (CDEFQRSTTY (SEQ ID NO:2)) with and without biotinylation were custom synthesized by ABI Scientific, Inc. (Sterling, VA). Heparin sodium (average molecular weight 15 kDa) was purchased from Celsus Glycoscience, Inc. (Cincinnati, OH). Collagen types I (rat), II (chicken), III (human), and IV (mouse), laminin (mouse), 2-(N-morpholino) ethanesulfonic acid (MES), 1-ethyl-3-(3-(dimethylamino)propyl)-carbodiimide (EDC), N-hydroxysuccinimide (NHS), and resazurin were obtained from Sigma-Aldrich (St. Louis, MO). Streptavidin (Alexa Fluor 594 conjugate), phalloidin (Alexa Fluor 488 conjugate), fibronectin from human plasma, and Matrigel were obtained from Thermo Fisher Scientific Inc. (Waltham, MA).

Peptide and ECM Binding Specificity. Collagens I, II, III, and IV, fibronectin, laminin, and Matrigel were coated onto 96-well black plates at 10 µg/cm². Biotinylated CBP or CBPi were added to coated plates at 0, 1, 10, 100, and 1000 µM overnight at 4° C., after which the plates were washed three times with PBS. Fluorescent streptavidin-594 (4 µg/mL) was added to each well and incubated at room temperature for 2 h, then thoroughly washed with PBS. The plates were read with a fluorescence microplate reader for fluorescence intensity (Ex 591 nm, Em 614 nm). All data were normalized to the background fluorescence intensity of Streptavidin-594 alone directed at each coated protein.

Peptide—Heparin Conjugation and Characterization.

Synthesis of Heparin—Peptide Conjugates. Heparin was conjugated with CBP or CBPi via carbodiimide chemistry (FIG. 1A). Heparin sodium (1 mM) was dissolved in MES buffer (pH 6.5) and activated in the presence of EDC (120 mM) and NHS (60 mM) for 4 h at room temperature. CBP or CBPi was then added to the activated heparin at 1 mM (molar ratio of heparin/peptide 1:1) and allowed to react at 4° C. overnight. The product was dialyzed against Milli-Q water with MWCO 3500 membrane to remove unbound peptides and small molecules, and lyophilized to dry.

Concentration of Heparin and Peptide in Conjugates. To characterize the heparin to peptide mass and molar ratio after the reaction, the lyophilized product was dissolved in water at 1 mg/mL. The concentration of heparinized macromolecule in the solution was quantified using a dimethylmethylene blue (DMMB) based glycosaminoglycan (GAG) assay as previously described.[11] Serial dilutions of heparin sodium were used to generate standard curve. The concentration of peptide was quantified using Ellman's reagent assay[12] to detect cysteine in CBP or CBPi. Serial dilutions of L-cysteine were used to generate a standard curve. The mass and molar concentrations of heparin and peptide were then calculated separately and compared to obtain the mass and molar ratios.

Anti-Factor Xa Activity of Heparin—Peptide Conjugates.

The anticoagulant activity of heparin after conjugation with the CBP or CBPi peptide was quantified using a chromogenic anti-Factor Xa assay (Chromogenix, West Chester, OH). CBP-heparin or CBPi-heparin was diluted in PBS to 10 µg/mL and added to antithrombin to form the CBP/CBPi-heparin-antithrombin complex to neutralize factor Xa, which is proportional to the amount of active heparin in the conjugated macromolecule. The remaining activated factor Xa hydrolyzes the chromogenic substrate S-2222, which was read on a colorimetric detector at 405 nm. Heparin sodium (anti-Factor Xa activity 200 U/mg) was diluted to 0.1-0.7 U/mL in PBS as a reference standard. The anti-Factor Xa activity of CBP-heparin and CBPi-heparin is represented as U/mg.

Figure 1B:
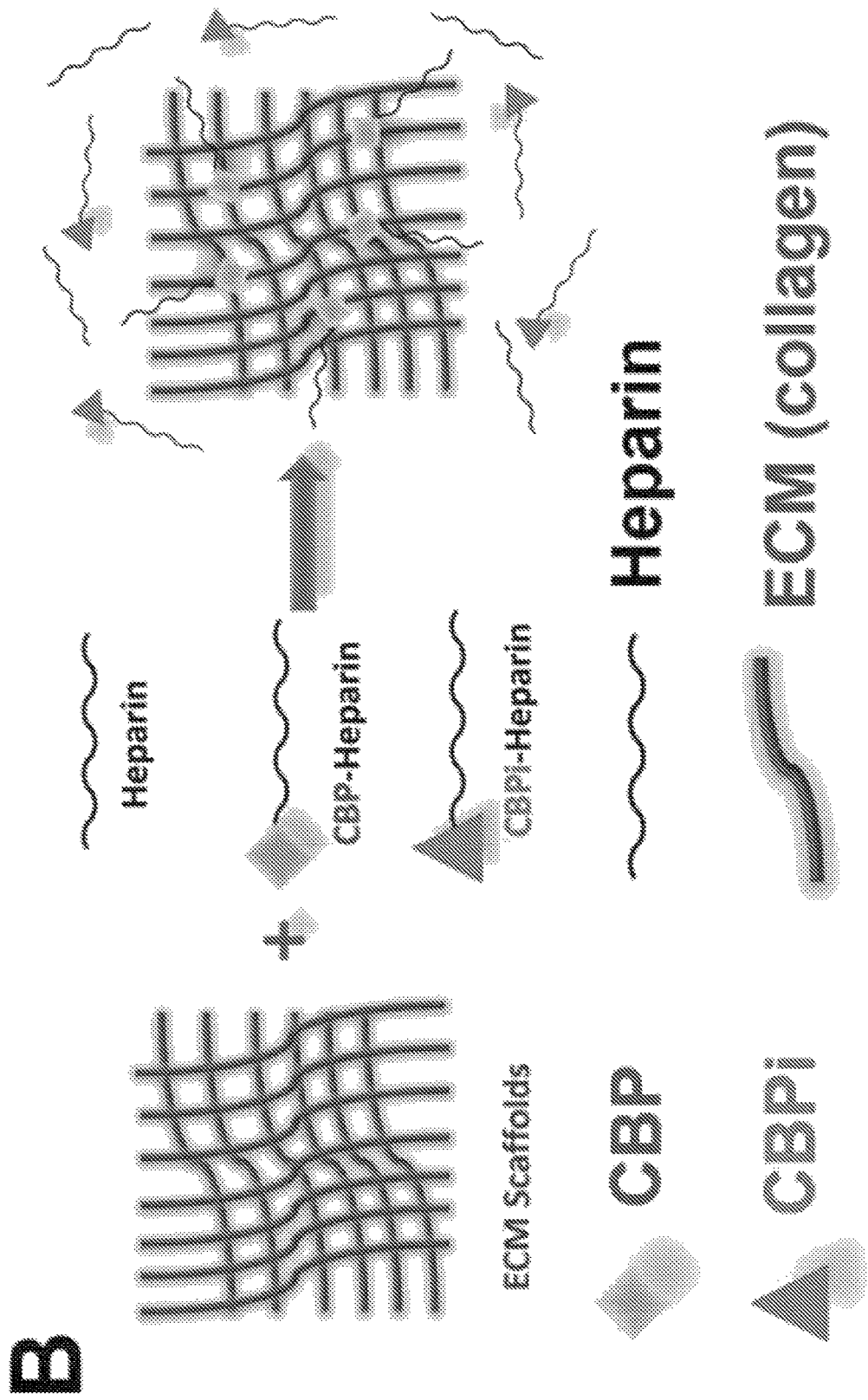

Heparin Immobilization onto Rat Aorta ECM. All animal experiments and procedures were approved by the Animal Care and Use Committee of Northwestern University and animal care was performed in accordance with the NIH Guide for Care and Use of Laboratory Animals. Male Sprague-Dawley rats weighing 200-250 g (Charles River Laboratories, Chicago, IL) were used as donors to recover the abdominal segment of the aorta. Rat aorta ECM was isolated via decellularization as described 13 using 1% Triton X for 48 h and 1.5% SDS for 48 h at room temperature, followed by 100 U/mL DNase I solution at 37° C. for 4 h. Aorta ECM was subsequently incubated with heparin sodium, CBP-conjugated heparin or CBPi-conjugated heparin (1 mg/mL) overnight at 4° C., followed by three washes with PBS to remove excessive and unbound heparin (FIG. 1B). ECM without heparin incubation served as negative, untreated controls.

Heparinized ECM Characterization.

Quantification of Heparin Deposited onto ECM. The amount of heparin immobilized onto aorta ECM was quantified using a GAG assay. 14 ECM samples (PBS, heparin, CBPi-heparin, or CBP-heparin-treated) were weighed and digested with Proteinase K, and the digested material was added to DMMB solution for colorimetric measurement. Retention of heparin on ECM after CBP-heparin treatment was assessed by incubating heparinized ECM in endothelial growth medium (EGM-2, Lonza) at 37° C. and measuring the amount of heparin remaining on ECM weekly using a GAG assay. ECM samples without heparin modification served as a baseline control.

Surface Morphology Characterization. Scanning electron microscopy (SEM) was used to evaluate the surface topography of modified ECM. Treated ECM (PBS, heparin, CBPi-heparin, or CBP-heparin) were fixed with 2.5% glutaraldehyde for 2 h, followed by incubation with 0.1 M sodium cacodylate buffer overnight at 4° C. The samples were then dehydrated in a series of ethanol solutions, followed by critical point drying and gold sputter coating at the Northwestern University Biological Imaging Facility (BIF, Evanston, IL). The luminal surface of each graft was imaged with a Hitachi S4800-II cFEG SEM at the Electron Probe Instrumentation Center (EPIC) at Northwestern University (Evanston, IL).

Platelet Adhesion. The thrombogenic properties of modified ECM were evaluated by a platelet adhesion assay described previously.[13] ECM grafts were incubated in diluted rat platelet rich plasma (2-5×108 platelet/mL) at 37° C. for 1 h, rinsed with warm PBS, and lysed with 2% Triton-X. Lactate dehydrogenase (LDH) released into the medium was measured by an LDH assay following the manufacturer's protocol (Roche Molecular Diagnostics, Pleasanton, CA). LDH measured from lysates of serially diluted platelets standardized the assay to quantify the concentration of deposited platelet on ECM.

Clot Formation of Recalcified Whole Blood. A recalcified whole blood clotting assay was performed to assess hemocompatibility of ECM grafts treated with or without the addition of heparin, alone or conjugated to CBP/CBPi.[15] Briefly, 0.01 M $CaCl_2$ was added to anticoagulated porcine blood and incubated with ECM grafts for 1 h at room temperature. Each sample was weighed before and after incubation with recalcified blood, and the mass of the blood clotted on each sample was calculated and normalized to the weight of the ECM. Each sample containing clotted blood was subsequently embedded in paraffin, sectioned and stained with H&E for microscopic analysis.

Growth Factor Binding to Modified ECM. ECM samples treated with PBS alone, heparin alone, CBPi-heparin, or CBP-heparin were incubated in EGM-2 (containing 2 ng/mL recombinant human vascular endothelial growth factor, VEGF) for 3 days and washed with PBS to measure the degree of VEGF recruited to heparin modified ECM. ECM grafts before and after EGM-2 incubation were weighed and proteins were extracted as previously described using a urea buffer. 13 The amount of VEGF was measured using an ELISA for human and rat VEGF (Thermo Fisher, Waltham, MA).

Endothelial Cell Adhesion and Retention on ECM.

Addition of Endothelial Cells to Modified ECM. Human umbilical vein endothelial cells (HUVECs, Lonza) at passages 3-8 were cultured in EGM-2 and used for cell seeding. The following groups of ECM vascular grafts (1 cm in length each, n=3 per group) were prepared: (1) ECM control alone without heparin or peptide; (2) ECM incubated with free, unconjugated heparin sodium (1 mg/mL); (3) ECM incubated with CBPi conjugated to heparin (1 mg/mL); and (4) ECM incubated with CBP conjugated to heparin (1 mg/mL). HUVECs were seeded twice onto the lumen of each graft (10000 cells/$cm^2$ at each inoculation) with a 180° rotation of the graft at 30 min after initial seeding. Recellularized grafts were maintained in culture under static condition with medium changed every 2 days.

Cell Number and Viability Measurement. Resazurin was used to assess cell number and viability of HUVECs on ECM grafts over time. 16 Resazurin sodium (44 μM in EGM-2) was added to cell-laden, ECM-modified grafts and incubated for 2 h and the fluorescence intensity (Ex 560 nm, Em 590 nm) was read. The number of cells was calculated based on the fluorescence reading of serially diluted HUVEC suspensions incubated in resazurin solution to develop a standard curve. Prior to performing each measurement, cell seeded grafts were moved to a new low-attachment, multiwell plate to eliminate off target readings from cells that may have migrated off the graft.

Cell Staining and Fluorescence Microscopy. At 4 weeks after cell seeding, each cell-seeded graft was fixed with paraformaldehyde and stained with Phalloidin-488. Fluorescence microscopy (Nikon TE2000U, Japan) was performed on the flattened luminal surface of the graft.

Statistical Analysis. All statistical data were expressed as mean±standard deviation. Data were analyzed using one-way ANOVA with a Tukey-Kramer post-test on SigmaStat (San Jose, CA). For all comparisons, $p<0.05$ was considered statistically significant.

Results and Discussion

Figure 2A:
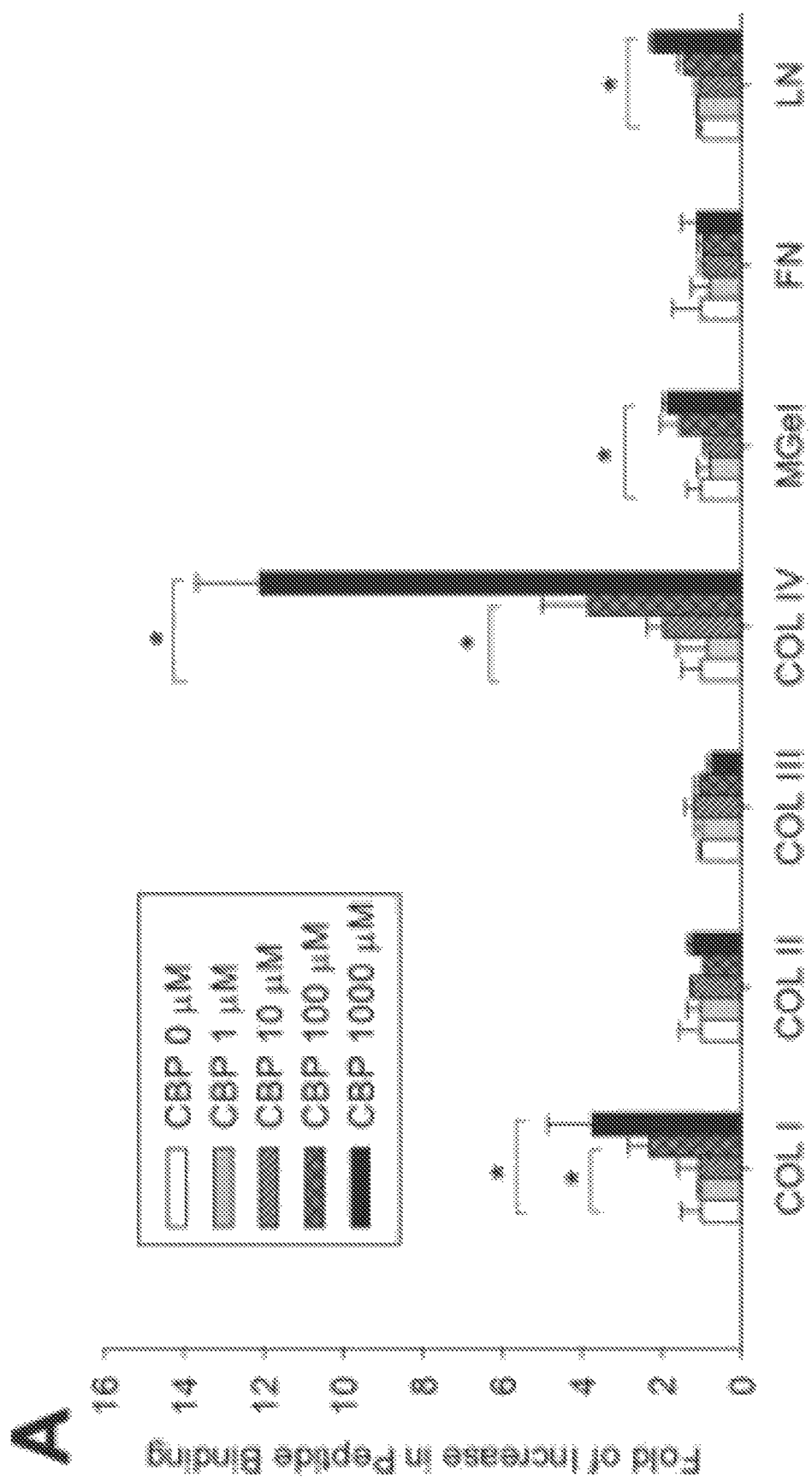
FIG. 2. Biotinylated CBP (A) or CBPi (B) binding specificity to surfaces coated with ECM proteins, collagen I (COL I), collagen II (COL II), collagen III (COL III), collagen IV (COL IV), Matrigel (MGel), fibronectin (FN), and laminin (LN). *p<0.05 (n=4).
Figure 2B:
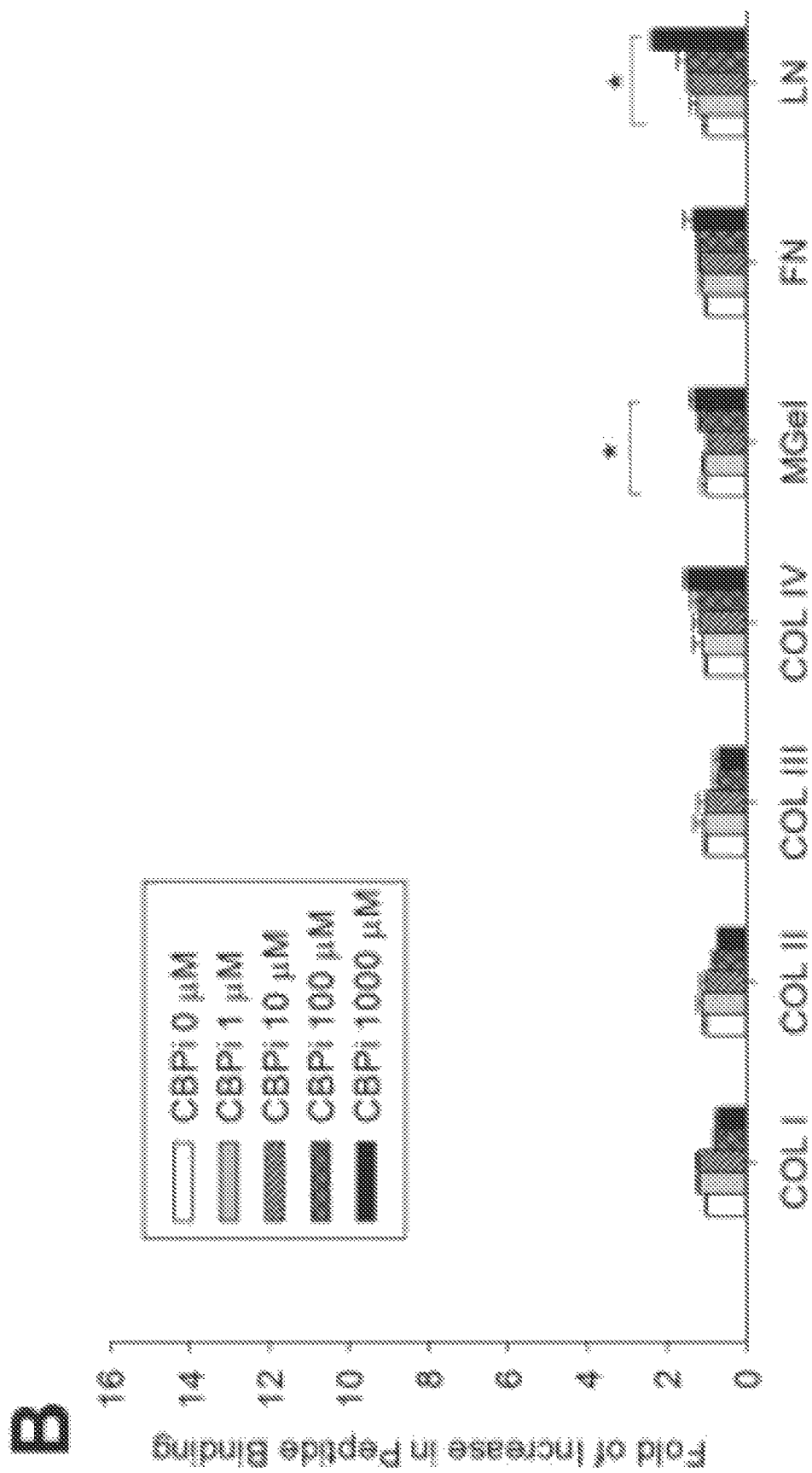

CBP Selectively Binds to ECM with High Specificity to Collagen IV. To test binding specificity of CBP to ECM proteins, biotinylated CBP (biotin-CQDSETRTFY (SEQ ID NO:1)) or its inactive, nonbinding sequence CBPi (biotin-CDEFQRSTTY (SEQ ID NO:2)) was incubated with surfaces coated with a series of ECM proteins at varying peptide concentrations. Bound peptides were subsequently probed with fluorescently labeled streptavidin. CBP, but not CBPi, bound specifically to collagen IV coated surfaces with high relative affinity, and to collagen I coated surfaces to a much lesser extent. CBP bound to collagen IV in a dose-dependent manner, with a 3.85±1.17-fold increase in surface fluorescence intensity at 100 μM CBP, and a 12.09±1.59-fold increase in surface fluorescence intensity at 1000 μM CBP (FIG. 2A), compared to increase at 1000 μM CBP compared to the background fluorescence (1.00±0.03 at 0 μM CBP), whereas CBPi at 1000 μM did not result in any increase in surface concentration. Neither CBP nor CBPi binds to collagen II, collagen III, or fibronectin. Both CBP and CBPi at 1000 μM showed minimal, through significant, levels of binding to laminin and Matrigel, suggesting a low degree of nonspecific adhesion to these ECM components.

Figure 7:
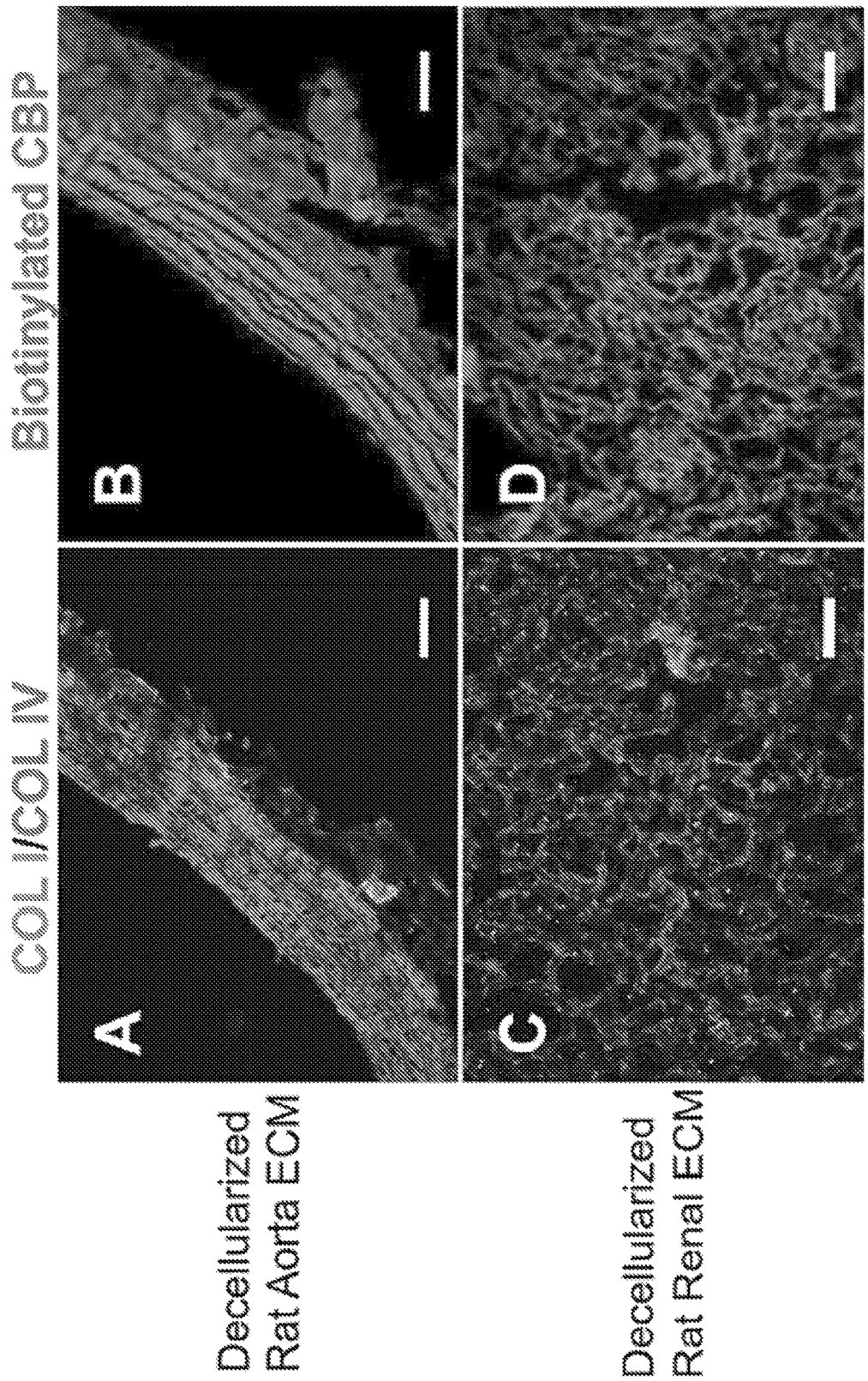
FIG. 7: Immunofluorescence staining of collagen I and collagen IV in decellularized rat aorta ECM (A) and renal ECM (C). Streptavidin-594 staining of biotinylated CBP on decellularized rat aorta ECM (B) and renal ECM (D). Scale bar=100 µm.

The binding between collagens (types I and IV) and CBP, is predicted to be mediated by intermolecular forces between discrete amino acids within collagen and CBP[17] that contribute to the binding specificity observed above. The molecular composition of ECM is largely heterogeneous, including fibrous proteins such as collagens, soluble proteins such as fibronectin and laminin, and proteoglycans such as heparan sulfate, keratin sulfate, and chondroitin sulfate.[18] The detailed composition of ECM proteins also varies from tissue to tissue, however, ECM from most tissue types contains collagen I (interstitial matrix) and collagen IV (basement membrane).[18] Each collagen subtype is retained in decellularized tissues, specifically vascular (FIG. 7A) and renal tissues (FIG. 7C). To evaluate binding to collagens within these tissues, biotinylated CBP was administered at 100 μM (FIG. 7B,D) and colocalized with each subtype but was more prominent around collagen IV, in agreement with binding studies to individual ECM proteins described above. Taken together, this delivery strategy using CBP as a localizing moiety specifically targets collagens (type IV in particular) and may be used to selectively carry bioactive molecules to the vasculature where collagen IV defines the subendothelial basement membrane that forms the vascular network, including the macro- and micro-vasculatures within all tissues and organs.

Though the use of ECM-binding peptides have been characterized elsewhere, such as a domain within placenta growth factor-2 (P1GF-2123-144)[19] that strongly and promiscuously binds various ECM proteins (including fibronectin, vitronectin, fibrinogen, collagen I, etc.), this strategy using CBP imparts a high degree of specificity for a subset of ECM and collagen matrix components.

Figure 3:
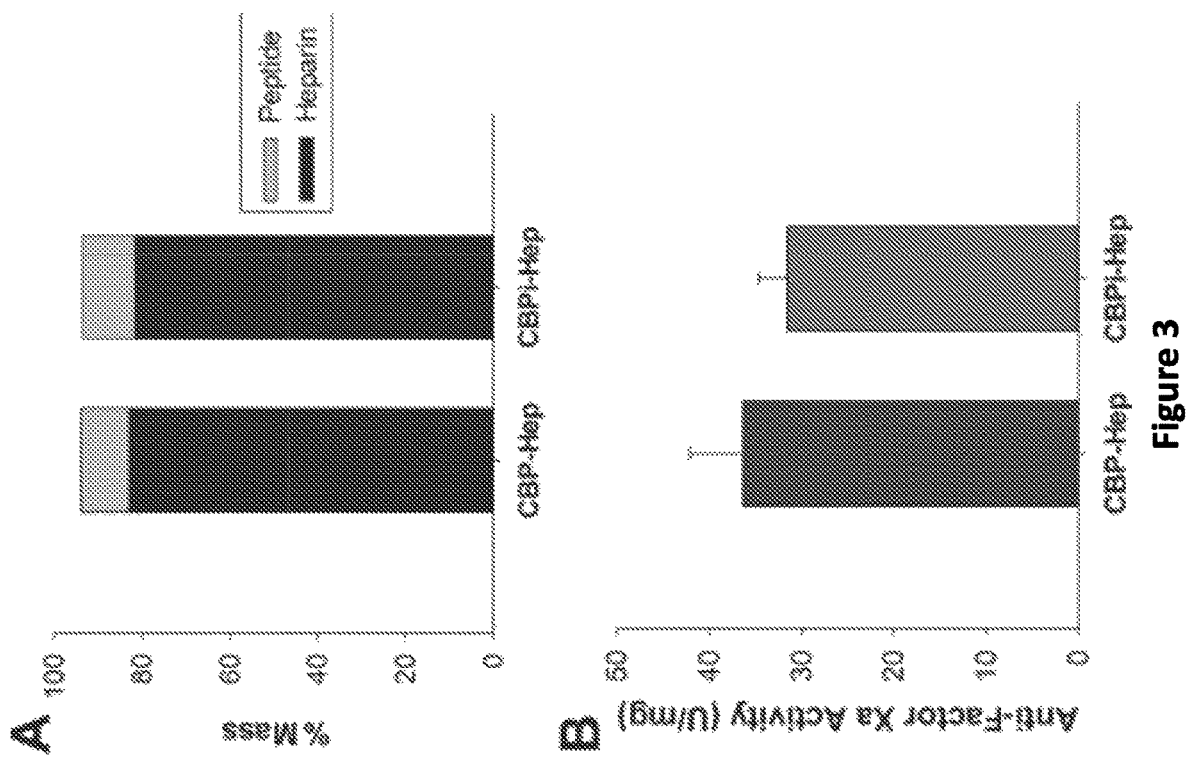
FIG. 3. (A) Mass ratio and (B) anti-factor Xa bioactivity of peptide-heparin conjugates (CBP vs CBPi). No significant difference (p>0.05) was found between CBP-heparin and CBPi-heparin (n=3).
Figure 4:
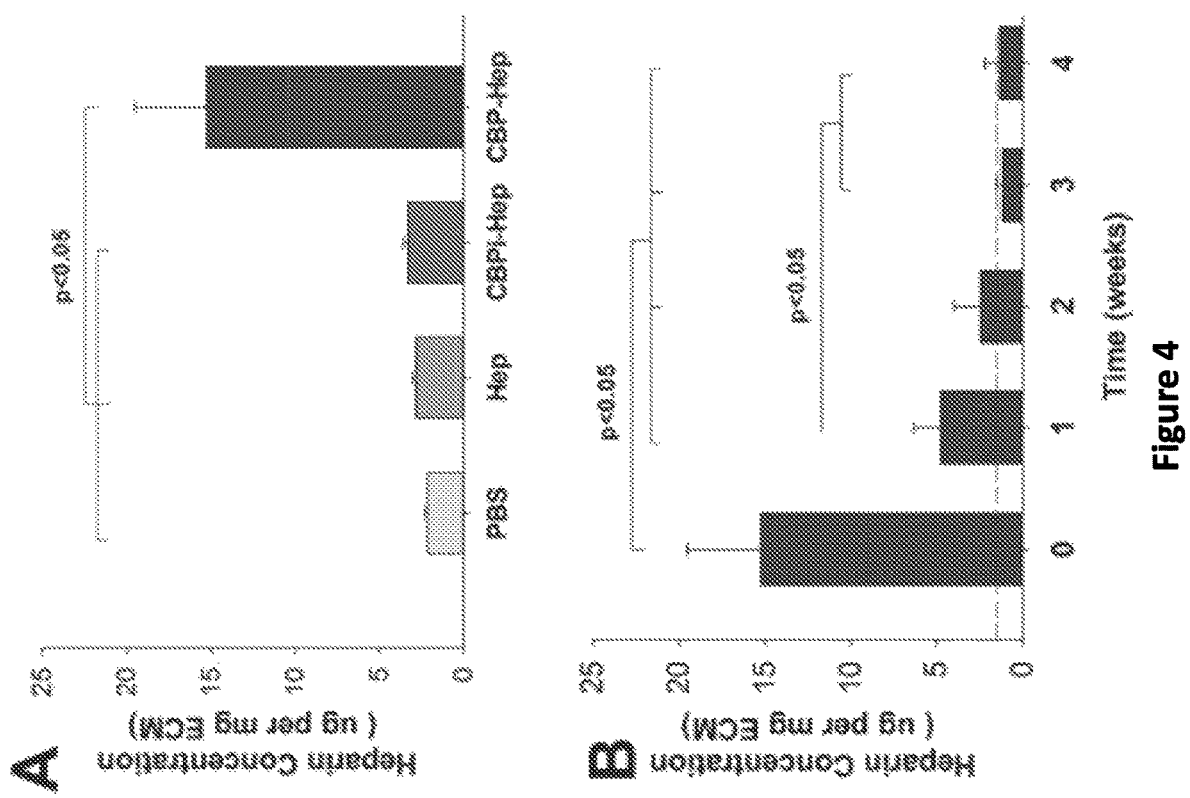
FIG. 4. Heparin concentration measured in ECM (A) immediately after treatment with PBS, heparin sodium, CBPi-heparin or CBP-heparin, and (B) up to 4 weeks after ECM modification. The dash line indicates baseline level of glycosaminoglycans (GAGs) measured in ECM at t=0 (n=3).
Figure 8A:
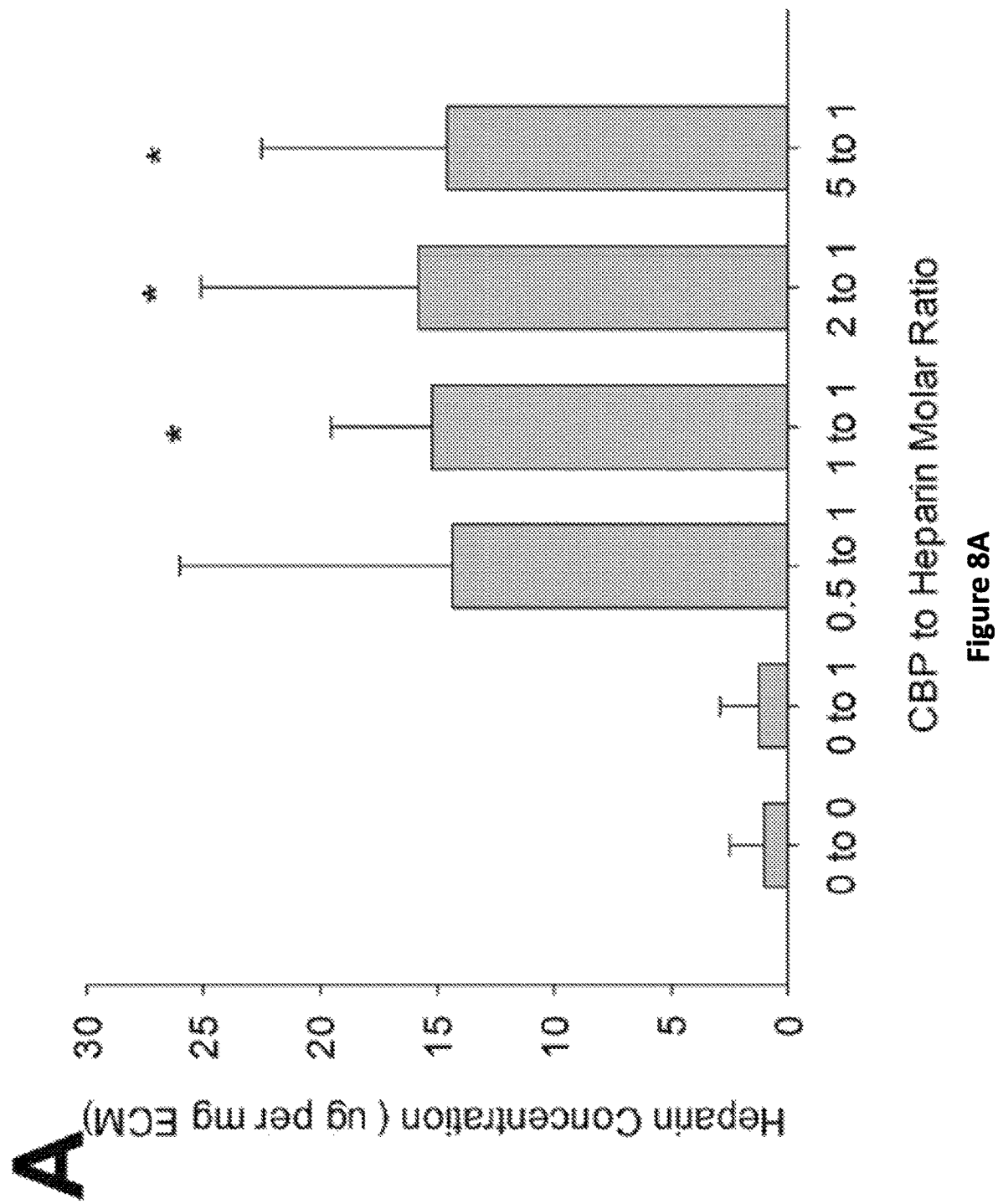
FIG. 8: Heparin quantification (A) and platelet adhesion (B) on ECM treated with conjugates of varying CBP to heparin molar ratio during optimization of CBP-heparin conjugates. * indicates p<0.05.

CBP-Heparin Delivers Functional Heparin to the ECM. Heparin sodium (average molecular weight 15000 Da) was conjugated to CBP or CBPi using the same carbodiimide chemistry used to link CBP to biotin. To accomplish this, CBP (or CBPi) and heparin sodium were reacted together at a 1:1 peptide to heparin molar ratio, resulting in a conjugated product consisting of 1.60±0.22 mol of CBP per mol of heparin or 1.77±0.05 mol of CBPi per mol of heparin (p=0.7929, CBP-heparin vs CBPi-heparin). These results confirm that the compositions of each CBP- and CBPi-heparin variants were similar. The peptide-heparin conjugates contain >80% heparin by mass (82.9% in CBP-heparin vs 81.6% in CBPi-heparin) and >10% peptide (11.1% in CBP-heparin vs 12.0% in CBPi-heparin; FIG. 3A). The bioactivity of the resulting heparin conjugate, measured by anti-Factor Xa activity, did not result in any significant difference between the two variants (36.4±5.7 U/mg in CBP-heparin vs 31.6±3.1 U/mg in CBPi-heparin, p=0.4056; FIG. 3B). However, there is a significant decrease in anti-Factor Xa activity compared to unconjugated heparin (200 U/mg, p<0.01). Vascular ECM from rodent aortas were modified with CBP-heparin (1 mg/mL) and led to a 7.2-fold increase in deposition of glycosaminoglycans (e.g., heparin) within ECM (15.25±4.29 μg GAG/mg ECM), beyond the baseline, untreated level (2.12±0.18 μg GAG/mg ECM, PBS-treated, p=0.0056 compared to CBP-heparin-treated). Moreover, conjugation of heparin to CBP led to a 5.4-fold increase in glycosaminoglycan content beyond ECM treated with unconjugated heparin sodium alone (2.81±0.19 μg GAG/mg ECM, heparin-sodium-treated, p=0.0062 compared to CBP-heparin-treated; FIG. 4A). CBPi-heparin (1 mg/mL) treated aorta ECM showed no statistically significant increase in the level of glycosaminoglycans beyond baseline (3.28±0.30 μg GAG/mg ECM, CBPi-heparin-treated). An increase in the molar ratio of CBP to heparin in the preparation of CPB-heparin beyond 1:1 (peptide/heparin) also did not lead to improved heparin binding to ECM (FIG. 8A); therefore, a molar ratio of 1:1 was used for all further studies.

Figure 9:
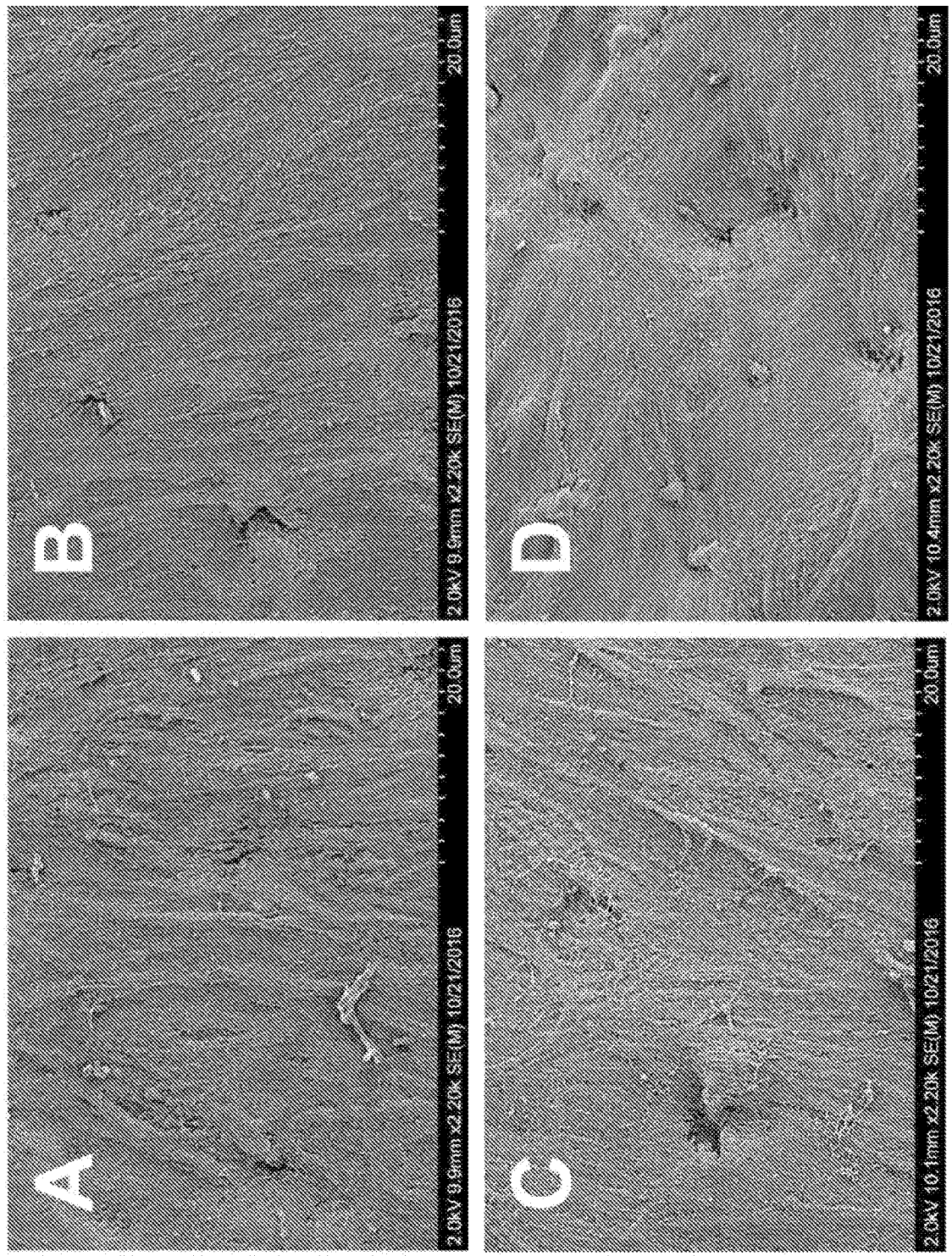
FIG. 9: SEM images of the lumen surface of ECM treated with PBS (A), heparin sodium (B), CBPi-heparin (C), or CBP-heparin (D).

The durability of the ECM modification by CBP-heparin was investigated by evaluating the retention of surface-bound heparin over time on ECM treated with CBP-heparin during incubation in complete EGM-2 growth medium at 37° C. (FIG. 4B). Within the first week, heparin concentration decreased by 68% from 15.25±4.29 μg GAG/mg ECM to 4.77±1.57 μg GAG/mg ECM, but still remained significantly above the baseline, untreated level (2.12±0.18 μg GAG/mg ECM, p<0.05). By the end of the second week, heparin concentration decreased to 2.46±1.55 μg GAG/mg ECM, similar to the baseline concentration (2.12±0.18 μg GAG/mg ECM, p=0.8759), and remained unchanged thereafter. This window of durability is still considered acceptable because the peak time for acute thrombosis after implantation is at early time points after restoration of blood flow.[1] The risk of thrombosis decreases as endothelial cells migrate and proliferate to cover discontinuous, exposed areas at the collagen-blood interface. To evaluate the surface morphology of ECM linked to CBP-heparin, we imaged the luminal surfaces of ECM modified with each heparin derivative or heparin alone (FIG. 9). However, we found no qualitative differences between ECM treated with PBS (FIG. 9A), heparin sodium alone (FIG. 9B), CBPi-heparin (FIG. 9C), or CBP-heparin (FIG. 9D).

Figure 5A:
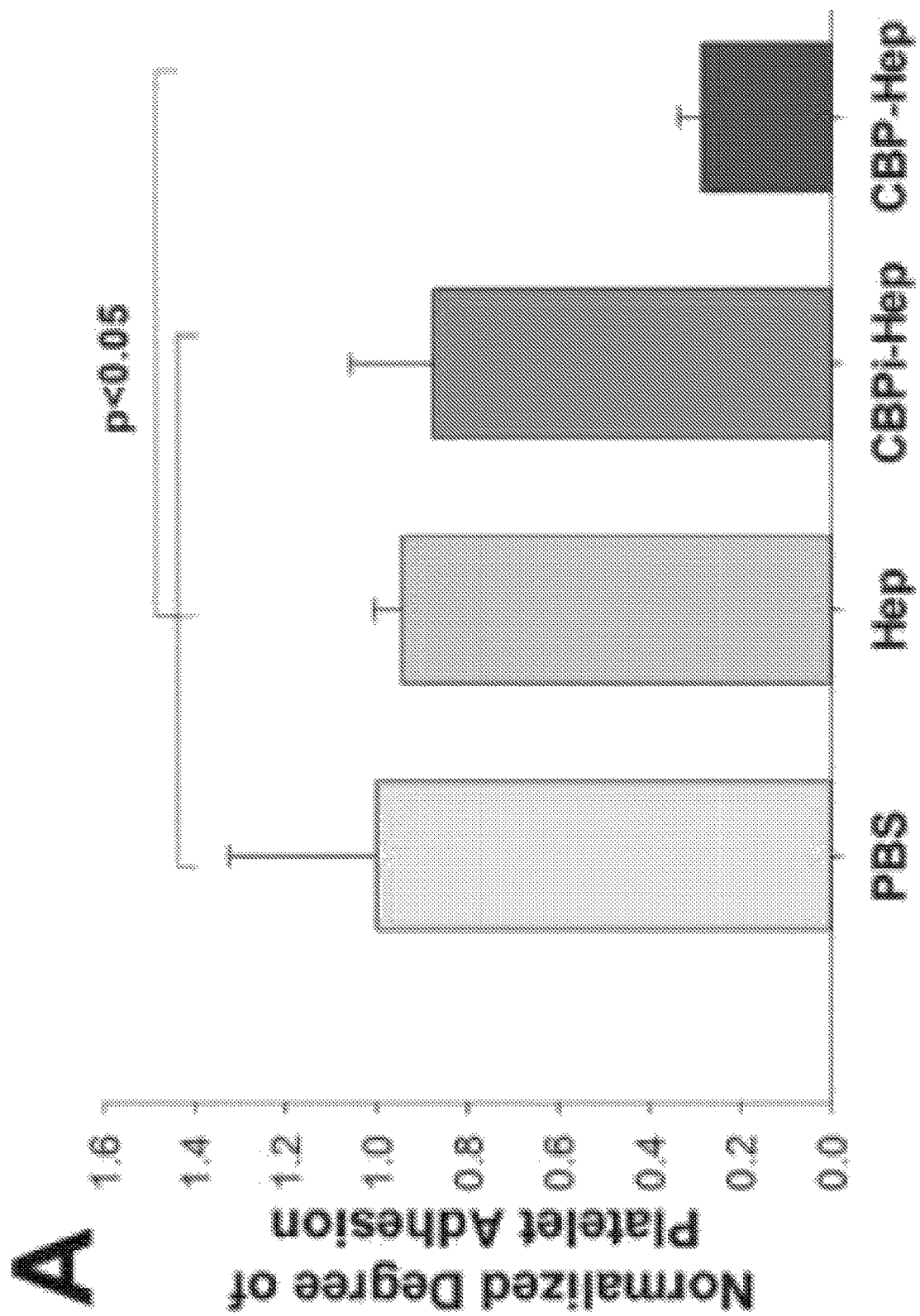
FIG. 5. (A) Platelet adhesion to arterial ECM treated with PBS, heparin sodium, CBPi-heparin, or CBP-heparin (n=3). The number of platelets binding to ECM treated with each condition was normalized to the number of platelets adherent to ECM treated with PBS alone as a reference. (B) Degree of clot formation by recalcified whole blood on arterial ECM with each separate modification (n=3). H&E images show the degree of blood clot formation on ECM treated with (C) PBS, (D) heparin sodium, (E) CBPi-heparin, or (F) CBP-heparin. Percent clot formation was determined by comparing mass of the blood clot formed to the mass of the ECM graft before addition of whole blood. Scale bar=200 µm.
Figure 8B:
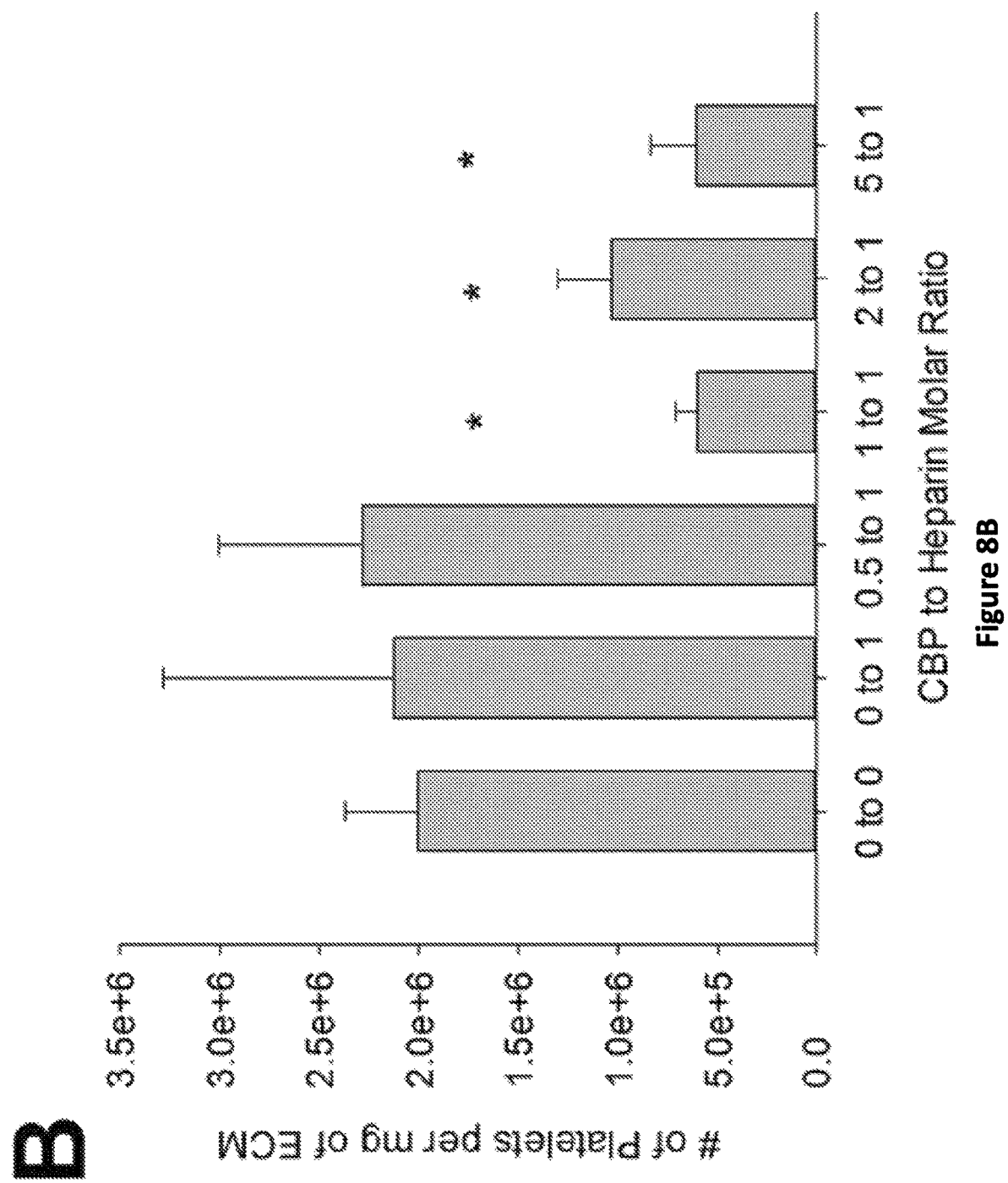

CBP-Heparin Reduces Thrombogenicity of the ECM. Platelets bind to ECM and, in particular, collagens, via surface receptors such as von Willebrand factor (VWF) and glycoprotein Ib (GPIb),[20] which triggers platelet activation and clot formation. We next investigated the biological effect of heparin linked to ECM via CBP by assessing the thrombogenicity of modified ECM. After incubation with platelet-rich plasma, ECM treated with CBP-heparin at 1 mg/mL exhibited a 71.5±5.0% reduction (p<0.01, CBP-heparin vs PBS) in the number of adherent platelets compared to PBS-treated ECM (control; FIG. 5A). ECM treated with heparin sodium alone at 1 mg/mL and CBPi-heparin at 1 mg/mL exhibited minimal antiplatelet activity, with only a 5.7±6.2% (p>0.05, compared to PBS) or 12.3±18.0% (p>0.05, compared to PBS) reduction in the number of platelets adherent to ECM, respectively. Our early investigation into the influence of the molar ratio of CBP to heparin on the biological function of the conjugated molecule did not demonstrate a correlation as altering the molar ratio 1:1 to 10:1 did not result in a further reduction in the number of platelets adherent to the ECM (FIG. 8B). Therefore, a molar ratio of 1:1 (peptide/heparin) was determined to be the optimal reaction conditions to synthesize the conjugate and optimize the biological function.

Figure 5B:
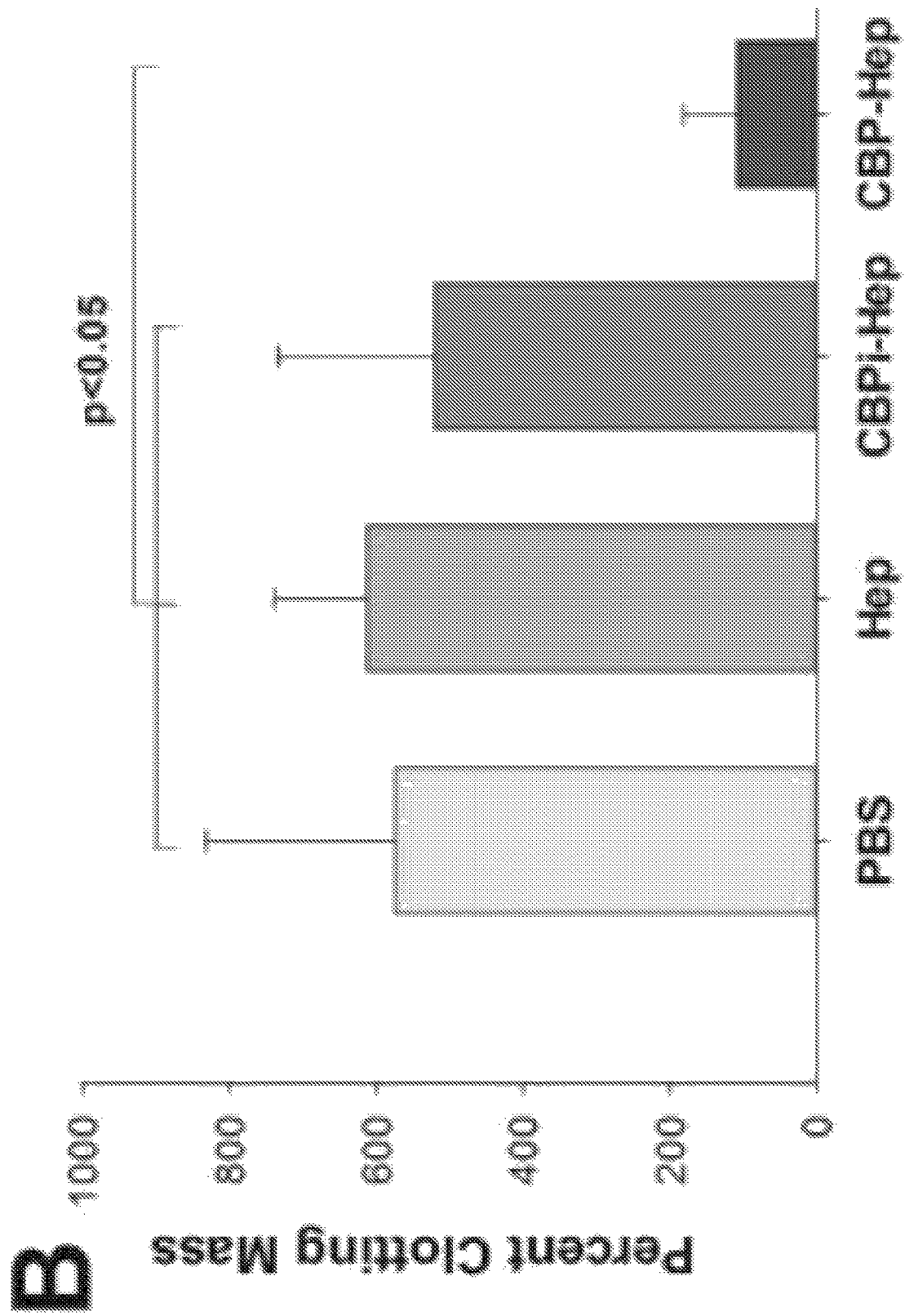

To investigate the effect of CBP-heparin on clot formation, we incubated treated ECM with recalcified anticoagulant blood, which clots within 30 min in the absence of ECM. ECM linked to heparin via the CBP-heparin conjugate resulted in a significant decrease in the mass of the resulting clot, relative to the mass of ECM, at the same time 30 min point (108.1±73.5%, [mass of clot/mass of ECM× 100%]) compared to ECM treated with PBS (573.7±258.8%, p=0.0134), heparin alone (612.1±126.0%, p<0.001), or CBPi-heparin (520.2±212.8%, p=0.0105; FIG. 5B). Thick blood clots were observed inside the lumen and along the exterior surface of decellularized vascular ECM grafts treated with PBS alone (FIG. 5C), heparin alone (FIG. 5D), or CBPi-heparin (FIG. 5E). However, minimal formation of thrombotic clots were observed within CBP-heparin-treated grafts, supporting the quantitative mass measurements of the retained clots noted above (FIG. 5F).

The addition of heparin to ECM to reduce its thrombogenicity has been investigated by other groups using various technologies, including covalent cross-linking,[21] layer-by-layer deposition,[22] and polymer-ECM hybridization.[13] We previously published several strategies to immobilize heparin to vascular ECM via synthetic polymer-ECM composites to reduce ECM thrombogenicity.[13,14] Specifically, poly(1,8-octamethylene citrate) (POC) or its derivative poly(1,8-octamethylene citrate)-co-cysteine (POC-Cys) was hybridized onto vascular ECM to form a polymer-ECM composite, which allowed for heparin immobilization via either carbodiimide chemistry13 or maleimide-thiol "click" chemistry.[14] However, neither POC nor POC-Cys is soluble in water, and the hybridization process involves complete ECM dehydration and subsequent rehydration. This hybridization strategy may not be optimal for tissues with a highly organized microvascular network, such as vital organs, and may damage the ECM ultrastructure during dehydration and rehydration. In contrast, the method presented here utilizing CBP as an intermediate linker to immobilize heparin can be carried out entirely in a hydrophilic environment with an equivalent antithrombotic effect as our previous polymer-ECM composite strategies.

Figure 6A:
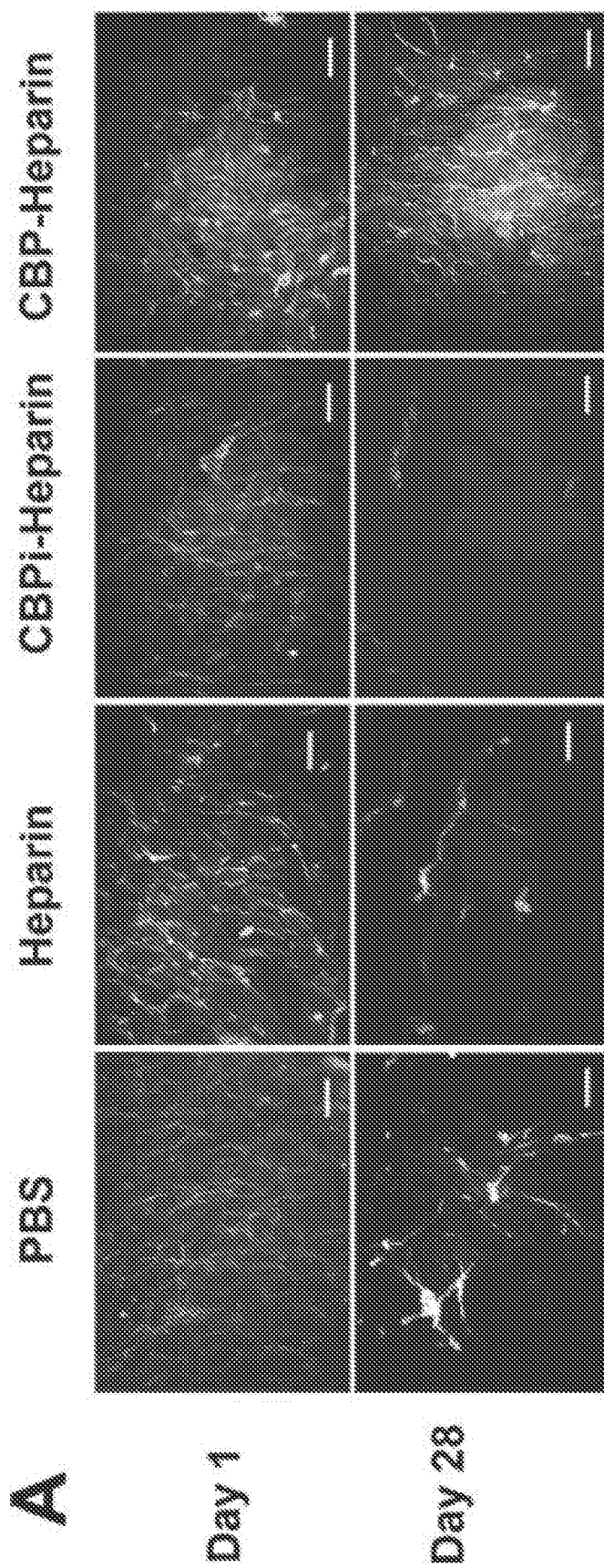
FIG. 6. (A) Phalloidin staining of endothelial cells seeded on the lumen of arterial ECM treated with PBS, heparin sodium, CBPi-heparin, or CBP-heparin at days 1 and 28 (scale bar=100 µm). (B) Quantitative analysis of adherent cell number on ECM at day 28, with the dash line indicating the initial cell seeding density at day 1 (n=3). (C) Quantitative analysis of VEGF concentration on ECM after incubating in endothelial cell complete medium (EGM-2, n=3).
Figure 6B:
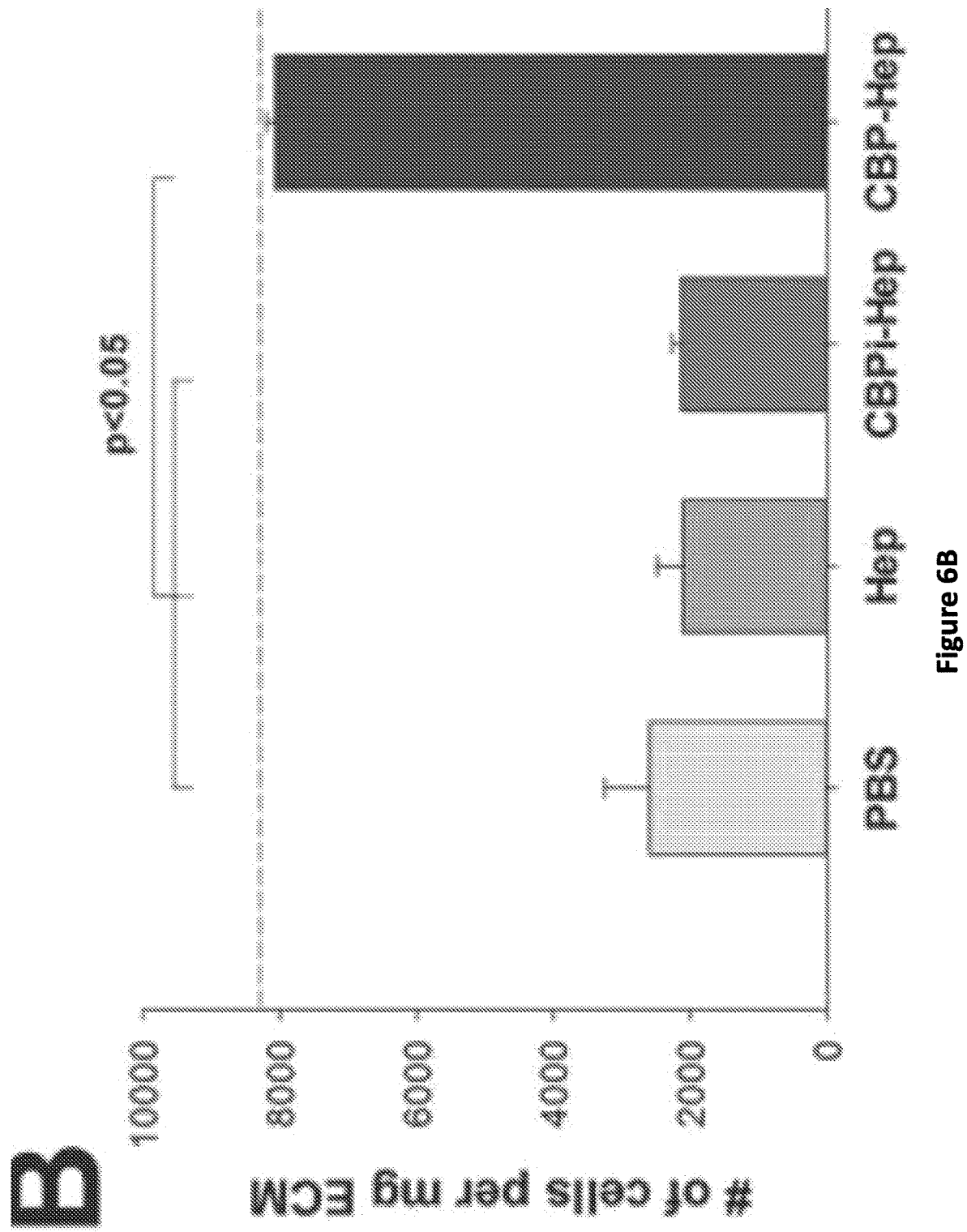
Figure 10:
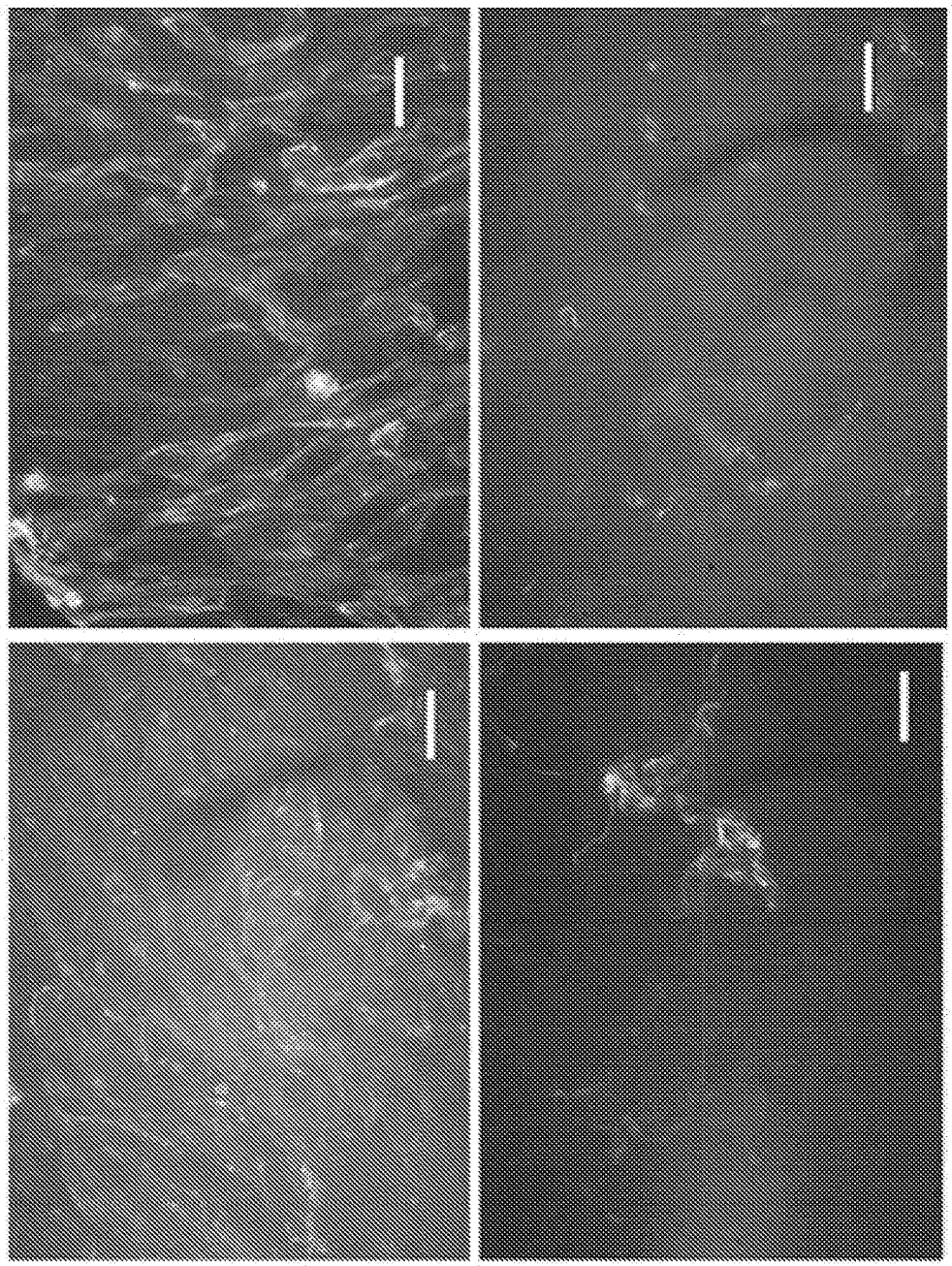
FIG. 10. Phalloidin staining of endothelial cells seeded on ECM treated with CBP and BCPi (both without heparin) at day 1 and day 287 (n=3). Minimal to no cells remain on ECM at day 28 for both CBP and BCPi without heparin. Scale bar=100 µm.

Immobilization of Heparin to ECM via CBP Stabilizes Endothelial Cell Attachment. An intact, continuous endothelium is critical to maintain proper function of the vascular system, including maintaining the selective barrier for solute filtration within the kidney, preventing thrombosis within the vasculature, and controlling inflammation and trafficking of leukocytes from the circulation and into extravascular tissues.[23] Endothelial cells are often seeded onto the lumen of vascular networks to provide these functions in various tissue engineering applications such as vascular grafts or vascularized thick scaffolds using decellularized tissues as matrices.[24,2,25] The long-term stability of endothelial cells is critical to maintaining vascular integrity, in general, including the functional durability of bioengineered tissues. We found that endothelial cells seeded effectively onto the lumen of ECM-based vascular grafts with good biocompatibility (i.e., cell adhesion and viability) and developed a continuous endothelial cell layer during the first day, regardless of the ECM modification strategy used (FIG. 6A). However, as cell-laden grafts were maintained in culture for up to 4 weeks, the number of adherent endothelial cells bound to ECM decreased significantly for ECM modified with PBS, heparin alone, or CBPi-heparin (FIGS. 6A,B). Only ECM modified with CBP-heparin supported and maintained the level of adherent endothelial cells over the 4-week time course study (FIGS. 6A,B). ECM grafts treated with CBP or CBPi peptides alone, both without conjugation to heparin, likewise did not preserve endothelial cell adhesion at 4 weeks (FIG. 10). Taken together, these data suggest a precise, and important role for specifically linking heparin to ECM via the CBP-heparin conjugate, which results in both improved anticoagulation and long-term endothelial cell attachment and maintenance of an endothelial layer, important biological functions that are specifically mediated by the heparin moiety within the conjugate.

Figure 6C:
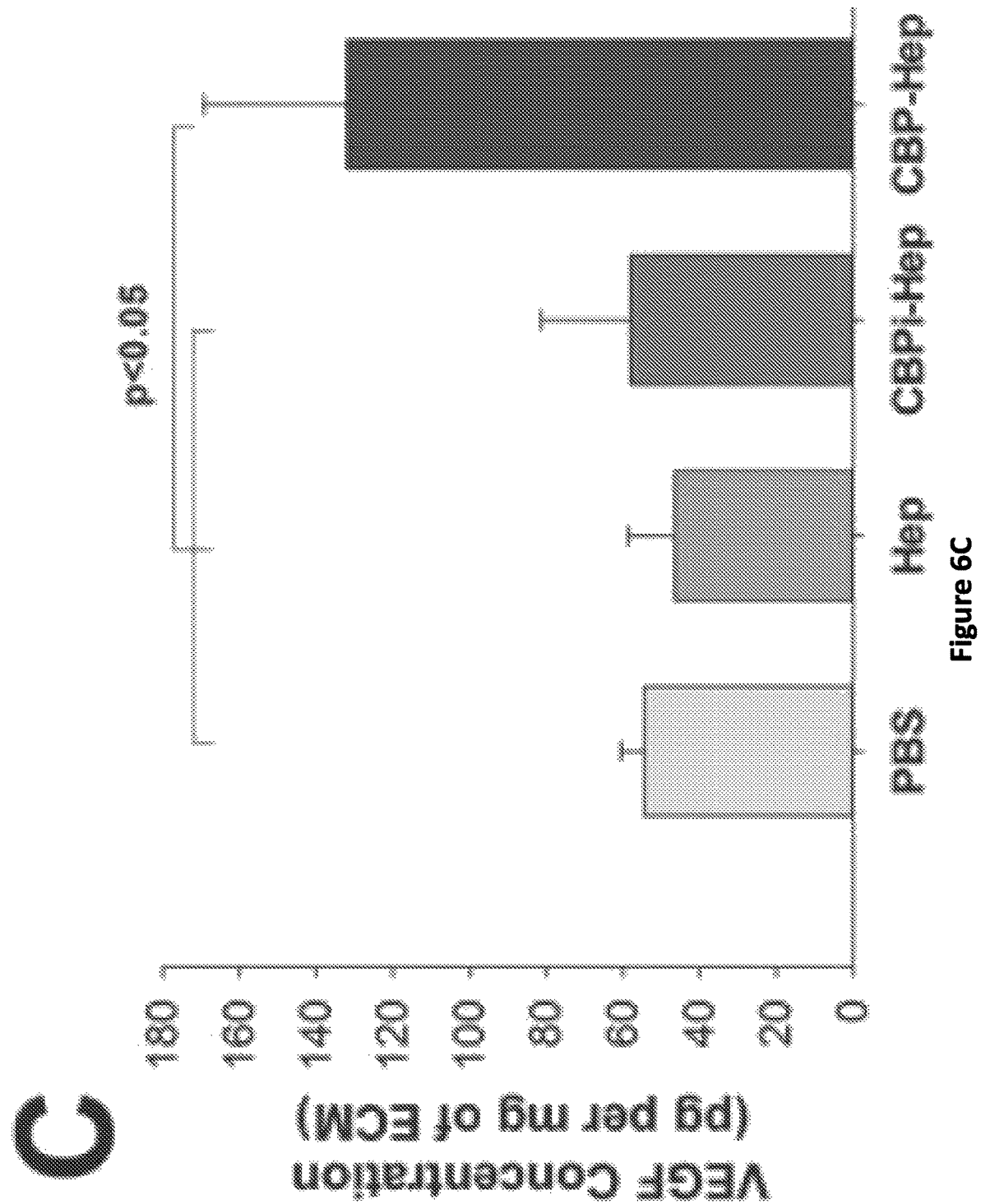

To investigate this observation further, we hypothesized that improved long-term attachment of endothelial cells to the ECM by CBP-heparin may be due to recruitment early on of soluble heparin-binding growth factors in the EGM-2 media, including vascular endothelial growth factor (VEGF),[26,27] basic fibroblast growth factor (bFGF)[28] and heparin-binding EGF-like growth factor (HB-EGF).[29] A quantitative analysis to measure VEGF within ECM grafts after incubation in EGM-2 for 3 days revealed that VEGF concentrations increased for all groups from the baseline level (26.8±8.4 pg/mg ECM, before incubation in EGM-2). However, the increase was significantly more pronounced for ECM pretreated with CBP-heparin (132.0±37.3 pg/mg ECM), compared to ECM treated with PBS alone (54.4±6.1 pg/mg ECM, p<0.05), ECM prepared with unconjugated heparin (46.5±12.1 pg/mg ECM, p<0.05), and ECM prepared with CBPi-heparin (58.0±23.3 pg/mg ECM, p<0.05; FIG. 6C). ECM-associated growth factors, such as VEGF, promote endothelial adhesion, migration, and survival,[30] which may explain the long term adhesion and maintenance of endothelial cells growing on CBP-heparin-treated ECM at 4 weeks. The dual effect of the CBP-heparin to both promote the long-term retention of endothelial cells on the lumen and improve thromboresistance at early time points will together reduce the risk of vascular occlusion and stenosis within the engineered tissue vasculature and improve graft function.

Limitations and Prospects. This strategy to noncovalently immobilize heparin onto ECM using CBP as an intermediate linker to bring heparin to the ECM also provides a platform for the immobilization of other bioactive molecules using a variety of ECM binding peptides. In this study, we chose to use CBP (CQDSETRTFY (SEQ ID NO:1)) as a proof-of-principle to develop targetable ECM modifiers to deliver bioactive agents (i.e., heparin) to vascular ECM. Collagen-binding peptides have been utilized by a number of groups for their specific binding to collagens. For example, Panitch et al. used a collagen-binding peptide as an anchor to immobilize various bioactive molecules for modulating collagen fibrillogenesis,[31,32] inhibiting MMP-mediated collagen degradation,[33] and inhibition of platelet adhesion and activation on collagen during balloon angioplasty.[34] Sistiabudi et al. also employed a collagen-binding peptide to modify the retinal Bruch membrane, to restore the retinal pigment epithelial (RPE) layer.[35-37]

In contrast, our study demonstrates the utility of heparin immobilization to prevent clot formation due to the removal of endothelial cells during decellularization and incomplete revascularization of the endothelial layer during recellularization. However, one limitation using CBP to immobilize heparin onto the ECM, as demonstrated in our study, is its limited longterm durability when bound to ECM (FIG. 4B). This limitation could potentially be overcome by selecting or identifying other peptide sequences with higher affinity to ECM proteins or using technologies to uncover novel sequences.[38] Another limitation is reduced heparin anticoagulant activity after peptide conjugation, as demonstrated by decreased anti-Factor Xa activity after conjugation. Using chemistry other than the EDC/NHS carbodiimide chemistry to conjugate peptide with heparin may help preserve heparin's bioactivity. Nevertheless, it is important to point out that although CBP-heparin has lower anti-Factor Xa activity in solution compared to heparin alone, once bound to ECM the effective antithrombotic activity of the conjugated heparin is significantly enhanced beyond ECM treated with unconjugated heparin alone due to its higher affinity for the matrix (FIG. 5).

Conclusions

We developed a strategy to synthesize CBP-heparin that selectively bindings to ECM proteins collagen IV and, to a lesser extent, collagen I. Moreover, we show that vascular ECM modified with CBP-heparin exhibits reduced thrombogenicity, improved long-term adhesion of endothelial cells, and increased binding of the growth factor VEGF. Taken together, we describe an easy to implement approach to help overcome the challenge of thrombosis in various tissue engineering applications, where decellularized tissues are used as biologic scaffold materials. This technology opens up new opportunities to develop patient-specific vascular grafts and vascular network in engineered organs using decellularized tissue ECM as scaffolds.

REFERENCES (1) Wang, Y.; Gallant, R. C.; Ni, H. Extracellular matrix proteins in the regulation of thrombus formation. Curr. Opin. Hematol. 2016, 23 (3), 280-7.
(2) Ott, H. C.; Matthiesen, T. S.; Goh, S. K.; Black, L. D.; Kren, S. M.; Netoff, T. I.; Taylor, D. A. Perfusiondecellularized matrix: using nature's platform to engineer a bioartificial heart. Nat. Med. 2008, 14 (2), 213-21.
(3) Soto-Gutierrez, A.; Zhang, L.; Medberry, C.; Fukumitsu, K.; Faulk, D.; Jiang, H.; Reing, J.; Gramignoli, R.; Komori, J.; Ross, M.; Nagaya, M.; Lagasse, E.; Stolz, D.; Strom, S. C.; Fox, I. J.; Badylak, S. F. A whole-organ regenerative medicine approach for liver replacement. Tissue Eng., Part C 2011, 17 (6), 677-86.
(4) Caralt, M.; Uzarski, J. S.; Iacob, S.; Obergfell, K. P.; Berg, N.; Bijonowski, B. M.; Kiefer, K. M.; Ward, H. H.; Wandinger-Ness, A.; Miller, W. M.; Zhang, Z. J.; Abecassis, M. M.; Wertheim, J. A. Optimization and critical evaluation of decellularization strategies to develop renal extracellular matrix scaffolds as biological templates for organ engineering and transplantation. Am. J. Transplant. 2015, 15 (1), 64-75.
(5) Ott, H. C.; Clippinger, B.; Conrad, C.; Schuetz, C.; Pomerantseva, I.; Ikonomou, L.; Kotton, D.; Vacanti, J. P. Regeneration and orthotopic transplantation of a bioartificial lung. Nat. Med. 2010, 16 (8), 927-33.
(6) Momtahan, N.; Sukavaneshvar, S.; Roeder, B. L.; Cook, A. D. Strategies and processes to decellularize and recellularize hearts to generate functional organs and reduce the risk of thrombosis. Tissue Eng., Part B 2015, 21 (1), 115-32.
(7) Murugesan, S.; Xie, J.; Linhardt, R. J. Immobilization of heparin: approaches and applications. Curr. Top. Med. Chem. 2008, 8 (2), 80-100.
(8) Schmidt, C. E.; Baier, J. M. Acellular vascular tissues: natural biomaterials for tissue repair and tissue engineering. Biomaterials 2000, 21 (22), 2215-31.
(9) Yamada, K. M.; Kennedy, D. W. Dualistic Nature of Adhesive Protein Function—Fibronectin and Its Biologically-Active Peptide-Fragments Can Autoinhibit Fibronectin Function. J. Cell Biol. 1984, 99 (1), 29-36.
(10) Boucaut, J. C.; Darribere, T.; Poole, T. J.; Aoyama, H.; Yamada, K. M.; Thiery, J. P. Biologically-Active Synthetic Peptides as Probes of Embryonic-Development—a Competitive Peptide Inhibitor of Fibronectin Function Inhibits Gastrulation in Amphibian Embryos and Neural Crest Cell-Migration in Avian Embryos. J. Cell Biol. 1984, 99 (5), 1822-1830.
(11) Farndale, R. W.; Sayers, C. A.; Barrett, A. J. A direct spectrophotometric microassay for sulfated glycosaminoglycans in cartilage cultures. Connect. Tissue Res. 1982, 9 (4), 247-8.
(12) Ellman, G. L.; Courtney, K. D.; Andres, V., Jr.; Featherstone, R. M. A new and rapid colorimetric determination of acetylcholinesterase activity. Biochem. Pharmacol. 1961, 7 (2), 88-95.
(13) Jiang, B.; Akgun, B.; Lam, R. C.; Ameer, G. A.; Wertheim, J. A. A polymer-extracellular matrix composite with improved thromboresistance and recellularization properties. Acta Biomater. 2015, 18, 50-8.
(14) Jiang, B.; Suen, R.; Wang, J. J.; Zhang, Z. J.; Wertheim, J. A.; Ameer, G. A. Mechanocompatible Polymer-Extracellular-Matrix Composites for Vascular Tissue Engineering. Adv. Healthcare Mater. 2016, 5 (13), 1594-605.
(15) Hoshi, R. A.; Van Lith, R.; Jen, M. C.; Allen, J. B.; Lapidos, K. A.; Ameer, G. The blood and vascular cell compatibility of heparinmodified ePTFE vascular grafts. Biomaterials 2013, 34 (1), 30-41.
(16) O'Brien, J.; Wilson, I.; Orton, T.; Pognan, F. Investigation of the Alamar Blue (resazurin) fluorescent dye for the assessment of mammalian cell cytotoxicity. Eur. J. Biochem. 2000, 267 (17), 5421-6.
(17) Mao, Y.; Schwarzbauer, J. E. Fibronectin fibrillogenesis, a cellmediated matrix assembly process. Matrix Biol. 2005, 24 (6), 389-99.
(18) Bosman, F. T.; Stamenkovic, I. Functional structure and composition of the extracellular matrix. J. Pathol 2003, 200 (4), 423-8.
(19) Martino, M. M.; Briquez, P. S.; Guc, E.; Tortelli, F.; Kilarski, W. W.; Metzger, S.; Rice, J. J.; Kuhn, G. A.; Muller, R.; Swartz, M. A.; Hubbell, J. A. Growth factors engineered for super-affinity to the extracellular matrix enhance tissue healing. Science 2014, 343 (6173), 885-8.
(20) Nieswandt, B.; Watson, S. P. Platelet-collagen interaction: is GPVI the central receptor? Blood 2003, 102 (2), 449-461.
(21) Conklin, B. S.; Richter, E. R.; Kreutziger, K. L.; Zhong, D. S.; Chen, C. Development and evaluation of a novel decellularized vascular xenograft. Med. Eng. Phys. 2002, 24 (3), 173-83.
(22) Bruinsma, B. G.; Kim, Y.; Berendsen, T. A.; Ozer, S.; Yarmush, M. L.; Uygun, B. E. Layer-by-layer heparinization of decellularized liver matrices to reduce thrombogenicity of tissue engineered grafts. J. Clin. Transl. Res. 2015, 1 (1), 04.
(23) Jiang, B.; Perrin, L.; Kats, D.; Meade, T.; Ameer, G. Enabling non-invasive assessment of an engineered endothelium on ePTFE vascular grafts without increasing oxidative stress. Biomaterials 2015, 69, 110-20.
(24) Lichtenberg, A.; Tudorache, I.; Cebotari, S.; Ringes-Lichtenberg, S.; Sturz, G.; Hoeffler, K.; Hurscheler, C.; Brandes, G.; Hilfiker, A.; Haverich, A. In vitro re-endothelialization of detergent decellularized heart valves under simulated physiological dynamic conditions. Biomaterials 2006, 27 (23), 4221-9.
(25) Baptista, P. M.; Siddiqui, M. M.; Lozier, G.; Rodriguez, S. R.; Atala, A.; Soker, S. The Use of Whole Organ Decellularization for the Generation of a Vascularized Liver Organoid. Hepatology 2011, 53 (2), 604-617.
(26) Leung, D. W.; Cachianes, G.; Kuang, W. J.; Goeddel, D. V.; Ferrara, N. Vascular Endothelial Growth-Factor Is a Secreted Angiogenic Mitogen. Science 1989, 246 (4935), 1306-1309.
(27) Ferrara, N.; Henzel, W. J. Pituitary follicular cells secrete a novel heparin-binding growth factor specific for vascular endothelial cells. Biochem. Biophys. Res. Commun. 1989, 161 (2), 851-8.
(28) Sakiyama-Elbert, S. E.; Hubbell, J. A. Development of fibrin derivatives for controlled release of heparin-binding growth factors. J. Controlled Release 2000, 65 (3), 389-402.
(29) Higashiyama, S.; Abraham, J. A.; Miller, J.; Fiddes, J. C.; Klagsbrun, M. A Heparin-Binding Growth-Factor Secreted by Macrophage-Like Cells That Is Related to Egf. Science 1991, 251 (4996), 936-939.
(30) Hutchings, H.; Ortega, N.; Plouet, J. Extracellular matrix-bound vascular endothelial growth factor promotes endothelial cell adhesion, migration, and survival through integrin ligation. FASEB J. 2003, 17 (11), 1520-2.
(31) Paderi, J. E.; Panitch, A. Design of a synthetic collagen-binding peptidoglycan that modulates collagen fibrillogenesis. Biomacromolecules 2008, 9 (9), 2562-6.
(32) Paderi, J. E.; Sistiabudi, R.; Ivanisevic, A.; Panitch, A. Collagenbinding peptidoglycans: a biomimetic approach to modulate collagen fibrillogenesis for tissue engineering applications. Tissue Eng., Part A 2009, 15 (10), 2991-9.
(33) Stuart, K.; Paderi, J.; Snyder, P. W.; Freeman, L.; Panitch, A. Collagen-binding peptidoglycans inhibit MMP mediated collagen degradation and reduce dermal scarring. PLoS One 2011, 6 (7), e22139.

(34) Paderi, J. E.; Stuart, K.; Sturek, M.; Park, K.; Panitch, A. The inhibition of platelet adhesion and activation on collagen during balloon angioplasty by collagen-binding peptidoglycans. Biomaterials 2011, 32 (10), 2516-23. (35) Sistiabudi, R.; Ivanisevic, A. Collagen-binding peptide interaction with retinal tissue surfaces. Langmuir 2008, 24 (5), 1591-4.

(36) Sistiabudi, R.; Paderi, J.; Panitch, A.; Ivanisevic, A. Modification of native collagen with cell-adhesive peptide to promote RPE cell attachment on Bruch's membrane. Biotechnol. Bioeng. 2009, 102 (6), 1723-9.

(37) Sistiabudi, R.; Ivanisevic, A. Dip-Pen Nanolithography of Bioactive Peptides on Collagen-Terminated Retinal Membrane. Adv. Mater. 2008, 20 (19), 3678-3681.

(38) Pasqualini, R.; Ruoslahti, E. Organ targeting in vivo using phage display peptide libraries. Nature 1996, 380 (6572), 364-6.

Example 2—Collagen-Binding Peptide (CBP)-Heparin Conjugates Having Increased Molecular Valency of CBP Relative to Heparin Avidity is defined as 'functional affinity' and is the accumulated strength of all binding interactions. As discussed above, we developed a lead compound comprising Collagen-Binding Peptide (CBP) conjugated to unfractionated heparin (UHF) (i.e., CBP:Heparin), with one CBP oligo-unit per UFH. Although we have shown specific and durable binding using this configuration, our goal was to increase the cumulative binding affinity (e.g., the avidity) of the compound. The development of a panel of CBP:Heparin sub-types, that vary in chemical arrangement and binding strength, would translate into reduced dose amount and decreased dose frequency, and would further improve the safety profile of the compound. Thus, we developed and tested a panel of CBP:Heparin variants that differ in the number of repeated CBP oligopeptides arranged in a linear configuration. FIG. 11 illustrates a panel of CBP:Heparin variants having repeated CBP oligopeptides arranged in a linear configuration.

Heparin(Cy5)-CBP conjugates were synthesized using N-(3-dimethylaminopropyl)-N'-ethylcarbodiimide/N-hydroxyl succinimide (EDC/NHS) chemistry (1,2). Briefly, 1 mM of heparin sodium salt or fluorescently pre-conjugated Heparin(Cyanine5) (Hep-Cy5) mixed with 120 mM EDC and 60 mM NHS in 2-(N-morpholino) ethanesulfonic acid (MES) buffer at pH 6.5. This was rocked for 4 hours at 20° C. 1 mM of cleavage binding peptide (CQDSETRTFY (SEQ ID NO:1), CBP) or a scrambled sequence (CDEFQRSTTY (SEQ ID NO:2), CBPi) was added, and allowed to rock overnight at 4° C. This mixture was dialyzed to exclude molecules above 3.5 kDa and lyophilized to dry. Four molecular assays were used to assess the functional synthesis of these conjugates. An Ellman's assay is capable of colormetrically labeling the thiol containing cysteine amino acid, and was used to assess the cysteine molar quantity of the whole conjugate (3). A dimethylmethylene blue assay was used to stain the glycosaminoglycan present in heparin conjugates to determine the heparin molar quantity (4). A colormetric kit was used to assess clotting via factor Xa (5). Effective CBP related binding of the conjugate was measured via the Cy5 fluorophore, using a 24 hour incubation with surface coated collagen IV (6). Together, these assays were used to assess the conjugation of CBP onto Heparin, and the functional anti-clotting and collagen IV binding of the resulting molecule.

Figure 13:
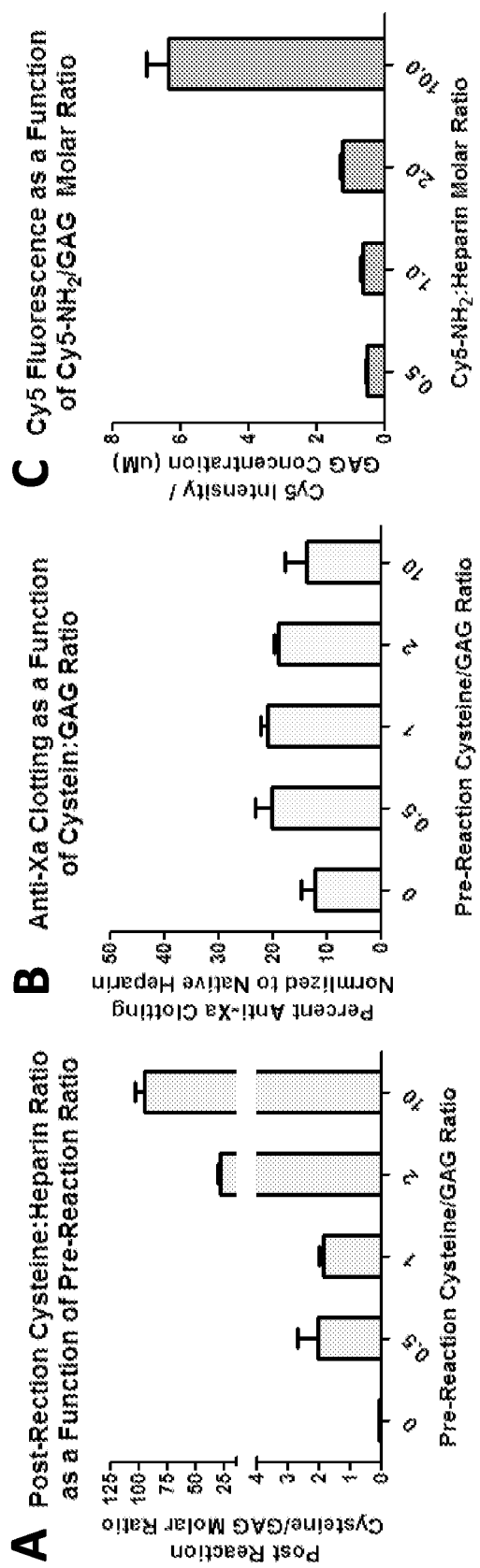
FIG. 13. Molecular assays of heparin NHS conjugation, including (A) molar optimization using cysteine, (B) reduction in anti-Xa clotting of this molar optimization, and (C) Cy5-NH2 conjugation to assess fluorescence quenching. Assays include Ellman's thiol labeling assay normalized to GAG staining dimethylmethylene blue (DMMB) assay, percent clotting assessed by anti-factor Xa compared to native heparin, and fluorescent Cy5 intensity.

Chemistry was optimized by increasing the peptide to heparin ratio, as multiple carboxyl sites are present to form covalent linkages. Optimization was done by substituting CBP with L-cysteine, which can be assayed by its thiol content, and Cy5-$NH_2$ with far-red fluorescent detection. Molar ratios 0, 0.5, 1, 2, 10 of substitute to heparin were chosen. To determine any loss of heparin activity due to these modifications, the anti-Xa clotting of these conjugates to determine was assessed. This is shown in FIG. 13. It was shown that the ratios 2-10 showed markedly significant increases (25-100 cysteine/GAG), suggesting the creation of a multivalent conjugate (FIG. 13A). Compared to un-modified heparin, cysteine to heparin conjugated lost ~80% of their anti-clotting capability (FIG. 13B). When these ratios were corroborated with Cy5-$NH_2$ instead of cysteine (FIG. 13C), a comparable trend was noted. Fluorescent quenching did not occur, which is typical of fluorophore crowding (7).

Figure 14:
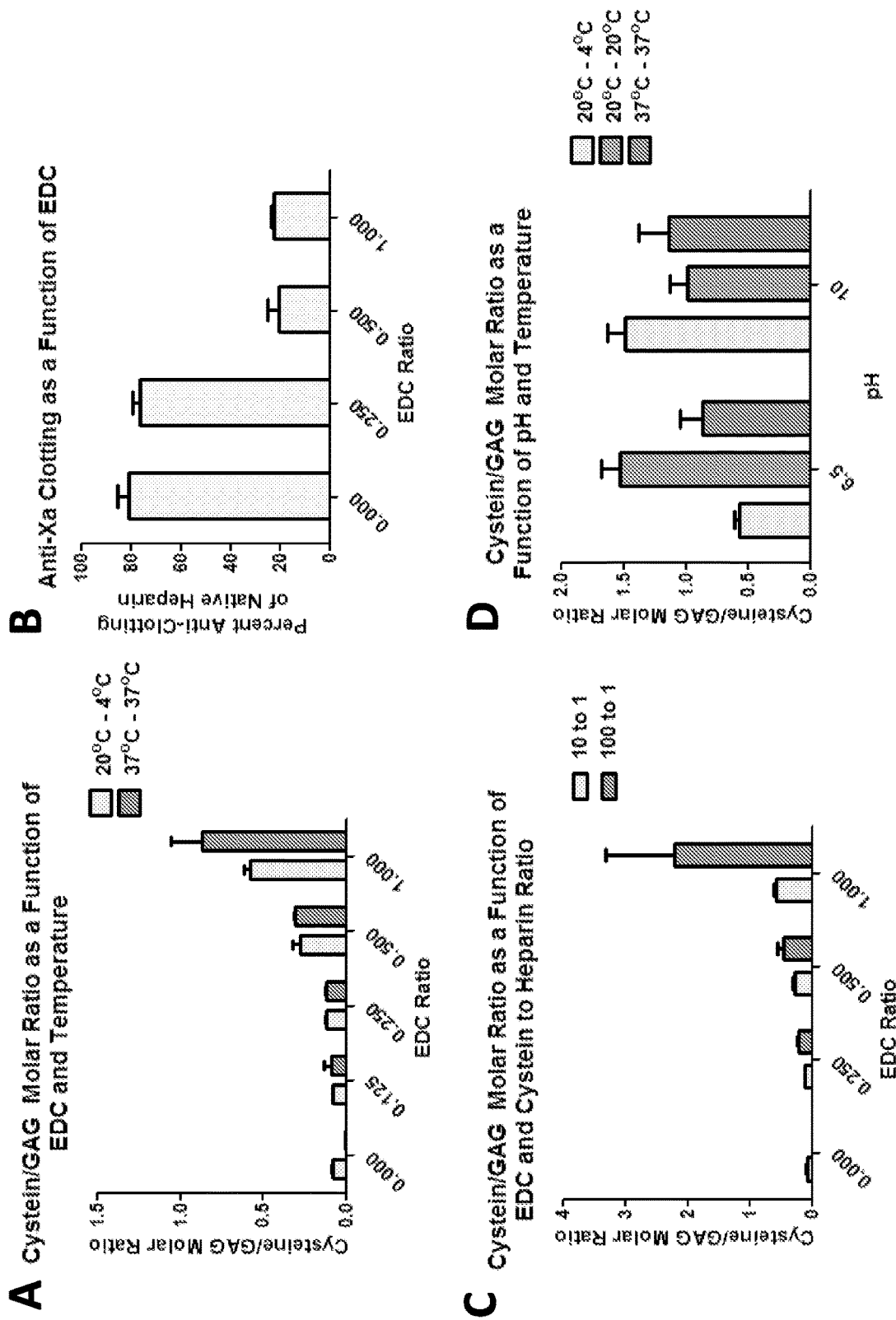
FIG. 14. Molecular assays of heparin NHS conjugation, including EDC reduction to mitigate heparin damage measured by (A) cysteine/GAG ratio, (B) anti-Xa clotting, and (C) raising the cysteine to heparin molar ratio. In addition, (C) temperature and pH optimization. Assays include (Ellman's thiol labeling assay normalized to GAG staining DMMB assay and percent clotting assessed by anti-factor Xa compared to unmodified heparin.

To mitigate the loss of anti-clotting, EDC molar ratio to heparin was sequentially halved (1 to 0.125, with 1-cysteine: heparin being 10:1) and reaction temperature was increased to 37° C. to improved the reaction kinetics (FIG. 14A). Higher temperature improved the cysteine/GAG ratio only at the 1:1 ratio, while lowering the EDC drastically decreased the cysteine conjugation. Anti-clotting (FIG. 14B) was only mitigated at EDC ratios below 0.25. In attempt to compensate for the loss due to lower EDC ratios, the 1-cysteine:heparin ratio was increased to 100:1 (FIG. 14C). Retaining the 1:1 EDC:Heparin molar ratio proves necessary for this chemistry, as heparin activity cannot be retained by temperature and drastic increased in L-cysteine, and likely any form of CBP/CBPi. In an attempt to improve kinetics due to pH and temperature, reaction pH and temperatures were varied between 6.5 (standard) and 10, and 4° C. (standard), 20° C., and 37° C., respectively. Improvements were note in pH 10 for the 20° C. group, and at 20° C. compared between temperatures.

Figure 15:
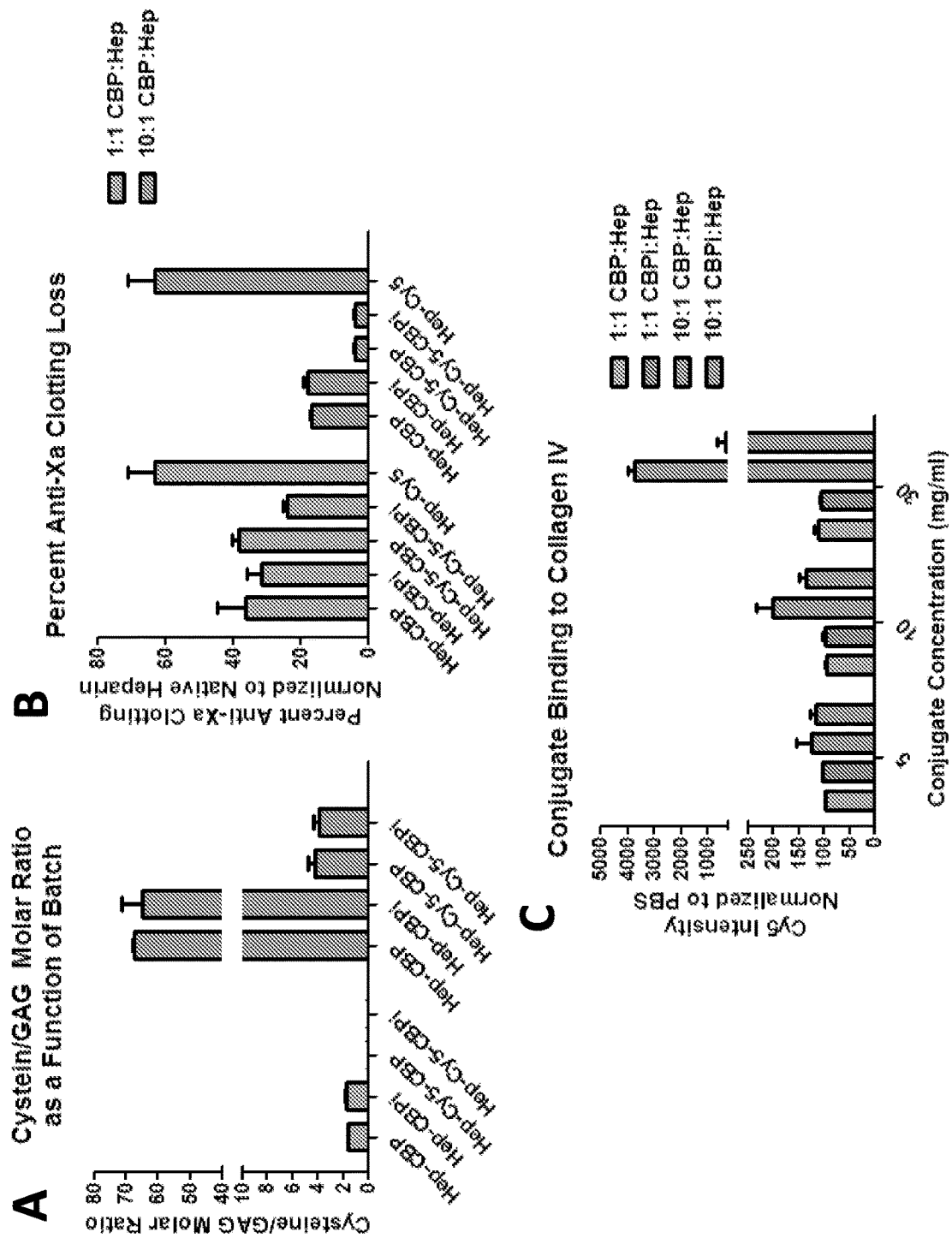
FIG. 15. Molecular assays of heparin NHS conjugation to assess the batch to batch improvement (from 1:1 to 10:1 for Heparin/Heparin-Cy5:CBP/CBPi). Assays include (A) Ellman's thiol labeling assay normalized to GAG staining DMMB assay, (B) percent clotting assessed by anti-factor Xa compared to native heparin, and (C) heparin conjugate binding to collagen IV.

Using the noted improvements (FIG. 13 and FIG. 14), the optimal conjugating of CBP and the scrambled CBPi, to heparin and Hep-Cy5 was performed. This is compared, batch to batch, in FIG. 15. Next, we compared standard chemistry (4° C., 1:1 molar ratio CBP:Hep-Cy5) to improved kinetics (20° C., 10:1 molar ratio CBP:Hep-Cy5). Polymeric heparin was used in these examples, and the molar ratio in these examples is based on the molecular weight of the polymeric heparin used in the examples, which is 28 kD and translates to ~60 heparin monomers per polymer.

The cysteine:GAG ratio of both Hep-Cy5 (~4 mol/mol increase) and heparin (~60 mol/mol increase) was tremendously improved by these conditions (FIG. 15A). The anti-Xa clotting was reduced to 25-40%, 15-20%, and 5% for 1:1 (Heparin and Hep-Cy5), 10:1 (Heparin), and 10:1 (Hep-Cy5) CBP/CBPi to heparin ratios, respectively (FIG. 15B). As the CBP/CBPi conjugation increases, this anti-clotting loss appears unavoidable. Pre-conjugated Hep-Cy5 is already 80% anti-Xa activity before our chemistry, further compounding this. This embodiment is intended to be used with or without the Cy5 label (or another fluorescent or radiologically traceable marker). At 30 mg/ml, the improved batch of CBP-Hep(Cy5) binds to collagen IV (FIG. 15C) four times more than the scrambled CBPi control. In summary, these improvements led to the synthesis of a multivalent and functionally improved Heparin(Cy5)-CBP and Heparin-CBP conjugate.

REFERENCES

1. Murugesan, S., Xie, J. & Linhardt, R. J. Immobilization of Heparin: Approaches and Applications. Curr Top Med Chem 8, 80-100 (2008).
2. Wissink, M. J. et al Immobilization of heparin to EDC/NHS-crosslinked collagen. Characterization and in vitro evaluation. Biomaterials 22, 151-163 (2001).
3. Winther, J. R. & Thorpe, C. Quantification of Thiols and Disulfides. Biochim Biophys Acta 1840, (2014).
4. Barbosa, I. et al. Improved and simple micro assay for sulfated glycosaminoglycans quantification in biological extracts and its use in skin and muscle tissue studies. Glycobiology 13, 647-653 (2003).
5. Beyer, J. et al. Evaluation of a Heparin-Calibrated Anti-factor Xa Assay for Measuring the Anticoagulant Effect of Oral Direct Xa Inhibitors. Clin. Appl. Thromb. Hemost. 22, 423-428 (2016).
6. Jiang, B., Suen, R., Wertheim, J. A. & Ameer, G. A. Targeting Heparin to Collagen within Extracellular Matrix Significantly Reduces Thrombogenicity and Improves Endothelialization of Decellularized Tissues. Biomacromolecules 17, 3940-3948 (2016).
7. Rao, A. N., Rodesch, C. K. & Grainger, D. W. Real-time fluorescent image analysis of DNA spot hybridization kinetics to assess microarray spot heterogeneity. Anal Chem 84, 9379-9387 (2012).

In the foregoing description, it will be readily apparent to one skilled in the art that varying substitutions and modifications may be made to the invention disclosed herein without departing from the scope and spirit of the invention. The invention illustratively described herein suitably may be practiced in the absence of any element or elements, limitation or limitations which is not specifically disclosed herein. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention. Thus, it should be understood that although the present invention has been illustrated by specific embodiments and optional features, modification and/or variation of the concepts herein disclosed may be resorted to by those skilled in the art, and that such modifications and variations are considered to be within the scope of this invention.

Citations to a number of patent and non-patent references are made herein. The cited references are incorporated by reference herein in their entireties. In the event that there is an inconsistency between a definition of a term in the specification as compared to a definition of the term in a cited reference, the term should be interpreted based on the definition in the specification.

The invention claimed is:

1. A heparin conjugate comprising heparin conjugated to an extracellular matrix (ECM)-binding peptide that binds to one or more components of an extracellular matrix wherein the ECM-binding peptide is conjugated directly or indirectly to heparin via an amide bond formed between a carboxyl group of heparin and an N-terminal amino group of the ECM-binding peptide or via an amide bond formed between a carboxyl group of heparin and an N-terminal amino group of a linking peptide that links the ECM-binding peptide to heparin, wherein the ECM-binding peptide is a collagen-binding peptide (CBP) comprising an amino acid sequence of one or more of SEQ ID NOs: 1-13, and wherein the heparin conjugate has a formula (CBP-LS)$_n$-CBP-Heparin, wherein LS is a linking sequence comprising 2-10 amino acids, wherein the 2-10 amino acids are selected from the group consisting of glycine (G) and serine (S), and n is at least 1.

2. The heparin conjugate of claim 1, comprising heparin conjugated directly to the CBP via an amide linkage between a carboxyl group of the heparin and the N-terminal amino group of the peptide.

3. The heparin conjugate of claim 1, wherein the ECM-binding peptide has an amino acid sequence of no more than about 15 amino acids.

4. The heparin conjugate of claim 1, wherein the ECM-binding peptide comprises the amino acid sequence CQDSETRTFY (SEQ ID NO:1).

5. The heparin conjugate claim 1, further comprising a conjugated fluorophore or a radiological tracer.

6. A pharmaceutical composition comprising the heparin conjugate of claim 1 and one or more of a carrier, an excipient, or a diluent.

7. A method of treating a vascular injury or condition in a subject in need thereof, the method comprising administering the pharmaceutical composition of claim 6 to the subject, wherein the vascular injury or condition is selected from one or more of vascular anastomosis, angioplasty, arteriovenous fistula, or arteriovenous graft.

8. A method for medical imaging a subject, comprising administering the heparin conjugate conjugated to a fluorophore or radiological tracer of claim 5 to the subject and detecting the fluorophore or the radiological tracer in the subject.

9. A biological material or synthetic material comprising the heparin conjugate of claim 1.

10. A decellularized biological material comprising the heparin conjugate of claim 1.

11. The decellularized biological material of claim 10, wherein the decellularized biological material is decellularized extracellular matrix (ECM) of vascular tissue.

12. A vascular graft comprising or consisting of the ECM of claim 11.

13. A method for making the heparin conjugate of claim 1, the method comprising activating a carboxyl group of heparin and covalently attaching the ECM-binding peptide or the linking peptide to the activated carboxyl group via the N-terminal amino group of the ECM binding peptide or the linking peptide.

14. A method for preparing a graft, the method comprising exposing biological material or synthetic material to the heparin conjugate of claim 1, wherein the biological material or synthetic material comprises collagen.

15. The heparin conjugate of claim 1, wherein n is from 2 to 6.

16. The method of claim 14, wherein the biological material is decellularized extracellular matrix (ECM) of cellular tissue.

* * * * *